United States Patent [19]
Dimaio et al.

[11] Patent Number: 6,057,314
[45] Date of Patent: May 2, 2000

[54] LOW MOLECULAR WEIGHT BICYCLIC THROMBIN INHIBITORS

[75] Inventors: John Dimaio, Montreal; M. Arshad Siddiqui, Saint-Laurent; John W. Gillard, Baie d'Urfe; Yves St-Denis; Micheline Tarazi, both of Montreal; Patrice Preville, Saint-Charles Borromee; Sophie Levesque, Laval; Benoit Bachand, Montreal, all of Canada; Annette Marian Doherty, Paris, France; Jeremy John Edmunds, Ypsilanti, Mich.

[73] Assignee: Biochem Pharma Inc., Laval, Canada

[21] Appl. No.: 08/880,885

[22] Filed: Jun. 23, 1997

Related U.S. Application Data

[63] Continuation of application No. PCT/CA95/00708, Dec. 21, 1995.

[51] Int. Cl.$^7$ .......................... A61K 31/54; A01N 43/58; C07D 265/36; C07D 279/02
[52] U.S. Cl. ................... 514/224.2; 514/230.5; 514/249; 544/47; 544/105; 544/278
[58] Field of Search ............................ 544/47, 105, 278; 514/224.2, 230.5, 249

[56] References Cited

U.S. PATENT DOCUMENTS

| | | | |
|---|---|---|---|
| 3,920,660 | 11/1975 | Fontanella et al. | 250/250 |
| 4,046,876 | 9/1977 | Okamoto et al. | 424/177 |
| 4,096,255 | 6/1978 | Kikumoto et al. | 424/246 |
| 4,097,472 | 6/1978 | Okamoto et al. | 424/177 |
| 4,097,591 | 6/1978 | Okamoto et al. | 424/177 |
| 4,173,630 | 11/1979 | Okamoto et al. | 424/177 |
| 4,318,904 | 3/1982 | Shaw et al. | 424/177 |
| 4,781,866 | 11/1988 | Maryanoff et al. | 260/506 |
| 5,196,404 | 3/1993 | Maraganore et al. | 514/13 |

FOREIGN PATENT DOCUMENTS

| | | |
|---|---|---|
| 1131621 | 9/1982 | Canada . |
| 2055850 | 5/1992 | Canada . |
| 2076311 | 2/1993 | Canada . |
| 2114153 | 7/1994 | Canada . |
| 0 276 014 | 7/1988 | European Pat. Off. . |
| 0 291 982 | 11/1988 | European Pat. Off. . |
| 0 333 356 | 9/1989 | European Pat. Off. . |
| 0 341 607 | 11/1989 | European Pat. Off. . |
| 91/02750 | 3/1991 | WIPO . |
| 92/06549 | 4/1992 | WIPO . |
| 92/08709 | 5/1992 | WIPO . |
| 93/15756 | 8/1993 | WIPO . |
| 93/22344 | 11/1993 | WIPO . |
| 94/08941 | 4/1994 | WIPO . |
| 94/17817 | 8/1994 | WIPO . |

OTHER PUBLICATIONS

J.M. Altenburger et al, "General Synthesis of Polyfunctionalized Fluoromethleneketone Retroamides as Potential Inhibitors of Thrombin", Dec. 1991, pp. 7255–7258, vol. 32, No. 49, Tetrahedron Letters.

Edwin J. Iwanowicz et al., "α–Hydroxy– and α–Ketoester Functionalized Thrombin Inhibitors", 1992, pp. 1607–1612, vol. 2, No. 12, Bioorg. & Med. Chem. Letters.

Chia–Lin J. Wang et al, Synthesis of Phosphonopeptides as Thrombin Inhibitors[1] 1992, pp. 7667–7670, vol. 33, No. 50, Tetrahedron Letters.

Carlo Tapparelli et al., "In Vitro and In Vivo Characterization of a Neutral Boron–Containing Thrombin Inhibitor", Mar. 5, 1993, pp. 4734–4741, vol. 268, No. 7, J. Bio. Chem.

Wolfram Bode et al, "The Refined 1.9 ø Crystal Structure of Human α–Thrombin: Interaction with D–Phe–Pro–Arg Chlormethylketone and Significance of the Tyr–Pro–Pro–Trp Insertion Segment", 1989, pp. 3467–3475, vol. 8, EMBO Journal.

S. Bajusz et al. " Peptide Aldehyde Inhibitors of the Fibrinogen–Thrombin Reaction,"pp. 603–608, Peptides : Chemistry, Structure & Biology, ® 1975, Ann Arbor Science Publishers.

John Dimaio et al. "Synthesis of A Homologous Series of Ketomethylene Arginyl Pseudodipeptides and Application to Low Molecular Weight Hirudin–kike Thrombin Inhibitors", 1992, pp. 3331–3341, J. Med. Chem.

J.M. Maraganore et al, "Design and Characterization of Hirulogs: A Novel Class of Bivalent Peptide Inhibitors of Thrombin", 1990, pp. 7095–7101, Biochemistry.

Fritz Markwardt, "Hirudin: The Promising Antithrombotic", 1992, pp. 211–232, vol. 10 No. 2, Cardio–Vascular Drug Reviews.

B. Blomback et al, "Synthetic Peptides with Anticoagulant and Vasodilating Activity", pp. 59–64, Scand. J. Clin. Lab. Inest. Suppl., 1969.

*Primary Examiner*—Mukund J. Shah
*Assistant Examiner*—Tamthom N. Truong
*Attorney, Agent, or Firm*—Foley & Lardner

[57] ABSTRACT

This invention relates to the discovery of heterocyclic competitive inhibitors of the enzyme thrombin, their preparation, and pharmaceutical compositions thereof. As well, this invention relates to the use of such compounds and compositions in vitro as anticoagulants and in vivo as agents for the treatment and prophylaxis of thrombotic disorders such as venous thrombosis, pulmonary embolism and arterial thrombosis resulting in acute ischemic events such as myocardial infarction or cerebral infarction. Moreover, these compounds and compositions have therapeutic utility for the prevention and treatment of coagulopathies associated with coronary bypass operations as well as restenotic events following transluminal angioplasty.

8 Claims, No Drawings

LOW MOLECULAR WEIGHT BICYCLIC THROMBIN INHIBITORS

This application is a continuation of PCT/CA 95/00708, filed Dec. 21, 1995.

FIELD OF THE INVENTION

This invention relates to compounds useful for the treatment of thrombotic disorders, and more particularly to novel heterocyclic inhibitors of the enzyme thrombin.

BACKGROUND

Inordinate thrombus formation on blood vessel walls precipitates acute cardiovascular disease states that are the chief cause of death in economically developed societies. Plasma proteins such as fibrinogen, proteases and cellular receptors participating in hemostatis have emerged as important factors that play a role in acute and chronic coronary disease as well as cerebral artery disease by contributing to the formation of thrombus or blood clots that effectively diminish normal blood flow and supply. Vascular aberrations stemming from primary pathologic states such as hypertension, rupture of artheroslerotic plaques or denuded endothelium, activate biochemical cascades that serve to respond and repair the injury site. Thrombin is a key regulatory enzyme in the coagulation cascade; it serves a pluralistic role as both a positive and negative feedback regulator. However, in pathologic conditions the former is amplified through catalytic activation of cofactors required for thrombin generation as well as activation of factor XIII necessary for fibrin cross-linking and stabilization.

In addition to its direct effect on hemostasis, thrombin exerts direct effects on diverse cell types that support and amplify pathogenesis of arterial thrombus disease. The enzyme is the strongest activator of platelets causing them to aggregate and release substances (eg. ADP $TXA_2$ NE) that further propagate the thrombotic cycle. Platelets in a fibrin mesh comprise the principal framework of a white thrombus. Thrombin also exerts direct effects on endothelial cells causing release of vasoconstrictor substances and translocation of adhesion molecules that become sites for attachment of immune cells. In addition, the enzyme causes mitogenesis of smooth muscle cells and proliferation of fibroblasts. From this analysis, it is apparent that inhibition of thrombin activity constitutes a viable therapeutic approach towards the attenuation of proliferative events associated with thrombosis.

The principal endogeneous neutralizing factor for thrombin activity in mammals is antithrombin III (ATIII), a circulating plasma macroglobulin having low affinity for the enzyme. Heparin exerts clinical efficacy in venous thrombosis by enhancing ATIII/thrombin binding through catalysis. However, heparin also catalyzes inhibition of other proteases in the coagulation cascade and its efficacy in platelet-dependent thrombosis is largely reduced or abrogated due to inaccessibility of thrombus-bound enzyme. Adverse side effects such as thrombocytopenia, osteoporosis and triglyceridemia have been observed following prolonged treatment with heparin.

Hirudin, derived from the glandular secretions of the leech *hirido medicinalis* is one of the high molecular weight natural anticoagulant protein inhibitors of thrombin activity (Markwardt F. Cardiovascular Drug Reviews, 10, 211, 1992). It is a biopharmaceutical that has demonstrated efficacy in experimental and clinical thrombosis. A potential drawback to the use of Hirudin as a therapeutic agent is likely antigenicity and lack of an effective method of neutralization, especially in view of its extremely tight binding characteristics toward thrombin. The exceedingly high affinity for thrombin is unique and is attributed to a simultaneous interaction with the catalytic site as well as a distal "anion binding exosite" on the enzyme.

Thrombin activity can also be abrogated by Hirudin-like molecules such as hirulog (Maraganore, J. M. et al., Biochemistry, 29, 7095, 1990) or hirutonin peptides (Di Maio, J. et al., J. Med. Chem., 35, 3331, 1992).

Thrombin activity can also be inhibited by low molecular weight compounds that compete with fibrinogen for thrombin's catalytic site, thereby inhibiting proteolysis of that protein or other protein substrates such as the thrombin receptor. A common strategy for designing enzyme inhibitory compounds relies on mimicking the specificity inherent in the primary and secondary structure of the enzyme's natural substrate. Thus, Blomback et al. first designed a thrombin inhibitor that was modeled upon the partial sequence of the fibrinogen Aα chain comprising its proteolytically susceptible region (Blomback, et al., J. Clin. Lab. Invest., 24, 59, 1969). This region of fibrinogen minimally includes the residues commencing with phenylalanine:

Ala-Asp-Ser-Gly-Glu-Gly-Asp-<u>Phe</u>-Leu-Ala-Glu-Gly

-Gly-Gly-Val-Arg-Gly-Pro-Arg
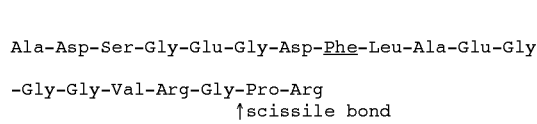

Systematic replacement of amino acids within this region has led to optimization of the tripeptidyl inhibitory sequence exemplified by the peptide (D)-Phe-Pro-Arg which corresponds to interactions within the $P_3$-$P_2$-$P_1$ local binding sites on thrombin (Bajusz S. et al. in Peptides: Chemistry Structure and Biology: Proceedings of the Fourth American Peptide Symposium, Walter R., Meienhofer J. Eds. Ann Arbor Science Publishers Inc., Ann Arbor, Mich., 1975, pp 603).

Bajusz et al. have also reported related compounds such as (D)Phe-Pro-Arg-(CO)H (GYKI-14166) and (D)MePhe-Pro-Arg-(CO)H (GYKI-14766) (Peptides-Synthesis, Structure and Function: Proceedings of the Seventh American Peptide Symposium, Rich, D. H. & Gross, E. eds., Pierce Chemical Company, 1981, pp. 417). These tripeptidyl aldehydes are effective thrombin inhibitors both in vitro and in vivo. In the case of both GYKI-14166 and GYKI-14766, the aldehyde group is presumed to contribute strongly to inhibitory activity in view of its chemical reactivity toward thrombin's catalytic $Ser_{195}$ residue, generating a hemiacetal intermediate.

Related work in the area of thrombin inhibitory activity has exploited the basic recognition binding motif engendered by the tripeptide (D)Phe-Pro-Arg while incorporating various functional or reactive groups in the locus corresponding to the putative scissile bond (i.e. $P_1$-$P_1$').

In U.S. Pat. No. 4,318,904, Shaw reports chloromethylketones (PPACK) that are reactive towards $Ser_{195}$ and $His_{57}$. These two residues comprise part of thrombin's catalytic triad (Bode, W. et al., EMBO Journal 8, 3467, 1989).

Other examples of thrombin inhibitors bearing the (D)Phe-Pro-Arg general motif are those incorporating COOH-terminal boroarginine variants such as boronic acids or boronates (Kettner, C. et al., J. Biol. Chem., 268, 4734, 1993).

Still other congeners of this motif are those bearing phosphonates (Wang, C-L J., Tetrahedron Letters, 33, 7667, 1992) and ###-Keto esters (Iwanowicz, E. J. et al., Bioorganic and Medicinal Chemistry Letters, 12, 1607, 1992).

Neises, B. et al. have described a trichloromethyl ketone thrombin inhibitor (MDL-73756) and Attenburger, J. M. et al. have revealed a related difluoro alkyl amide ketone (Tetrahedron Letters, 32, 7255, 1991).

Maraganore et al. (European 0,333,356; WO 91/02750; U.S. Pat. No. 5,196,404) disclose a series of thrombin inhibitors that incorporate the D-Phe-Pro- moiety and hypothesize that this preferred structure fits well within the groove adjacent to the active site of thrombin. Variations on these inhibitors are essentially linear or cyclic peptides built upon the D-Phe-Pro moiety.

Another series of patents and patent applications have described attempts to develop effective inhibitors against thrombosis by using alpha-ketoamides and peptide aldehyde analogs (EP 0333356; WO 93/15756; WO 93/22344; WO 94/08941; WO 94/17817).

Still others have focused their attention on peptides, peptide derivatives, peptide alcohols, or cyclic peptides as anti-thrombotic agents (WO 93/22344, EP 0276014; EP 0341607; EP 0291982). Others have examines amidine sulfonic acid moieties to achieve this same end (U.S. Pat. No. 4,781,866), while yet others have examined para or meta substituted phenylalanine derivatives (WO 92/08709; WO 92/6549).

A series of Mitsubishi patents and patent applications have disclosed apparently effective argininamide compounds for use as antithrombotic agents. The chemical structures described in these documents represent variations of side groups on the argininamide compound (U.S. Pat. No. 4,173,630; U.S. Pat. No. 4,097,591; CA 1,131,621; U.S. Pat. No. 4,096,255; U.S. Pat. No. 4,046,876; U.S. Pat. No. 4,097,472; CA 2,114,153).

Canadian patent applications 2,076,311 and 2,055,850 disclose cyclic imino derivatives that exhibit inhibitory effects on cellular aggregation.

Many of the examples cited above are convergent by maintaining at least a linear acyclic tripeptidyl motif consisting of an arginyl unit whose basic side chain is required for interaction with a carboxylate group located at the base of the $P_1$ specificity cleft in thrombin. Two adjacent hydrophobic groups provide additional binding through favourable Van der Waals interactions within a contiguous hydrophobic cleft on the enzyme surface designated the $P_3$-$P_2$ site.

One object of the present invention is to provide thrombin inhibitors that display inhibitory activity towards the target enzyme, thrombin.

A further object of the present invention is to provide thrombin inhibitors that display inhibitory activity towards the target enzyme thrombin and are provided for in a pharmacologically acceptable state.

Still a further object of the present invention is to provide for the use of heterocyclic thrombin inhibitors and formulations thereof as anticoagulant and thrombin inhibitory agents.

Yet a further object of the present invention is to provide for the use of heterocyclic thrombin inhibitors and formulations thereof for therapeutic treatment of various thrombotic maladies.

A further object of the present invention is a process for the synthesis of these low molecular weight thrombin inhibitors. The enzyme inhibitors of the present invention are encompassed by the structure of general Formula I.

SUMMARY OF THE INVENTION

The present invention provides for novel compounds that display thrombin inhibitory activity as reflected in formula I:

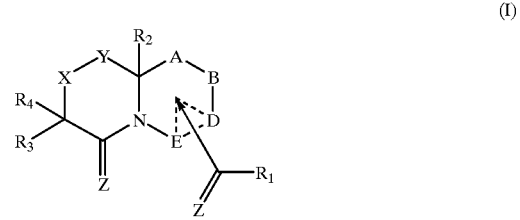

(I)

wherein:

A is selected from $(CH—R_8)_{0-1}$, S, SO, $SO_2$, O and $NR_8$ wherein $R_8$ is hydrogen, $C_{1-6}$ alkyl optionally interupted with 1 or 2 heteroatoms; $C_{6-16}$ aryl, $C_{3-7}$ cycloalkyl or heterocyclic ring or a hydrophobic group;

B is selected from S, $SO_2$, O, —N=, NH, —CH= and $CR_6R_7$ wherein $R_6$ and $R_7$ are independently selected from hydrogen and $C_{1-6}$ alkyl provided that when A is S, SO, $SO_2$, O, or $NR_8$, then B is $CR_6R_7$;

D is selected from $(CH—R_9)_{0-2}$, wherein $R_9$ is hydrogen, $C_{1-6}$ alkyl or —$C(O)R_1$; and CH with a double bond to B when B is —N= or —CH=;

E is selected from $CH_2$ and CH substituted with the —$C(O)R_1$, provided that only one of D and E is substituted with with —$C(O)R_1$;

X is selected from O, N—$R_5$, or CH—$R_5$;

Y is selected from O, S, SO, $SO_2$, N—$R_5$ and CH—$R_8$ provided that when X is N—$R_5$ then Y is CH—$R_8$ or O, and when X is O then Y is CH—$R_8$;

Z is selected from O, S and $H_2$;

$R_1$ is a polar amino acid residue arginyl moiety or an analog or derivative thereof optionally substituted with an amino acid, a peptide or a heterocycle;

$R_2$ is selected from H and $C_{1-6}$ alkyl optionally substituted with $C_6$ aryl, a 6 member heterocycle or a $C_{3-7}$ cycloalkyl ring;

$R_3$ is selected from H, $NR_6R_7$ and $C_{1-6}$ alkyl; and $R_4$ and $R_5$ are independently selected from H; $NR_6R_7$; $C_{6-16}$ aryl or $C_{3-7}$ cycloalkyl optionally substituted with $C_{1-6}$ alkyl; $C_{1-16}$ alkyl optionally interrupted by one or more heteroatom or carbonyl group and optionally substituted with OH, SH, $NR_6R_7$ or a $C_{6-16}$ aryl, heterocycle or $C_{3-7}$ cycloalkyl group optionally substituted with halogen, hydroxy, $C_{1-6}$ alkyl; an amino acid side chain; and a hydrophobic group.

As will be appreciated from the disclosure to follow, the molecules, compositions and methods of this invention are useful as anti-coagulants, or in the treatment and prevention of various diseases attributed to the undesirable effects of thrombin, as well as for diagnostic purposes.

DETAILED DESCRIPTION OF THE INVENTION

The present invention relates to molecules which inhibit the enzyme, thrombin. These molecules are characterized by a heterobicyclic moiety as illustrated in Formula I:

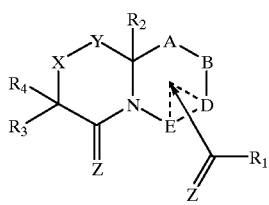

(I)

wherein X, Y, Z, A, B, D, E and $R_1$ to $R_4$ are as previously defined.

The term "hydrophobic group" (HG) as used hereinafter, refers to any group which lacks affinity for, or displaces water Hydrophobic groups include but are not limited to $C_{1-20}$alkyl, $C_{2-20}$alkenyl (e.g. vinyl, allyl) or $C_{2-20}$alkynyl (e.g. propargyl) optionally interrupted by a carbonyl group, (e.g. forming an acyl group); $C_{6-16}$aryl, $C_{3-7}$cycloalkyl, $C_{6-20}$aralkyl, $C_{6-20}$cycloalkyl substituted $C_{1-20}$alkyl, wherein the aliphatic portion is optionally interrupted by a carbonyl group (e.g. forming an acyl group) and the ring portion is optionally substituted with $C_{1-6}$alkyl such as methyl ethyl or t-butyl; or a hydrophobic amino acid side chain. Preferred hydrophobic groups include cyclohexyl, benzyl, benzoyl, phenylmethyl, phenethyl and para-t-butyl-phenylmethyl.

The term "arginyl moiety" represents an arginine amino acid residue or an analogue or derivative thereof. For example, an analogue or derivative of the natural residue may incorporate a longer or shorter methylene chain from the alpha carbon (i.e. ethylene or butylene chain); replacement of the guanidino group with a hydrogen bond donating or accepting group (i.e. amino, amidino or methoxy); replacement of the methylene chain with a constrained group (i.e. an aryl, cycloalkyl or heterocyclic ring); elimination of the terminal carboxyl (i.e. des-carboxy) or hydroxyl (i.e. an aldehyde); or a combination thereof.

The term "alkyl" represents a straight or branched, saturated or unsaturated chain having a specified total number of carbon atoms.

The term "aromatic" or "aryl" represents an unsaturated carbocyclic ring(s) or 6 to 16 carbon atoms which is optionally mono- or di-substituted with OH, SH, amino (i.e. $NR_6R_7$) halogen or $C_{1-6}$alkyl. Aromatic rings include benzene, napththalene, phenanthrene and anthracene. Preferred aromatic rings are benzene and naphthalene.

The term "cycloalkyl" represents a saturated carbocyclic ring of 3 to 7 carbon atoms which is optionally mono- or di-substituted with OH, SH, amino (i.e. $NR_6R_7$) halogen or $C_{1-6}$alkyl. Cycloalkyl groups include cyclo- propyl, butyl, pentyl, hexyl and heptyl. A preferred cycloalkyl group is cyclohexyl.

The term "aralkyl" represents a substituent comprising an aryl moiety attached via an alkyl chain (e.g. benzyl, phenethyl) wherein the sum total of carbon atoms for the aryl moiety and the alkyl chain is as specified. The aryl or chain portion of the group is optionally mono- or di-substituted with OH, SH, amino (i.e. $NR_6R_7$) halogen or $C_{1-6}$alkyl The term "heteroatom" as used herein represents oxygen, nitrogen or sulfur (O, N or S) as well as sulfoxyl or sulfonyl (SO or $SO_2$) unless otherwise indicated. It is understood that alkyl chains interrupted by one or more heteroatoms means that a carbon atom of the chain is replaced with a heteroatom having the appropriate valency. Preferrably, an alkyl chain is interrupted by 0 to 4 heteroatoms and that two adjacent carbon atoms are not both replaced.

The term "heterocycle" represents a saturated or unsaturated mono- or polycyclic (i.e. bicyclic) ring incorporating 1 or more (i.e. 1–4) heteroatoms selected from N, O and S. It is understood that a heterocycle is optionally mono- or di-substituted with OH, SH, amino (i.e. $NR_6R_7$), halogen, $CF_3$, oxo or $C_{1-6}$alkyl. Examples of suitable monocyclic heterocycles include but are not limited to pyridine, piperidine, pyrazine, piperazine, pyrimidine, imidazole, thiazole, oxazole, furan, pyran and thiophene. Examples of suitable bicyclic heterocycles include but are not limited to indole, quinoline, isoquinoline, purine, and carbazole.

The term "hydrophobic amino acid" represents an amino acid residue that bears an alkyl or aryl group attached to the α-carbon atom. Thus glycine, which has no such group attached to the α-carbon atom is not a hydrophobic amino acid. The alkyl or aryl group can be substituted, provided that the substituent or substituents do not detract from the overall hydrophobic character of the amino acid. Examples of hydrophobic amino acids include natural amino acid residues such as alanine; isoleucine; leucine; phenylalanine; and non-naturally ocurring amino acids such as those described in "The Peptides", vol. 5, 1983, Academic Press, Chapter 6 by D. C. Robers and F. Vellaccio. Suitable non-naturally ocurring amino acids include cyclohexylalanine and 1-aminocyclohexane-carboxylic.

By "amino acid chain" is meant the substituent attached to the carbon which is α to the amino group. For example, the side chain of the amino acid alanine is a methyl group and while benzyl is the side chain for phenylalanine.

Preferably $R_2$ is H or $C_{1-6}$alkyl. More preferably $R_2$ is H, methyl or ethyl and most preferably $R_2$ is H.

Preferably, $R_3$ is H or $C_{1-6}$alkyl. More preferably, $R_3$ is H, methyl or ethyl, and most preferably $R_3$ is H.

Preferably, one of $R_4$ or $R_5$ is a hydrophobic group such as a saturated or unsaturated carbocycle of 5 or 6 members optionally fused to another carbocyclic group while the other is H, $C_{1-16}$alkyl optionally substituted by $NR_6R_7$ or carboxy. The hydrophobic moiety may be linked via a spacer such as a $C_{1-16}$alkyl chain optionally interrupted with 1 or more (i.e. 1–4) heteroatoms, carbonyl or sulfonyl ($SO_2$) groups. More preferably, one of $R_4$ and $R_5$ is phenyl, cyclohexyl, indole, thienyl, quinoline, tetrahydroisoquinoline, naphthyl or benzodioxolane linked via $C_{1-16}$alkyl optionally interupted with a heteroatom or a carbonyl while the other is H, carboxymethyl or carboxyethyl.

Preferably, A is absent or $CH_2$.
Preferably, B is S or $CH_2$.
Preferably, D is $CH_2$.
Preferably, E is CH substituted with $—C(O)R_1$ wherein $R_1$ is as previously defined.
Preferably, X is CH—$R_5$ or N—$R_5$.
Preferably, Y is CH—$R_8$ or S.
Preferably, Z is O.

In a preferred embodiment, $R_1$ is represented by one of formula VIa to VId:

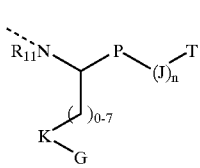

VIa

-continued

VIb
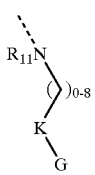

VIc
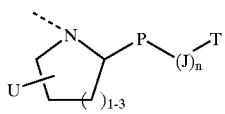

VId
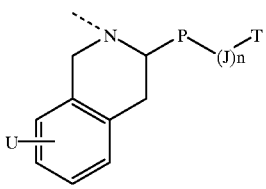

wherein:
$R_{11}$ is hydrogen or $C_{1-6}$alkyl;
K is a bond or —NH—;
G is $C_{1-4}$alkoxy; cyano; —NH$_2$; —CH$_2$—NH$_2$; —C(NH)—NH$_2$; —NH—C(NH)—NH$_2$; —CH$_2$—NH—C(NH)—NH$_2$; a $C_6$cycloalkyl or aryl substituted with cyano, —NH$_2$, —CH$_2$'NH$_2$, —C(NH)—NH$_2$, —NH—C(NH)—NH$_2$ or —CH$_2$—NH—C(NH)—NH$_2$; or a 5 or 6 member, saturated or unsaturated heterocycle optionally substituted with cyano, —NH$_2$, —CH$_2$—NH$_2$, —C(NH)—NH$_2$, —NH—C(NH)—NH$_2$ or —CH$_2$—NH—C(NH)—NH$_2$;
U is cyano, —NH$_2$, —C(NH)—NH$_2$ or —NH—C(NH)13 NH$_2$;
P is a bond, —C(O)— or a bivalent group:

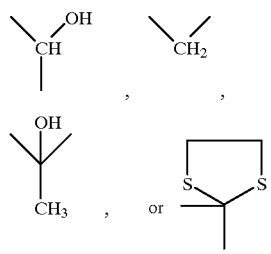

J is $C_{1-6}$alkylene optionally substituted with OH, NH$_2$ and $C_{1-6}$alkyl and optionally interrupted by a heteroatom selected from O, S and N;
n is 0 or 1; and
T is H, OH, amino, a peptide chain, $C_{1-16}$alkyl, $C_{1-16}$alkoxy, $C_{6-20}$aralkyl, or heterocycle optionally substituted.
Preferably $R_{11}$ is H or methyl and most preferably H.
Preferably K is a bond.
Preferably G is —NH—C(NH)—NH$_2$ attached via a methylene chain of 3–7 carbons or phenyl substituted with —C(NH)—NH$_2$ attached via a methylene chain of 0 to 3 carbons. More preferably G —NH—C(NH)—NH$_2$ attached via a methylene chain of 3 atoms.
Preferably P is —C(O)—.
Preferably J is selected from: —CH$_2$—S—CH$_2$—CH$_2$—; —CH$_2$—O—CH$_2$—CH$_2$—; —CH$_2$—NH—CH$_2$—CH$_2$—; and a bond when n is 0. More preferably, J is a bond while n is 0.

In particular embodiments of the invention, $R_1$ is selected from the following amino acid derivatives prepared according to the procedures described in Bioorg. Med. Chem., 1995, 3:1145:

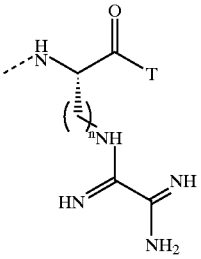 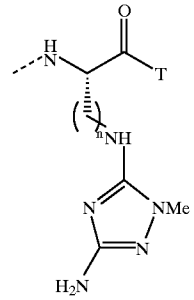

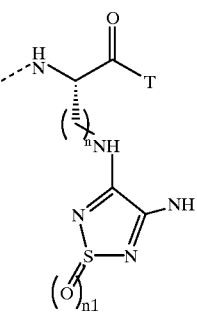 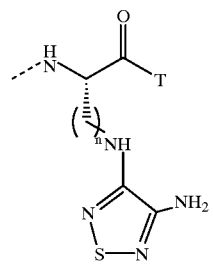

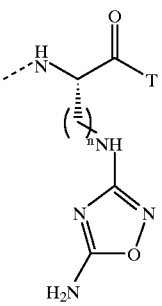 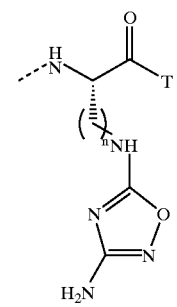

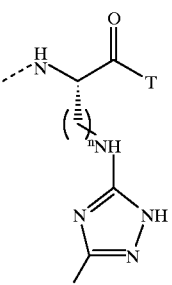 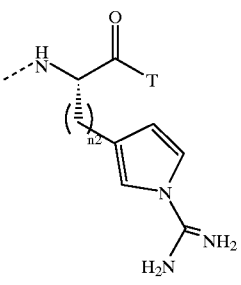

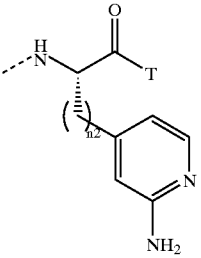 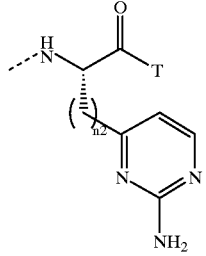

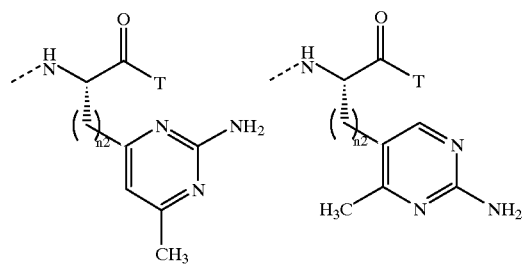
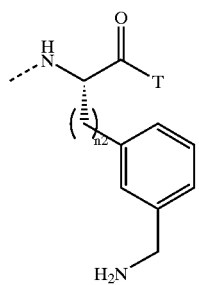
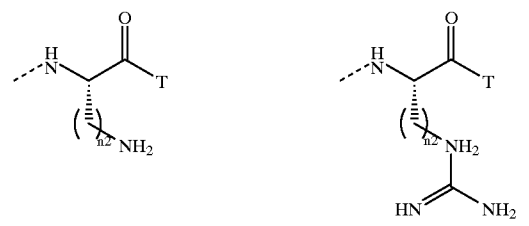
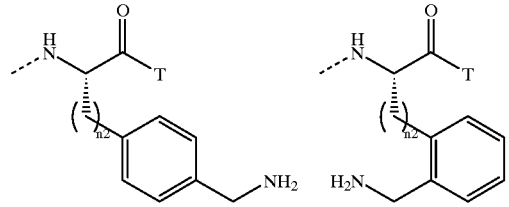
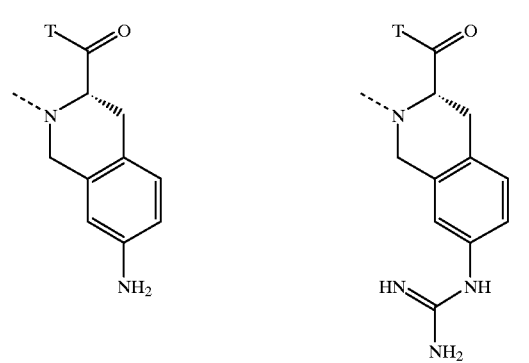
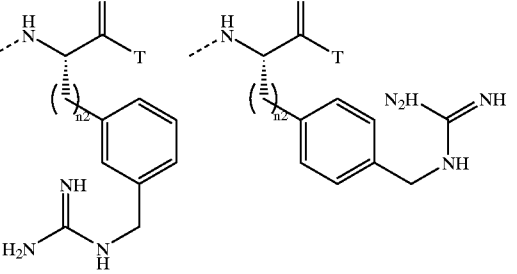
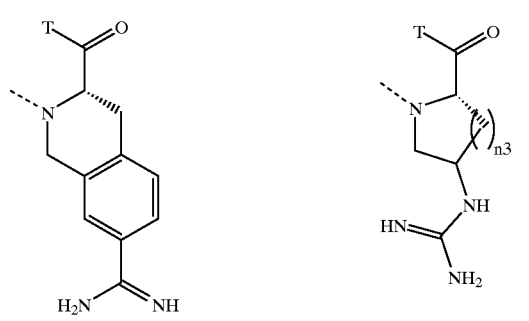
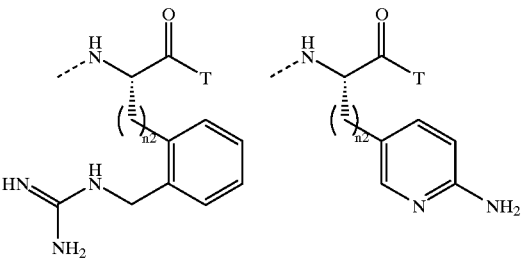
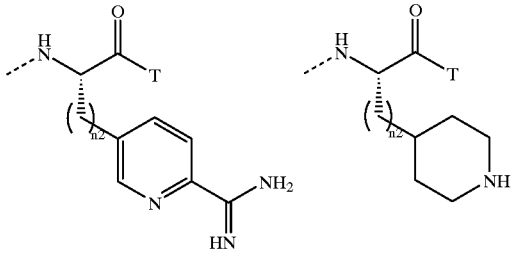
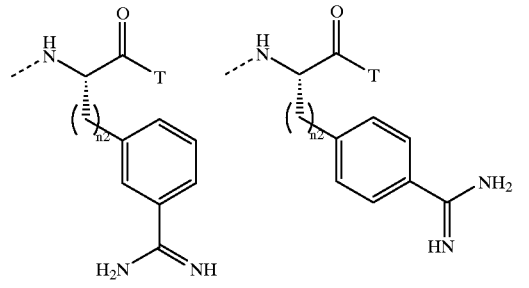
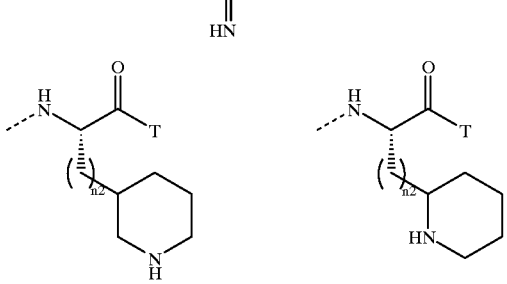

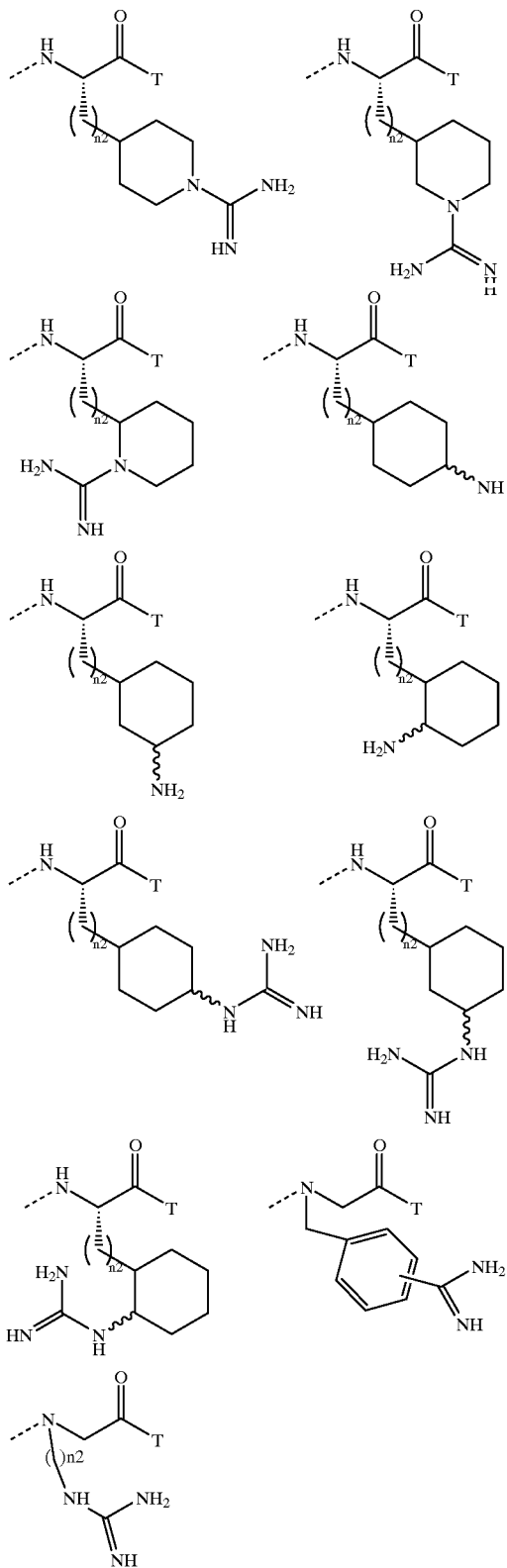

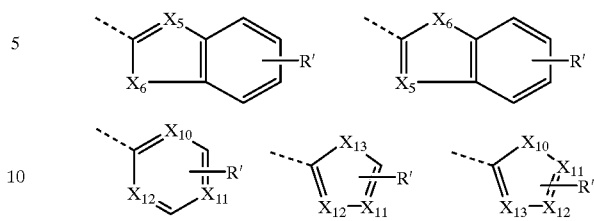

wherein $X_5$, $X_{10}$, $X_{11}$ and $X_{12}$ are each independently selected from the group consisting of N, or C—$X_7$ where $X_7$ is hydrogen, $C_{1-4}$alkyl, or $C_{6-16}$aryl;

$X_6$ and $X_{13}$ are each independently selected from the group consisting of C, O, N, S, N—$X_7$, or CH—$X_7$;

R' is hydrogen, $C_{1-16}$alkyl optionally carboxyl substituted, carboxyl, —$C_{0-16}$alkyl—$CO_2$—$C_{1-16}$alkyl, $C_{6-20}$aralkyl, $C_{3-7}$cycloalkyl, aryl or an aromatic heterocycle.

Preferably T is selected from the group consisting of:

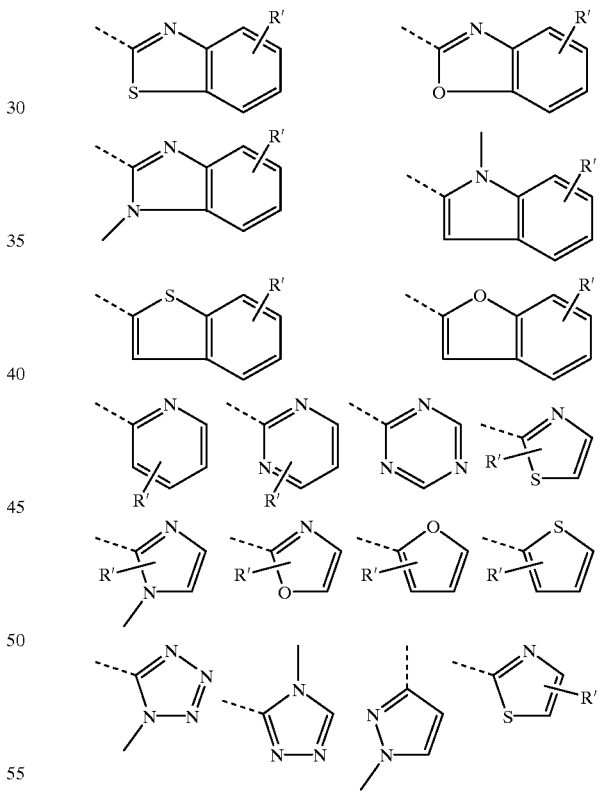

wherein R' is as defined above.

More preferably T is selected from the group consisting of:

wherein n=1–6, n1=1–2, n2=0–7 and T is as previously defined.

In a preferred embodiment, T is a peptide of 1 to 4 amino acid residues in length and preferably fibrinogen's A or B chain or fragment or derivative thereof. In another preferred embodiment, T is a heterocycle selected from the group consisting of:

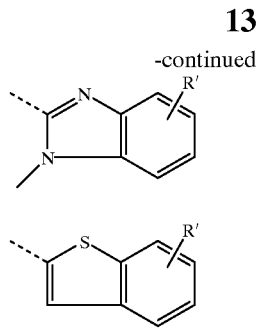

wherein R' is as defined above.

More preferably T is selected from the group consisting of:

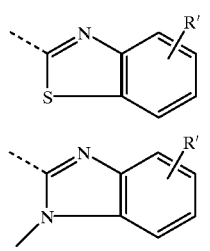

wherein R' is as defined above.

Most preferably T is

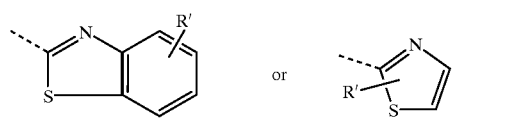

wherein R' is H or $C_{1-4}$alkyl such as methyl, ethyl, propyl or butyl and most preferably wherein R' is hydrogen,. In another embodiment, T is a 1,2 thiazole optionally substituted with R' and∃or is attached to J at the 2, 3, 4 or 5 position of the ring.

In particular embodiments, compounds of the invention are represented by formulas II, III, IV and V, wherein X, Y, B, $R_1$ to $R_4$ and $R_8$ are as previously defined.

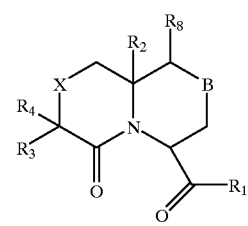

(II)

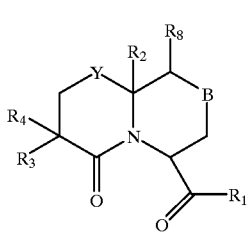

(III)

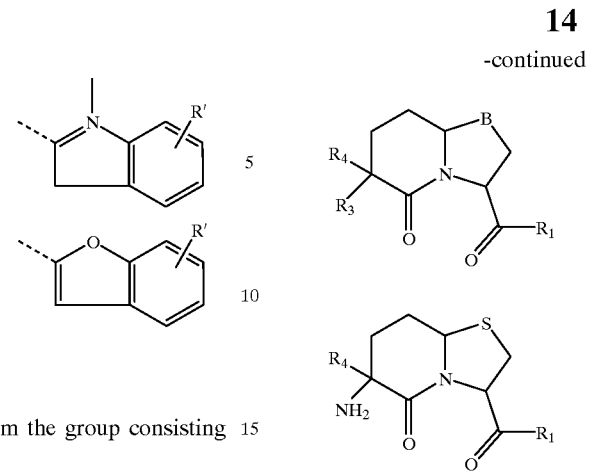

(IV)

(V)

In a particularly preferred embodiment, compounds of the invention are represented by one of formulas VII, VIII, IX and X:

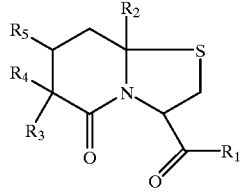

(VII)

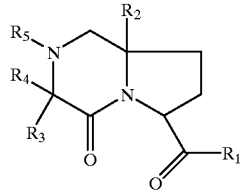

(VIII)

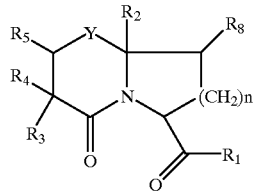

(IX)

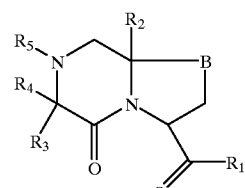

(X)

wherein

B is O, S, —$CH_2$—, or —NH—;

Y is selected from O, S, SO, $SO_2$, N—$R_5$ and CH—$R_8$;

$R_1$ is an arginyl moiety or an analog or derivative thereof optionally substituted with an amino acid, a peptide or a heterocycle;

$R_2$ is H or $C_{1-6}$alkyl;

$R_3$ is selected from H, $NR_6R_7$ and $C_{1-6}$alkyl; and $R_4$ and $R_5$ are independently selected from H; $NR_6R_7$; $C_{6-16}$aryl or $C_{3-7}$cycloalkyl optionally substituted with $C_{1-6}$alkyl; $C_{1-16}$alkyl optionally interrupted by one or more heteroatom or carbonyl group and optionally substituted with OH, SH, $NR_6R_7$ or a $C_{6-16}$aryl, heterocycle or $C_{3-7}$cycloalkyl group optionally substituted with halogen, hydroxyl, $C_{1-6}$alkyl; an amino acid side chain; and a hydrophobic group;

$R_8$ is hydrogen, $C_{1-6}$alkyl optionally interupted with 1 or 2 heteroatoms; $C_{6-16}$aryl, $C_{3-7}$cycloalkyl or heterocyclic ring or a hydrophobic group; and n is 1 or 2.

Preferred compounds according to formula VII include:

0005  6S-benzylhexahydro-5-oxo-5H-thiazolo[3,2-a]pyridine-3R-carboxamido (propyl ketoarginine)

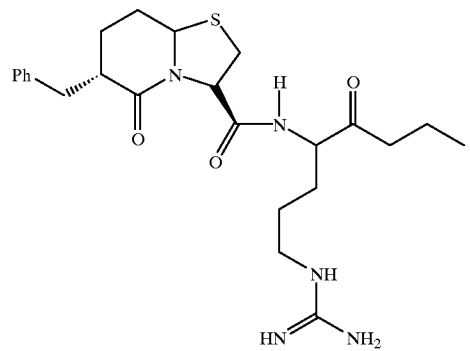

0010  6S-benzylhexahydro-5-oxo-5H-thiazolo[3,2-a]pyridine-3R-carboxamido (butyl ketoarginine)

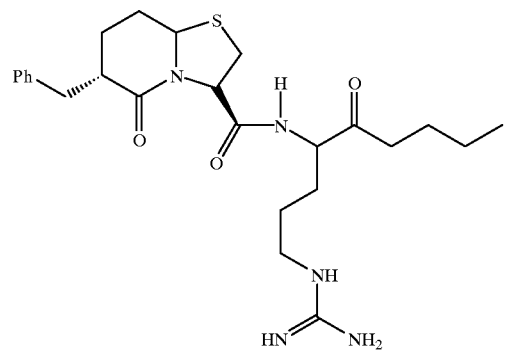

0015  6S-benzylhexahydro-5-oxo-5H-thiazolo[3,2-a]pyridine-3R-carboxamido(propylcarbmethoxyketoarginine)

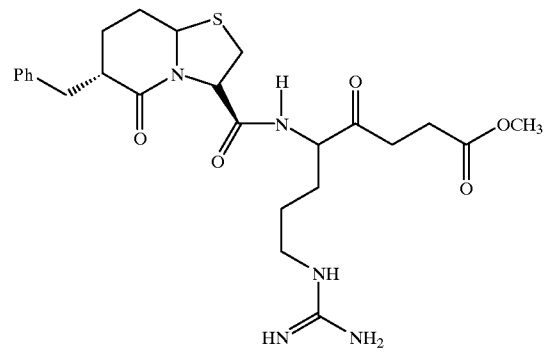

-continued 0020 6S-cyclohexymethyl hexahydro-5-oxo-5H-thiazolo[3,2-a]pyridine-3R-carboxamido(benzylketo arginine)

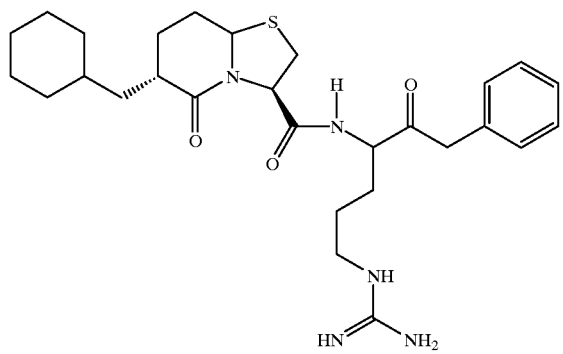

0025 6S-cyclohexyl methyl hexahydro-5-oxo-5H-thiazolo[3,2-a]pyridine-3R-carboxamido(carbmethoxy propyl cyclodithioketalarginine)

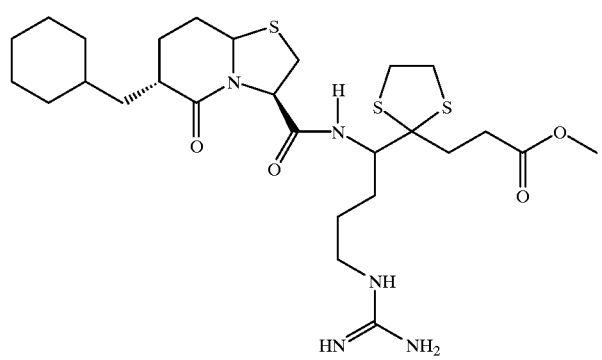

0030 6S-cyclohexylmethyl hexahydro-5-oxo-5H-thiazolo[3,2-a]pyridine-3R-carboxamido((S)-Arg-(R)-pipecolilic acid)

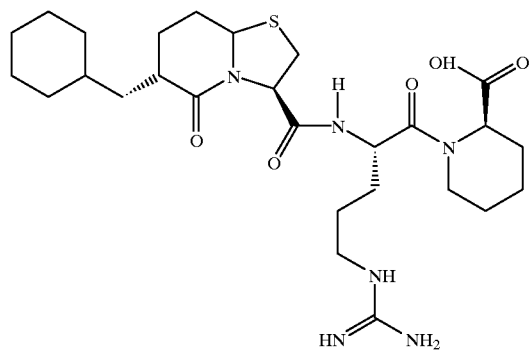

0035 6S-benzylhexahydro-5-oxo-5H-thiazolo[3,2-a]pyridine-3R-carboxamido(carboxamidopropyl cyclodithioketal arginine)

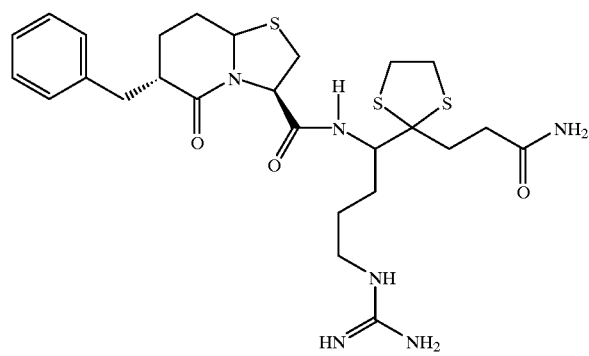

-continued 0040 6S-cyclohexylmethylhexahydro-5-oxo-5H-thiazolo[3,2-a]pyridine-3R-carboxamido((S)-Arg nipecotamide)

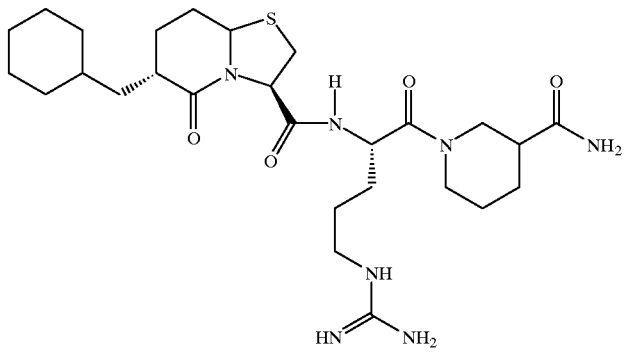

0045 6S-cyclohexylmethylhexahydro-5-oxo-5H-thiazolo[3,2-a]pyridine-3R-carboxamido((S)Arg isonipecotamide)

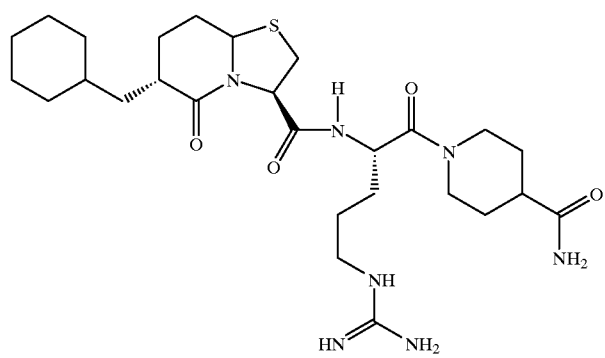

0050 6S-benzylhexahydro-5-oxo-5H-thiazolo[3,2-a]pyridine-3R-carboxamido(carboxamidopentyl cyclodithioketal arginine)

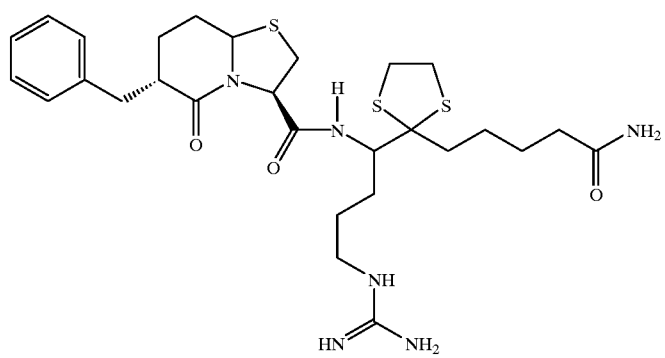

0055 6S-benzylhexahydro-5-oxo-5H-thiazolo[3,2-a]pyridine-3R-carboxamido(carbmethoxy propyl cyclodithioketal arginine)

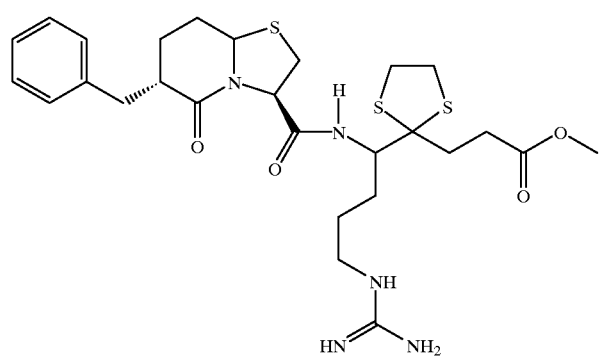

-continued
0060 6S-cyclohexylmethylhexahydro-5-oxo-5H-thiazolo[3,2-a]pyridine-3R-carboxamido(1-carboxy-3-thiobutyl ketoarginine)
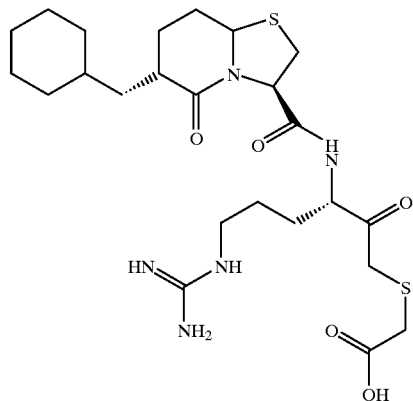
0065 6S-cyclohexylmethylhexahydro-5-oxo-5H-thiazolo[3,2-a]pyridine-3R-carboxamido(1-carboxy-3-thiobutyl ketoarginine)
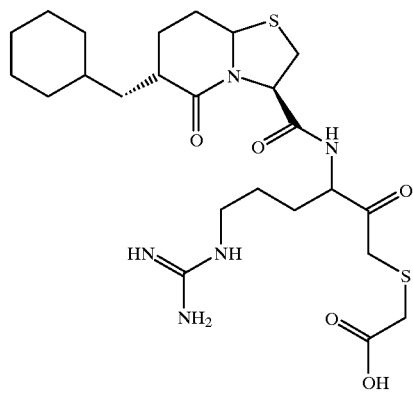
0070 6S-cyclohexylmethylhexahydro-5-oxo-5H-thiazolo[3,2-a]pyridine-3R-carboxamido(1-carboxy-2-methyl-3-thiobutyl ketoarginine)
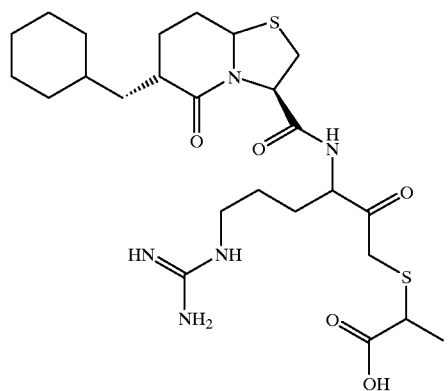

0075 6S-cyclohexylmethylhexahydro-5-oxo-5H-thiazolo[3,2-a]pyridine-3R-carboxamido((3-thiobutyl sulfonic acid) ketoarginine)
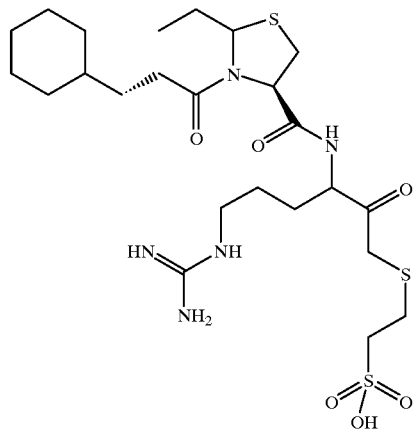
0080 6S-cyclohexylmethylhexahydro-5-oxo-5H-thiazolo[3,2-a]pyridine-3R-carboxamido(iso-quinolinium methyl ketoarginine)
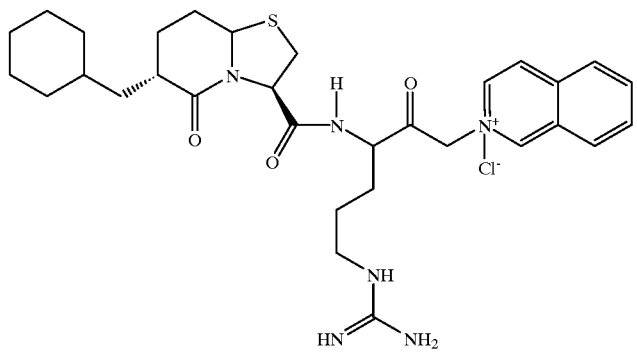
0085 6S-cyclohexylmethylhexahydro-5-oxo-5H-thiazolo[3,2-a]pyridine-3R-carboxamido(propylcarbmethoxy ketoarginine)
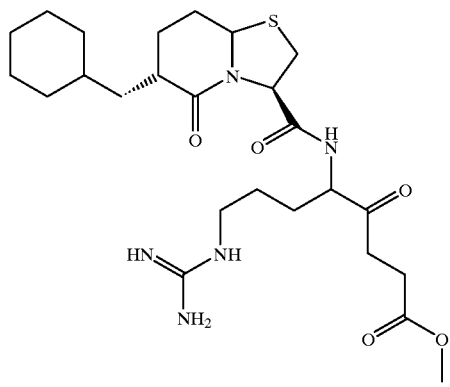

| | | |
|---|---|---|
| 0090 | 6S-cyclohexylmethylhexahydro-5-oxo-5H-thiazolo[3,2-a]pyridine-3R-carboxamido((propylketo)Arg—Phe—Arg—NH₂) | 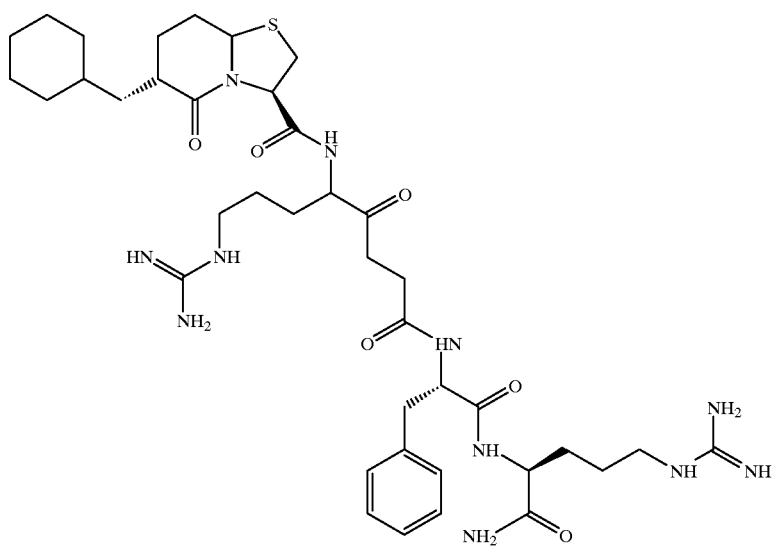 |
| 0095 | 6S-benzylhexahydro-5-oxo-5H-thiazolo[3,2-a]pyridine-3R-carboxamido((propanoic acid) ketoarginine) | 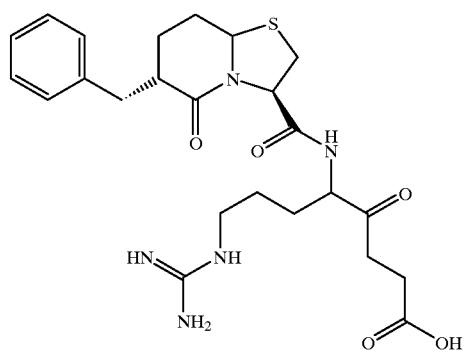 |
| 0100 | 6S-benzylhexahydro-5-oxo-5H-thiazolo[3,2-a]pyridine-3R-carboxamido(propyl carbmethoxy ketoarginine) | 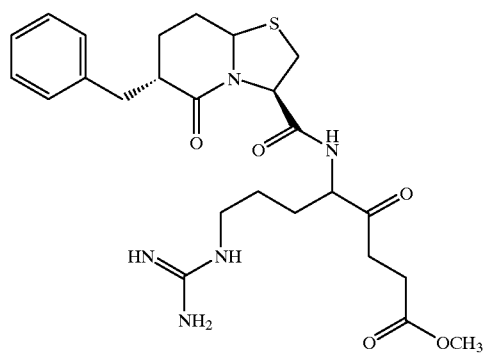 |
| 0105 | 6S-cyclohexylmethylhexahydro-5-oxo-5H-thiazolo[3,2-a]pyridine-3R-carboxamido (α-benzothiazolo keto arginine); and | 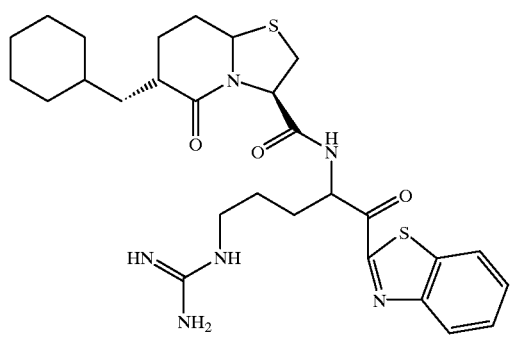 |

-continued

| | | |
|---|---|---|
| 0110 | 6S-cyclohexylpropylhexahydro-5-oxo-5H-thiazolo[3,2-a]pyridine-3R-carboxamido(propylcarbmethoxy ketoarginine) | 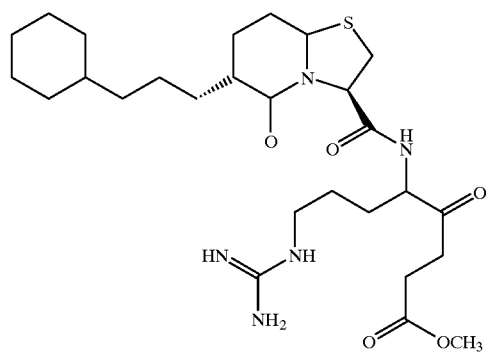 |
| 0205 | 6-Benzyl-5-oxo-hexahydro-thiazolo[3,2-a]pyridine-3-carboxylic acid[1-(benzothiazole-2-carbonyl)-4-guanidino-butyl]-amide | 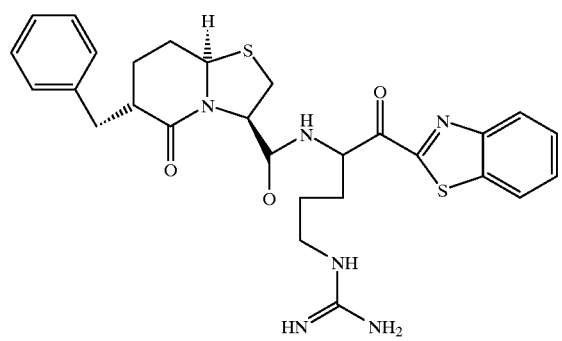 |
| 0210 | 6-Benzyl-5-oxo-hexahydro-thiazolo[3,2-a]pyridine-3-carboxylic acid[1-(benzothiazole-2-carbonyl)-4-guanidino-butyl]-amide | 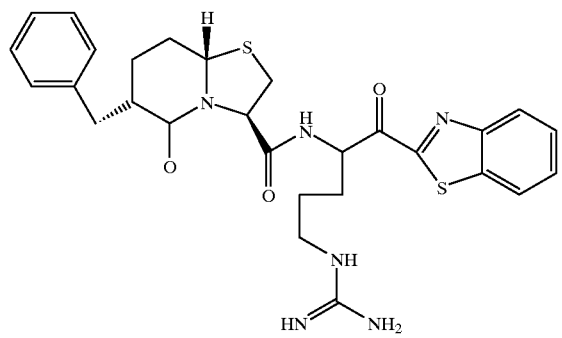 |
| 0215 | 6-Benzyl-5-oxo-hexahydro-thiazolo[3,2-a]pyridine-3-carboxylic acid[1-(benzothiazole-2-carbonyl)-4-guanidino-butyl]-amide | 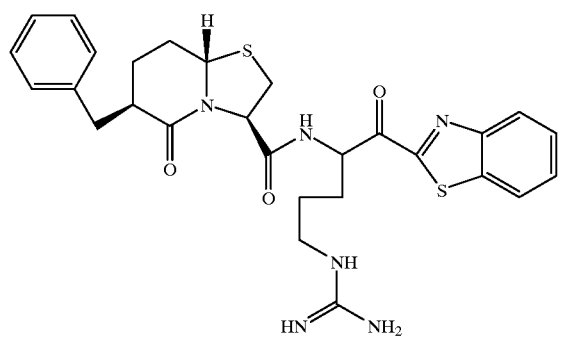 |

-continued

| | | |
|---|---|---|
| 0220 | 6-Benzyl-8a-methyl-5-oxo-hexahydro-thiazolo[3,2-a]pyridine-3-carboxylic acid[1-(benzothiazole-2-carbonyl)-4-guanidino-butyl]-amide | 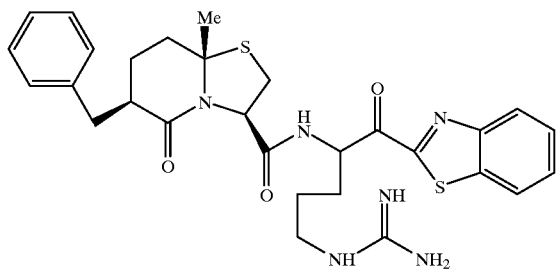 |
| 0225 | 8a-Methyl-5-oxo-6-phenethyl-hexahydro-thiazolo[3,2-a]pyridine-3-carboxylic acid[1-(benzothiazole-2-carbonyl)-4-guanidino-butyl]-amide | 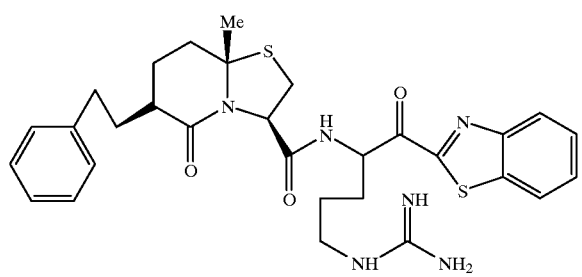 |
| 0230 | 8a-Methyl-5-oxo-6-phenethyl-hexahydro-thiazolo[3,2-a]pyridine-3-carboxylic acid[1-(benzothiazole-2-carbonyl)-4-guanidino-butyl]-amide | 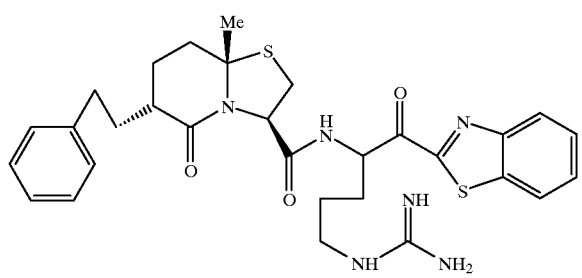 |
| 0240 | 8a-Methyl-5-oxo-6-(2-trifluoro methyl-quinolin-6-ylmethyl)-hexahydro-thiazolo[3,2-a]pyridine-3-carboxylic acid[1-(benzothiazole-2-carbonyl)-4-guanidino-butyl]-amide | 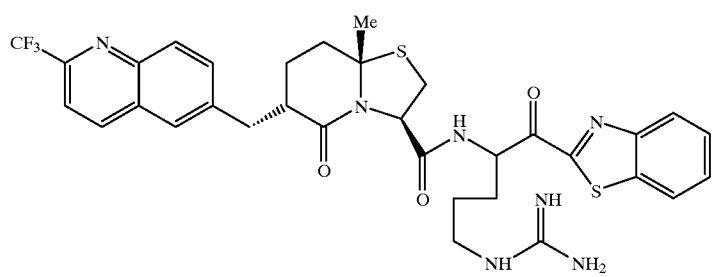 |
| 0245 | 6-Benzyl-5-oxo-hexahydro-thiazolo[3,2-a]pyridine-3-carboxylic acid[4-guanidino-1-(thiazole-2-carbonyl)butyl]-amide | 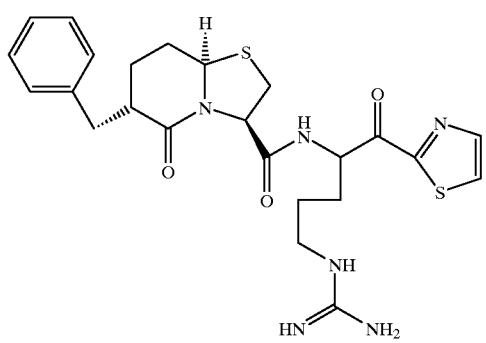 |

-continued

| | | |
|---|---|---|
| 0250 | 6-Benzyl-5-oxo-hexahydro-thiazolo[3,2-a]pyridine-3-carboxylic acid[4-guanidino-1-(thiazole-2-carbonyl)butyl]-amide | 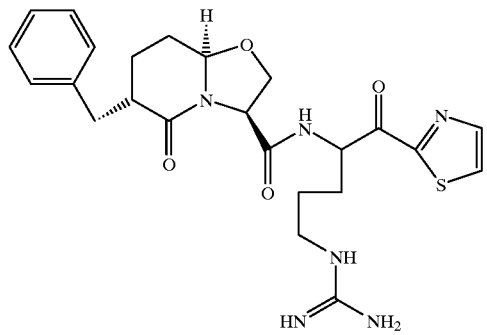 |
| 0255 | 6-Benzyl-5-oxo-hexahydro-thiazolo[3,2-a]pyridine-3-carboxylic acid[4-guanidino-1-(1-methyl-1H imidazole-2-carbonyl)butyl]-amide | 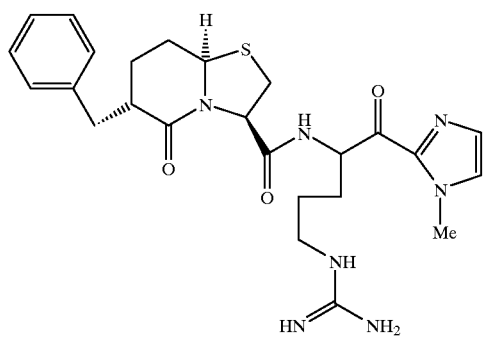 |
| 0260 | 6-Benzyl-8a-methyl-5-oxo-hexahydro-thiazolo[3,2-a]pyridine-3-carboxylic acid[4-guanidino-1-(thiazole-2-carbonyl)-butyl]-amide | 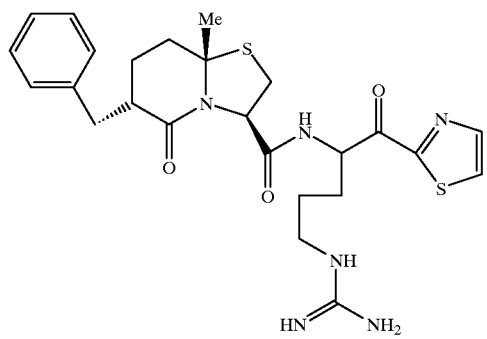 |
| 0265 | 5-Oxo-6-(3-cyclohexyl-propyl)-hexahydro-thiazolo[3,2-a]pyridine-3-carboxylic acid[4-guanidino-1-(thiazole-2-carbonyl)butyl]-amide | 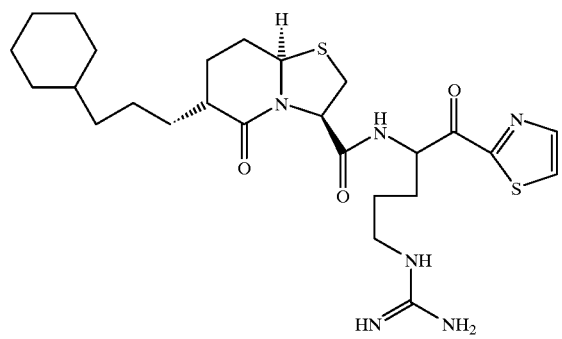 |

-continued

| | | |
|---|---|---|
| 0275 | 8a-Methyl-5-oxo-6-(3-phenyl-propyl)-hexahydro-thiazolo[3,2-a]pyridine-3-carboxylic acid[4-guanidino-1-(thiazole-2-carbonyl)-butyl]-amide | 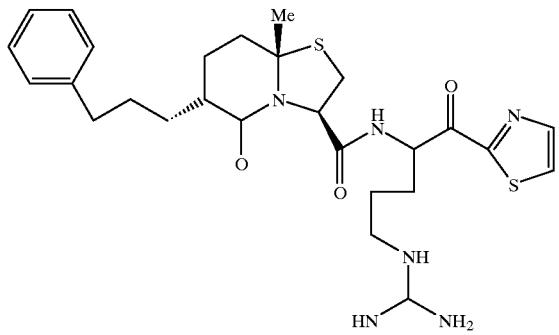 |
| 0280 | 8a-Methyl-5-oxo-6-(3-phenyl-propyl)-hexahydro-thiazolo[3,2-a]pyridine-3-carboxylic acid[4-guanidino-1-(thiazole-2-carbonyl)-butyl]-amide | 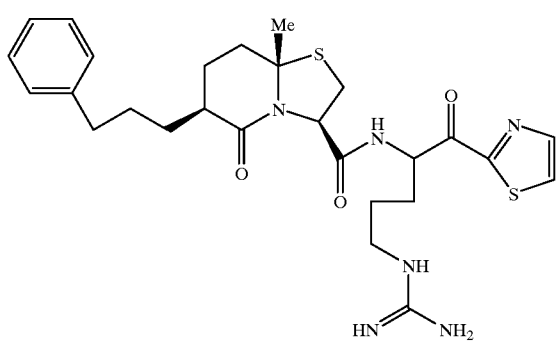 |
| 0285 | 8a-Methyl-5-oxo-6-(2-trifluoromethyl-quinolin-6-ylmethyl)-hexahydro-thiazolo[3,2-a]pyridine-3-carboxylic acid[4-guanidino-1-(thiazole-2-carbonyl)-butyl]-amide | 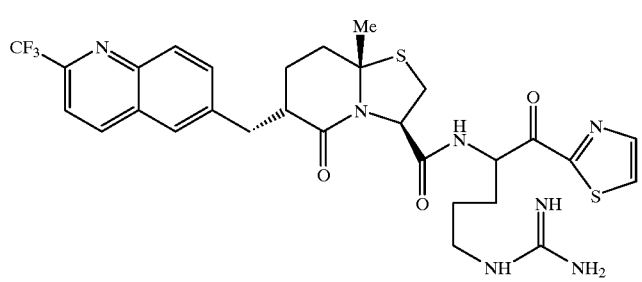 |
| 0295 | 6-(1,3-Dioxo-1,3-dihydro-isoindol-2-yl)-5-oxo-hexahydro-thiazolo[3,2-a]pyridine-3-carboxylic acid[4-guanidino-1-(thiazole-2-carbonyl)-butyl]-amide | 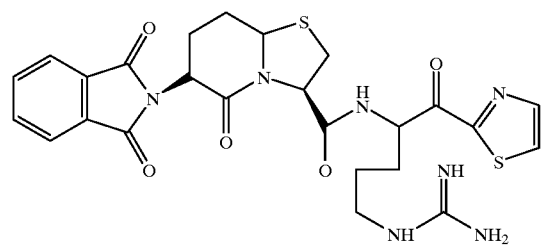 |
| 0305 | 5-Oxo-6-(3-phenyl-propionyl amino)-hexahydro thiazolo[3,2-a]pyridine-3-carboxylic acid[4-guanidino-1-(thiazole-2-carbonyl)-butyl]-amide | 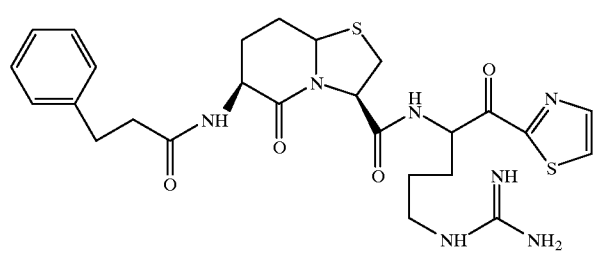 |

| | |
|---|---|
| 0315 5-Oxo-6-(3-phenyl-propionyl amino)-hexahydro thiazolo[3,2-a]pyridine-3-carboxylic acid[4-guanidino-1-(thiazole-2-carbonyl)-butyl]-amide | 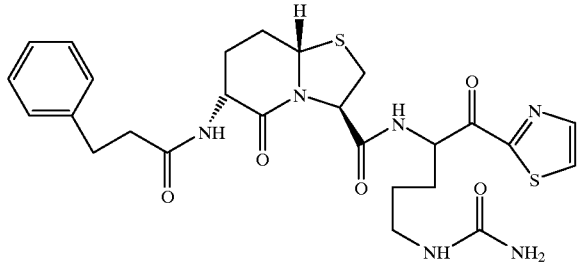 |

More preferred compounds according to formula (VII) include:

0085 6S-cyclohexylmethylhexahydro-5-oxo-5H-thiazolo[3,2-a]pyridine-3R-carboxamido(propylcarbo methoxyketoarginine);

0090 6S-cyclohexylmethylhexahydro-5-oxo-5H-thiazolo[3,2-a]pyridine-3R-carboxamido((propylketo)Arg-Phe-Arg-NH$_2$);

0095 6S-benzylhexahydro-5-oxo-5H-thiazolo[3,2-a]pyridine-3R-carboxamido((propanoic acid) ketoarginine);

0105 6S-cyclohexylmethylhexahydro-5-oxo-5H-thiazolo[3,2-a]pyridine-3R-carboxamido (α-benzothiozolo keto arginine);

0210 6-Benzyl-5-oxo-hexahydro-thiazolo[3,2-a]pyridine-3-carboxylic acid [1-(benzothiazole-2-carbonyl)-4-guanidino-butyl]-amide;

0220 6-Benzyl-8a-methyl-5-oxo-hexahydro-thiazolo[3,2-a]pyridine-3-carboxylic acid [1-(benzothiazole-2-carbonyl)-4-guinidino-butyl]-amide; 0240 8a-Methyl-5-oxo-6-(2-trifluoromethyl-quinolin-6-ylmethyl)-hexahydro-thiazolo[3,2-a]pyridine-3-carboxylic acid [1-(benzothiazole-2-carbonyl)-4-guinidino-butyl]-amide;

0245 6-Benzyl-5-oxo-hexahydro-thiazolo[3,2-a]pyridine-3-carboxylic acid [4-guinidino-1-(thiazole-2-carbonyl) butyl]-amide;

0260 6-Benzyl-8a-methyl-5-oxo-hexahydro-thiazolo[3,2-a]pyridine-3-carboxylic acid [4-guinidino-1-(thiazole-2-carbonyl)-butyl]-amide;

0265 5-(Oxo-6-(3-cyclohexyl-propyl)-hexahydro-thiazolo[3,2-a]pyridine-3-carboxylic acid [4-guianidino-1-(thiazole-2-carbonyl)butyl]-amide;

0285 8a-Methyl-5-oxo-6-(2-trifluoromethyl-quinolin-6-ylmethyl)-hexahydro-thiazolo[3,2-a]pyridine-3-carboxylic acid [4-guianidino-1-(thiazole-2-carbonyl)-butyl]-amide; and 0315 5-Oxo-6-(3-phenyl-propylonylamino)-hexahydro thiazolo[3,2-a]pyridine-3-carboxylic acid [4-guinidino-1-(thiazole-2-carbonyl)-butyl]-amide.

Most preferred compounds according to formula VII include:

0085 6S-cyclohexylmethylhexahydro-5-oxo-5H-thiazolo[3,2-a]pyridine-3R-carboxamido(propylcarbo methoxy ketoarginine); and 0105 6S-cyclohexylmethylhexahydro-5-oxo-5H-thiazolo[3,2-a]pyridine-3R-carboxamido (α-benzothiozolo keto arginine).

Preferred compounds according to formula VIII include:

| | |
|---|---|
| 0325 3-Aminomethyl-2-benzoyl-4-oxo-octahydro-pyrrolo[1,2-a]pyridine-6-carboxylic acid[1-(benzothiazole-2-carbonyl)-4-guanidino-butyl]-amide | 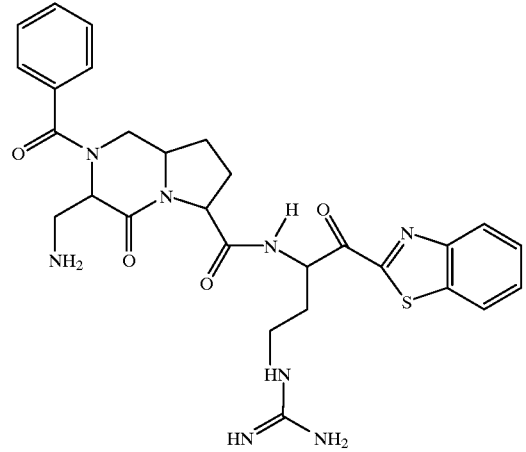 |

-continued

| 0330 | 3-Aminomethyl-4-oxo-2-phenylacetyl-octahydro-pyrrolo[1,2-a]pyrazine-6-carboxylic acid[1-(benzothiazole-2-carbonyl)-4-guanidino-butyl]-amide | 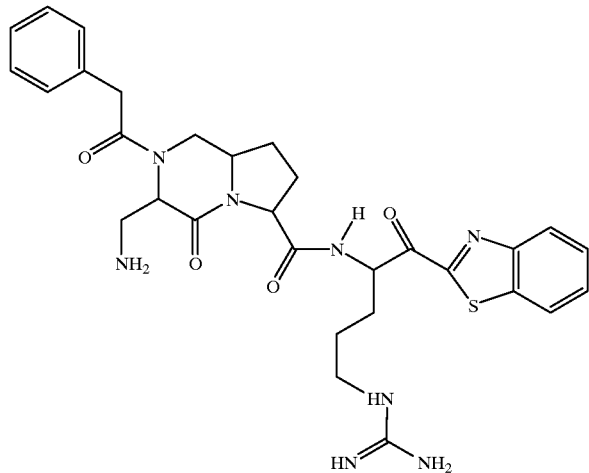 |
| 0335 | 2-Benzoyl-4-oxo-octahydro-pyrrolo[1,2-a]pyrazine-6-carboxylic acid[4-guanidino-1-(thiazole-2-carbonyl)-butyl]-amide | 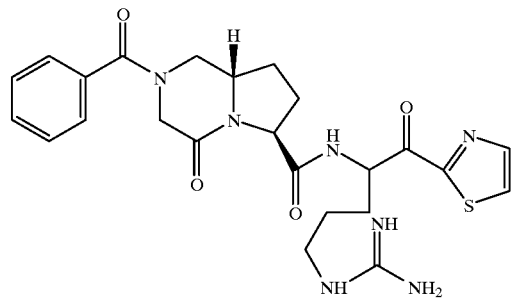 |
| 0340 | 4-Oxo-2-(3-phenyl-propionyl)-octahydro-pyrrolo[1,2-a]pyrazine-6-carboxylic acid[4-guanidino-1-(thiazole-2-carbonyl)-butyl]-amide | 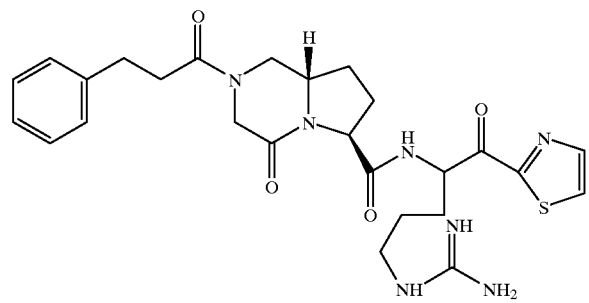 |
| 0345 | 4-Oxo-2-(3-phenyl-propionyl)-octahydro-pyrrolo[1,2-a]pyrazine-6-carboxylic acid[4-guanidino-1-(5-methyl-thiazole-2-carbonyl)-butyl]-amide | 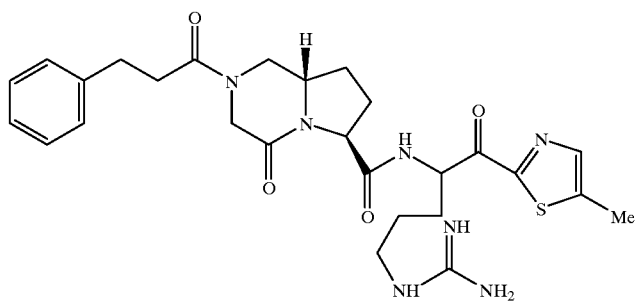 |

-continued

| | | |
|---|---|---|
| 0350 | 2-(3-Cyclohexyl-propionyl)4-oxo-octahydro-pyrrolo[1,2-a]pyrazine-6-carboxylic acid[4-guanidino-1-(2-thiazole-carbonyl)-butyl]-amide | 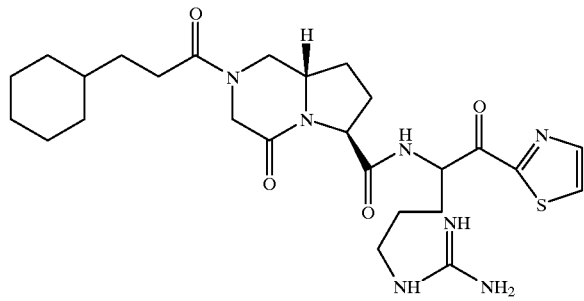 |
| 0355 | 5-Oxo-7-(3-phenyl-propionyl)-octahydro-2-thia-4a,7-diaza-naphthalene-4-carboxylic acid[4-guanidino-1-(thiazole-2-carbonyl)-butyl]-amide | 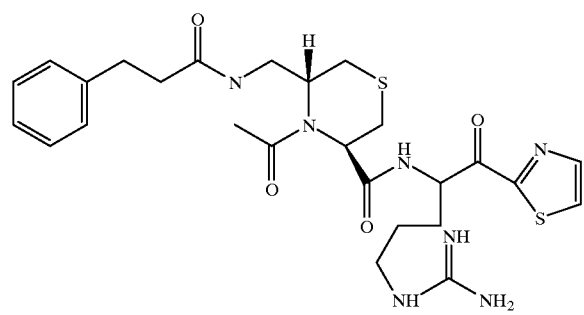 |
| 0365 | 4-Oxo-2-(4-phenyl-butyryl)-octahydro-pyrrolo[1,2-a]pyrazine-6-carboxylic acid[4-guanidino-1-(thiazole-2-carbonyl)-butyl]-amide | 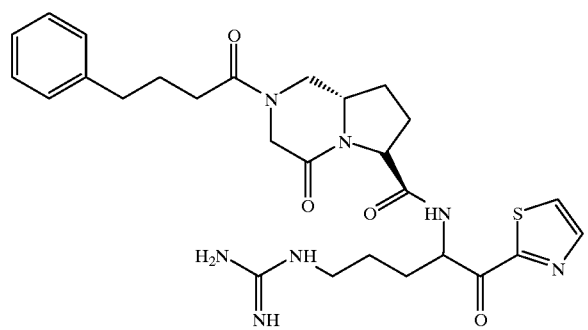 |
| 0370 | 4-Oxo-2-phenylacetyl-octahydro-pyrrolo[1,2-a]pyrazine-6-carboxylic acid[4-guanidino-1-(thiazole-2-carbonyl)-butyl]-amide | 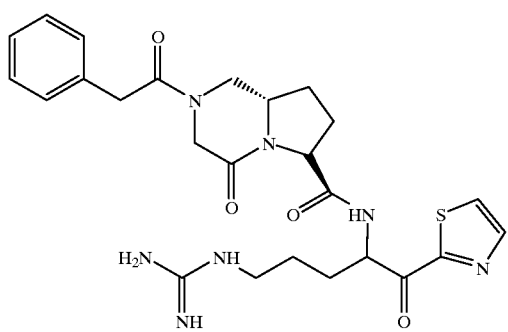 |

| | | |
|---|---|---|
| 0375 | 2-(2-Amino-3-phenyl-propionyl)-4-oxo-octahydro-pyrrolo[1,2-a]pyrazine-6-carboxylic acid[4-guanidino-1-(thiazole-2-carbonyl)-butyl]-amide | 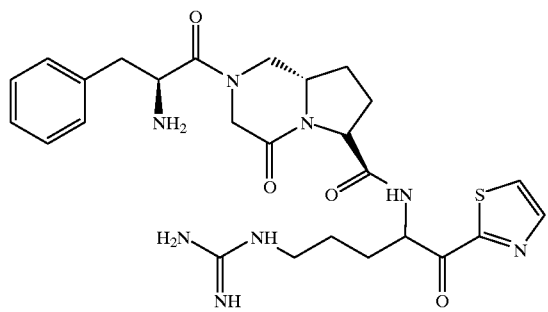 |
| 0380 | 2-[2-Amino-3-(4-hydroxy-phenyl)-propionyl]-4-oxo-octahydro-pyrrolo[1,2-a]pyrazine-6-carboxylic acid[4-guanidino-1-(thiazole-2-carbonyl)-butyl]-amide | 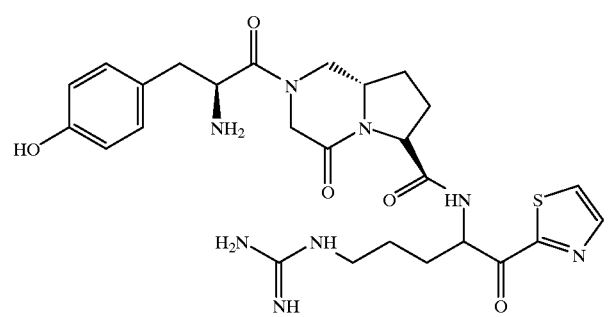 |
| 0385 | 2-[2-Amino-3-(4-fluoro-phenyl)-propionyl]-4-oxo-octahydro-pyrrolo[1,2-a]pyrazine-6-carboxylic acid[4-guanidino-1-(thiazole-2-carbonyl)-butyl]-amide | 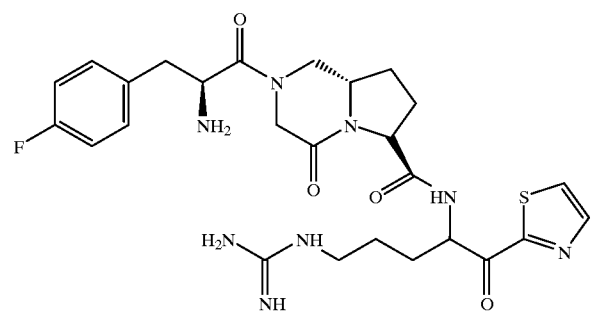 |
| 0390 | 4-Oxo-2-(3-phenyl-propyl)-octahydro-pyrrolo[1,2-a]pyrazine-6-carboxylic acid [4-guanidino-1-(thiazole-2-carbonyl)-butyl]-amide | 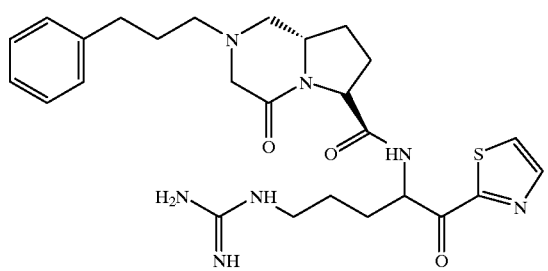 |

-continued

| | | |
|---|---|---|
| 0395 | 2-[2-Amino-3-(1H-indol-3-yl)-propionyl]-4-oxo-octahydro-pyrrolo[1,2-a]pyrazine-6-carboxylic acid[4-guanidino-1-(thiazole-2-carbonyl)-butyl]-amide | 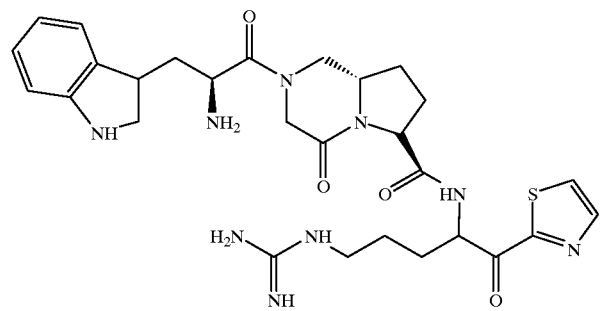 |
| 0400 | 4-Oxo-2-(3-thiophen-3-yl-propionyl)-octahydro-pyrrolo[1,2-a]pyrazine-6-carboxylic acid[4-guanidino-1-(thiazole-2-carbonyl)-butyl]-amide | 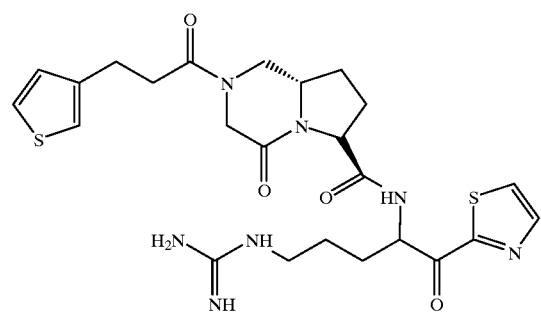 |
| 0405 | 4-Oxo-2-(3-thiophen-2-yl-propionyl)-octahydro-pyrrolo[1,2-a]pyrazine-6-carboxylic acid[4-guanidino-1-(thiazole-2-carbonyl)-butyl]-amide | 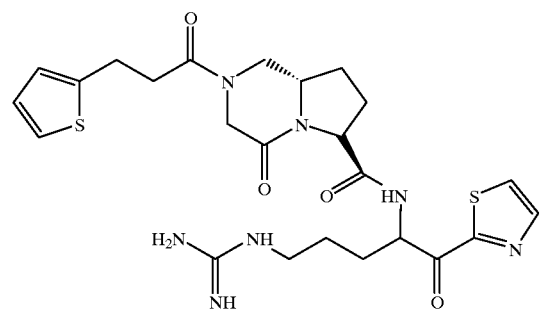 |
| 0410 | 2-(3-1 H-Imidazo1-4-yl-propionyl)-4-oxo-octahydro-pyrrolo[1,2-a]pyrazine-6-carboxylic acid[4-guanidino-1-(thiazole-2-carbonyl)-butyl]-amide | 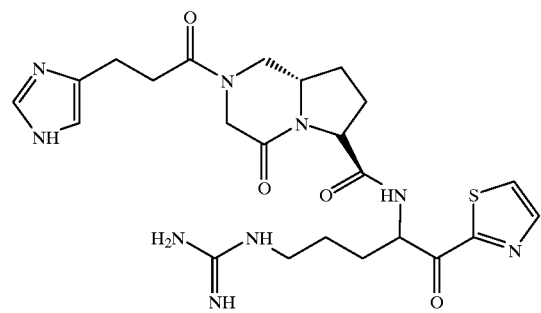 |

| | | |
|---|---|---|
| 0415 | 2-(2-Amino-3-thiophen-3-yl-propionyl)-4-oxo-octahydro-pyrrolo[1,2-a]pyrazine-6-carboxylic acid[4-guanidino-1-(thiazole-2-carbonyl)-butyl]-amide | 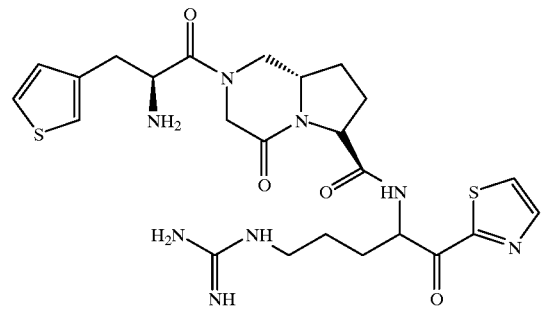 |
| 0420 | 4-Oxo-2-(1,2,3,4-tetrahydro-isoquinoline-3-carbonyl)-octahydro-pyrrolo[1,2-a]pyrazine-6-carboxylic acid[4-guanidino-1-(thiazole-2-carbonyl)-butyl]-amide | 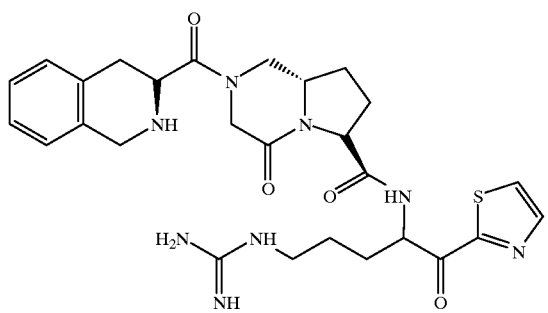 |
| 0425 | 2-(Hydroxy-phenyl-acetyl)-4-oxo-octahydro-pyrrolo[1,2-a]pyrazine-6-carboxylic acid [4-guanidino-1-(thiazole-2-carbonyl)-butyl]-amide | 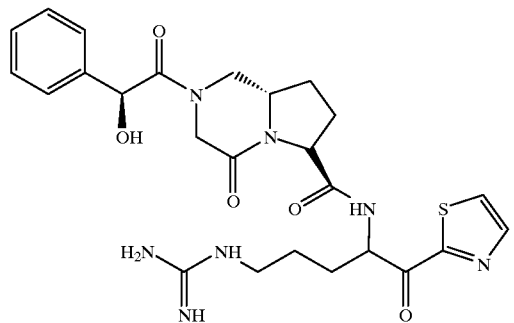 |
| 0430 | 2-(2-Hydroxy-3-phenyl-propionyl)-4-oxo-octahydro-pyrrolo[1,2-a]pyrazine-6-carboxylic acid[4-guanidino-1-(thiazole-2-carbonyl)-butyl]-amide | 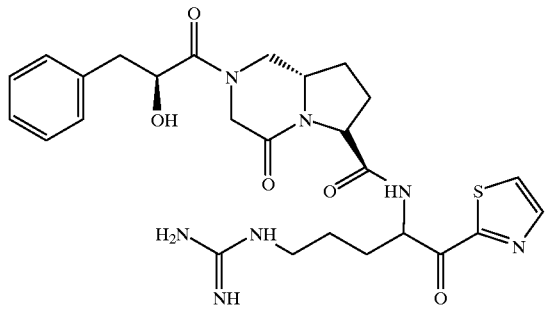 |

-continued

| | | |
|---|---|---|
| 0435 | 4-Oxo-2-phenoxyacetyl-octahydro-pyrrolo[1,2-a]pyrazine-6-carboxylic acid [4-guanidino-1-(thiazole-2-carbonyl)-butyl]-amide | 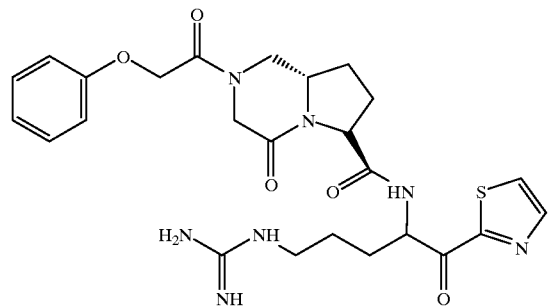 |
| 0440 | 4-Oxo-2-(3-phenoxy-propionyl)-ocatahydro-pyrrolo[1,2-a]pyrazine-6-carboxylic acid[4-guanidino-1-(thiazole-2-carbonyl)-butyl]-amide | 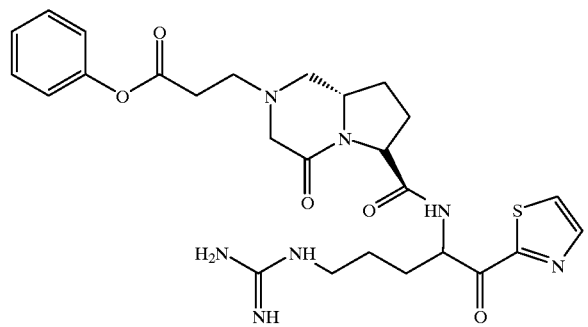 |
| 0445 | 4-Oxo-2-(2-phenyl-ethanesulfonyl)-octahydro-pyrrolo[1,2-a]pyrazine-6-carboxylic acid[4-guanidino-1-(thiazle-2-carbonyl)-butyl]-amide | 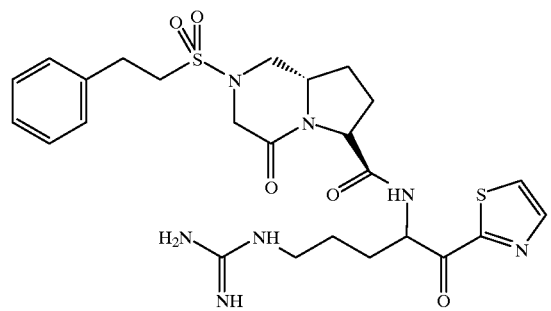 |
| 0450 | 2-(Naphthalene-2-sulfonyl)-4-oxo-octahydro-pyrrolo[1,2-a]pyrazine-6-carboxylic acid[4-guanidino-1-(thiazole-2-carbonyl)-butyl]-amide | 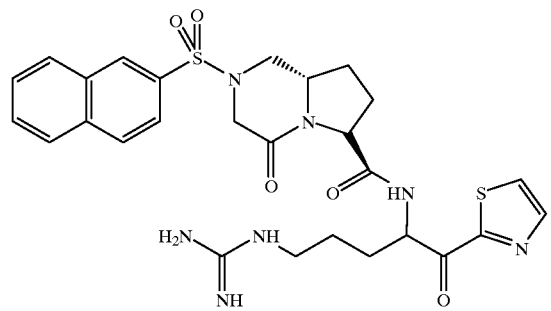 |

| | |
|---|---|
| 0455 | 4-(6-[4-Guanidino-1-(thiazole-2-carbonyl)-butylcarbamoyl]-4-oxo-hexahydro-pyrrolo[1,2-a]pyrazin-2yl)-4-oxo-3-(2 propyl-pentanoylamino)-butyric acid methyl ester |

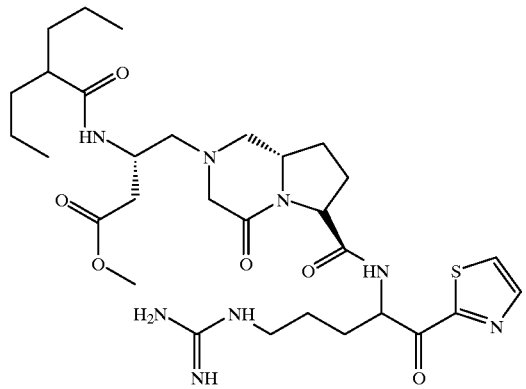

| | |
|---|---|
| 0460 | 4-Oxo-2-(3-phenyl-propionyl)-octahydro-pyrrolo[1,2-a]pyrazine-6-carboxylic acid[4-guanidino-1)-butyl]-amide |

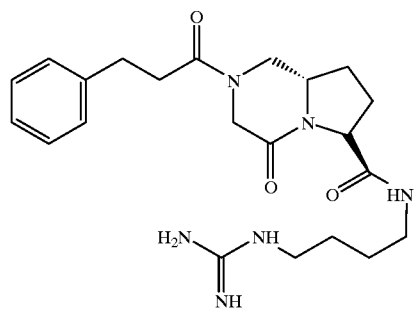

| | |
|---|---|
| 0465 | 4-Oxo-2-(3-phenyl-propionyl)-octahydro-pyrrolo[1,2-a]pyrazine-6-carboxylic acid[3-guanidino-propyl)-amide |

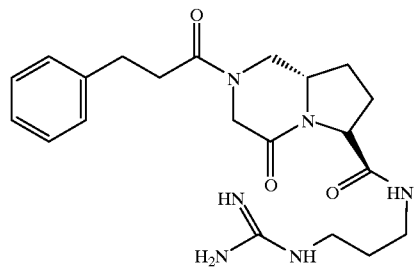

| | |
|---|---|
| 0470 | 4-(6-[4-Guanidino-1-(thiazole-2-carbonyl)-butylcarbamoyl]-4-oxo-hexahydro-pyrrolo[1,2-a]pyrazin 2-yl)-4-oxo-butyric acid |

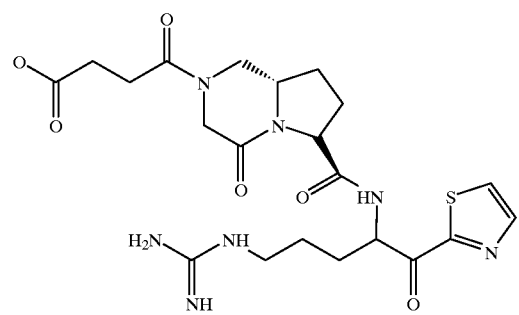

| | | |
|---|---|---|
| 0475 | 4-Oxo-2-(3-phenyl-propionyl)-octahydro-pyrrolo[1,2-a]pyrazine-6-carboxylic acid[1-(5-ethyl-thiazole-2-carbonyl)-4-guanidino-butyl]-amide | 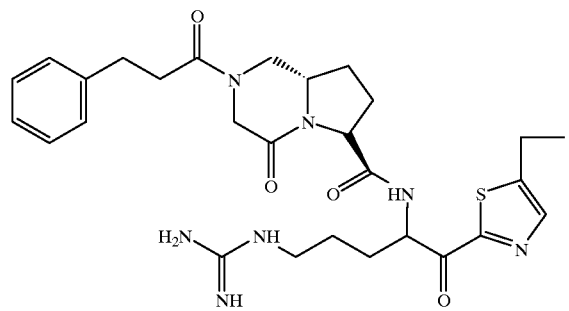 |
| 0480 | 4-Oxo-2-(3-phenyl-propionyl)-octahydro-pyrrolo[1,2-a]pyrazine-6-carboxylic acid[4-guanidino-1-(5-methyl-thiazole-2-carbonyl)-butyl]-amide | 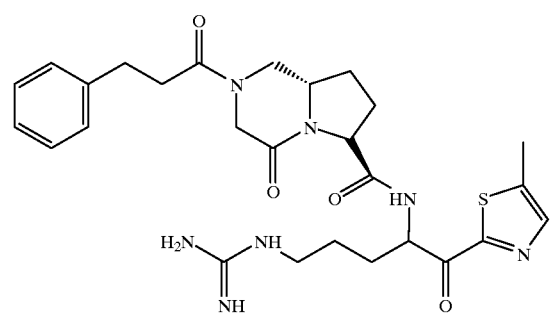 |
| 0485 | 4-Oxo-2-(3-phenyl-propionyl)-octahydro-pyrrolo[1,2-a]pyrazine-6-carboxylic acid[4-guanidino-1-(4-methyl-thiazole-2-carbonyl)-butyl]-amide | 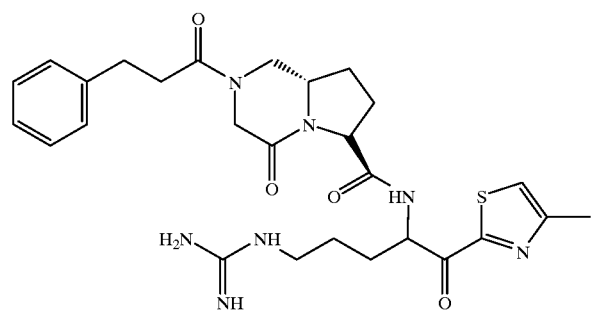 |
| 0490 | 4-Oxo-2-(3-phenyl-propionyl)-octahydro-pyrrolo[1,2-a]pyrazine-6-carboxylic acid[1-(4-ethyl-thiazole-2-carbonyl)-4-guanidino-butyl]-amide | 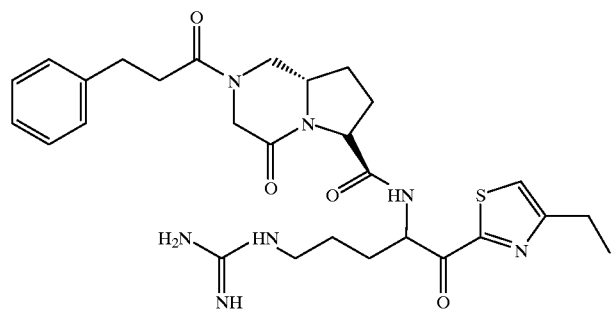 |

-continued

| | | |
|---|---|---|
| 0495 | 4-Oxo-2-(3-phenyl-propionyl)-octahydro-pyrrolo[1,2-a]pyrazine-6-carboxylic acid (4-carbamimidoyl-pheny)-amide | 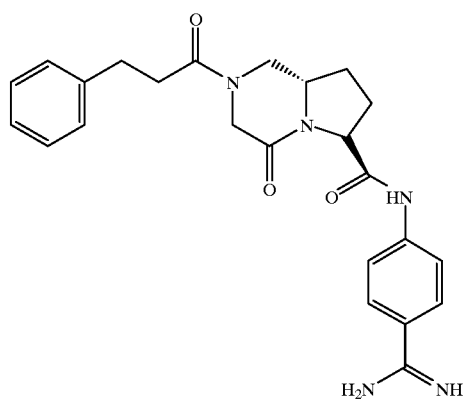 |
| 0500 | 4-Oxo-2-(3-phenyl-propionyl)-octahydro-pyrrolo[1,2-a]pyrazine-6-carboxylic acid[4-guanidino-1-(5-phenyl-thiazole-2-carbonyl)-butyl]-amide | 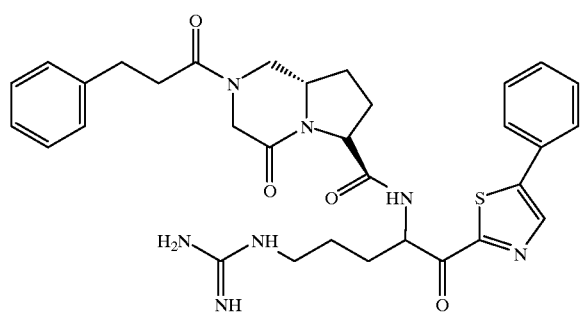 |
| 0505 | 4-Oxo-2-(3-phenyl-propionyl)-octahydro-pyrrolo[1,2-a]pyrazine-6-carboxylic acid[1-(5-benzyl-thiazole-2-carbonyl)4-guanidino-butyl]-amide | 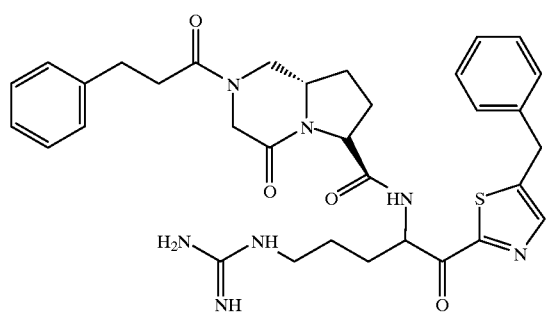 |
| 0510 | 4-Oxo-2-(3-phenyl-propionyl)-octahydro-pyrrolo[1,2-a]pyrazine-6-carboxylic acid[1-(4-carbarnimidoyl-benzyl)-2-oxo-2-thiazol-2-yl-ethyl]-amide | 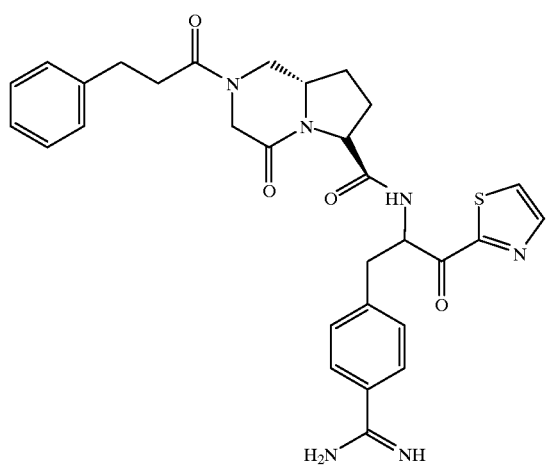 |

| | | |
|---|---|---|
| 0515 | 4-Oxo-2-(3-phenyl-propionyl)-octahydro-pyrrolo[1,2-a]pyrazine-6-carboxylic acid[1-(3-carbamimidoyl-benzyl)-2-oxo-2-thiazol-2-yl-ethyl]-amide | 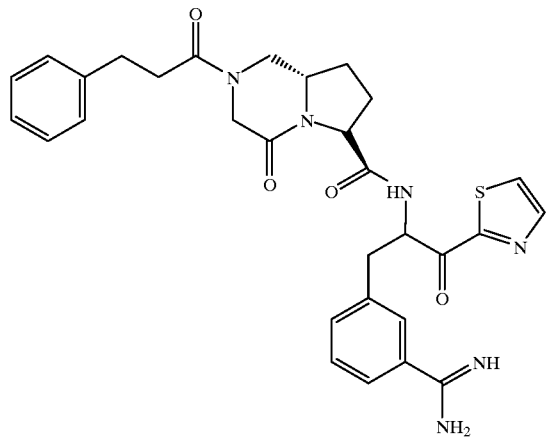 |
| 0520 | 4-Oxo-2-(3-phenyl-propionyl)-octahydro-pyrrolo[1,2-a]pyrazine-6-carboxylic acid[1-(1-carbamimidoyl-piperidin-4-ylmethyl)-2-oxo-2-thiazol-2-yl-ethyl]-amide | 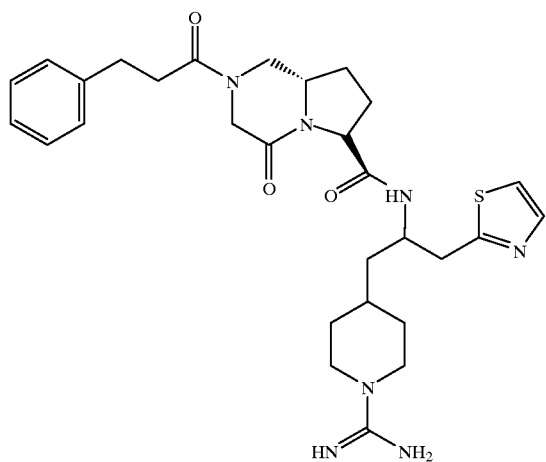 |
| 0525 | 4-Oxo-2-(3-phenyl-propionyl)-octahydro-pyrrolo[1,2-a]pyrazine-6-carboxylic acid[1-(1-carbamimidoyl-piperidin-3-ylmethyl)-2-oxo-2-thiazol-2-yl-ethyl]-amide | 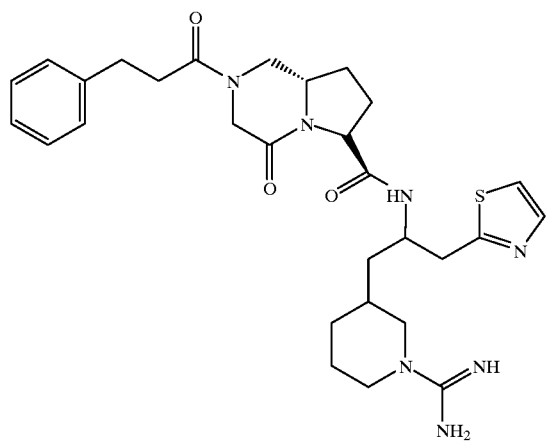 |

| | | |
|---|---|---|
| 0530 | 4-Oxo-2-(3-phenyl-propionyl)-octahydro-pyrrolo[1,2-a]pyrazine-6-carboxylic acid[1-(1-carbamimidoyl-piperidin-2-ylmethyl)-2-oxo-2-thiazol-2-yl-ethyl]-amide | 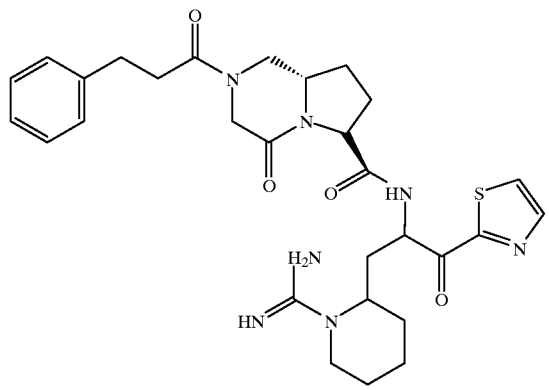 |
| 0535 | [6-[4-Guanidino-1-(thiazole-2-carbonyl)-butylcarbamoyl]-4-oxo-2-(3-phenyl-propionyl)-octahydro-pyrrolo[1,2-a]pyrazine-3-yl]-acetic acid | 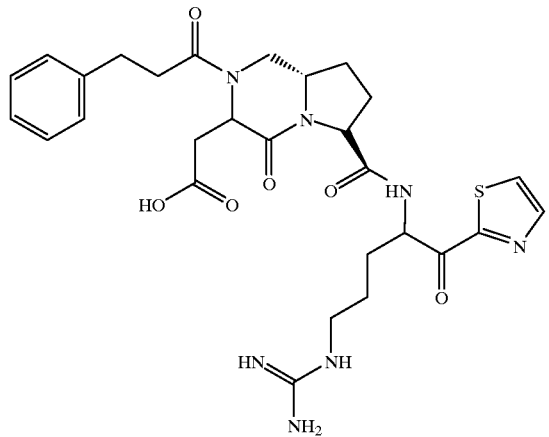 |
| 0540 | 3-[6-[4-Guanidino-1-(thiazole-2-carbonyl)-butylcarbamoyl]-4-oxo-2-(3-phenyl-propionyl)-octahydro-pyrrolo[1,2-a]pyrazin-3-yl]-propionic acid | 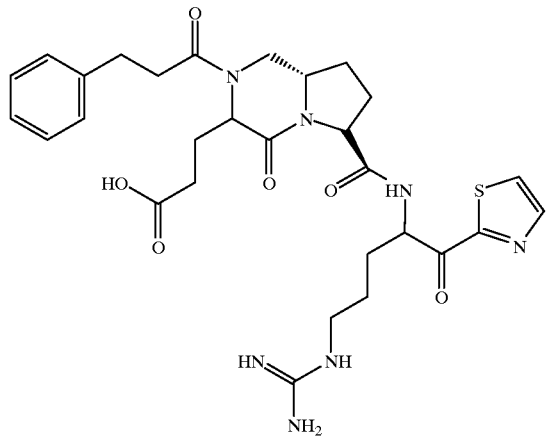 |

| | | |
|---|---|---|
| 0545 | [6-[1-(1-Carbamimidoyl-piperin-4-ylmethyl)-2-oxo-2-thiazol-2-yl-ethylcarbarnoyl]-4-oxo-2-(3-phenyl-propionyl)-octahydro-pyrrolo[1,2-a]pyrazin-3-yl)-acetic acid | 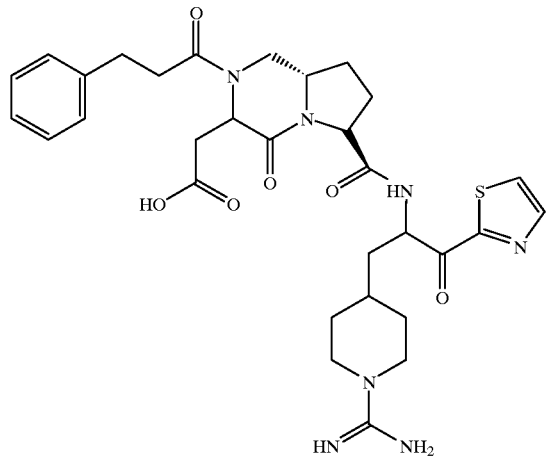 |
| 0550 | 3-[6-[1-(1-Carbamimidoyl-piperidin-4-ylmethyl)-2-oxo-2-thiazol-2-yl-ethylcarbamoyl]-4-oxo-2-(3-phenyl-propionyl)-octahydro-pyrrolo[1,2-a]pyrazin-3-yl)-acetic acid | 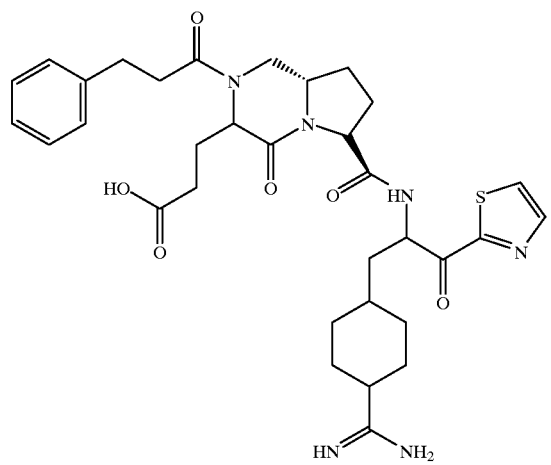 |
| 0555 | [6-[1-(1-Carbamimidoyl-piperidin-3-ylmethyl)-2-oxo-2-thiazol-2-yl-ethylcarbamoyl]-4-oxo-2-(3-phenyl-propionyl)-octahydro-pyrrolo[1,2-a]pyrazin-3-yl)-acetic acid | 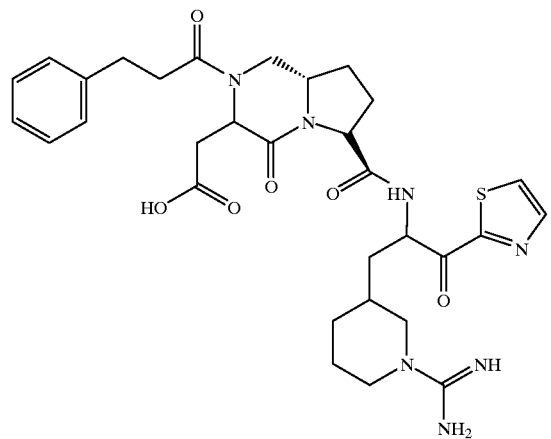 |

-continued
0560 [6-(3-Guanidino-propylcarbamoyl)-4-oxo-2-
(3-phenyl-propionyl)-octahydro-pyrrolo[1,2-
a]pyrazin-3-yl)-acetic acid
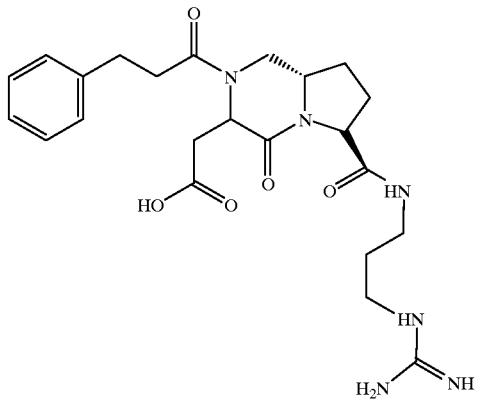
0565 3-[6-(3-Guanidino-propylcarbamoyl)-4-oxo-2-
(3-phenyl-propionyl)-octahydro-pyrrolo[1,2-
a]pyrazin-3-yl)-propionic acid
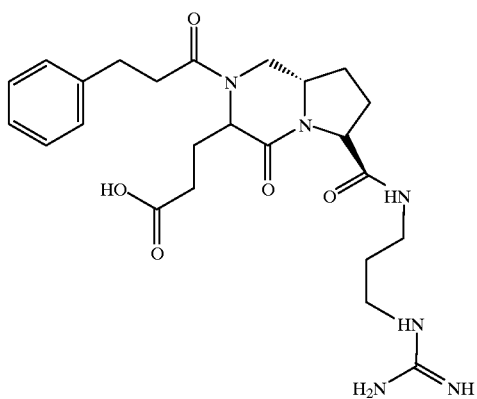
0570 4-Oxo-2-(3-phenyl-propionyl)-octahydro-
pyrrolo[1,2-a]pyrazine-6-carboxylic acid[4-
guanidino-1-(thiazole-2-carbonyl)-butyl]-
methyl-amide
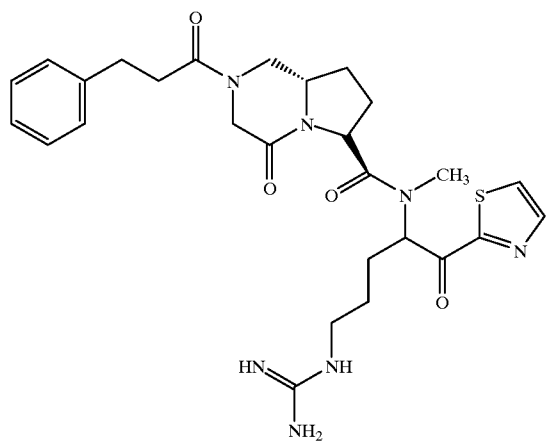

| | | |
|---|---|---|
| 0575 | 4-Oxo-2-(3-phenyl-propionyl)-octahydro-pyrrolo[1,2-a]pyrazine-6-carboxylic acid[1-(1-carbamimidoyl-piperidin-4-ylmethyl)-2-oxo-2-thiazol-2-yl-ethyl]-methyl-amide | 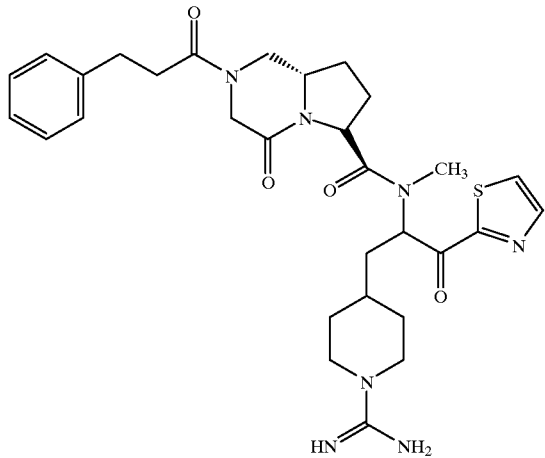 |
| 0580 | [6-([1-Carbamimidoyl-piperidin-4-ylmethyl)-2-oxo-2-thiazol-2-yl-ethyl]-methyl-carbamoyl)-4-oxo-2-(3-phenyl-propionyl)-octahydro-pyrrolo[1,2-a]pyrazin-3-yl]-acetic-acid | 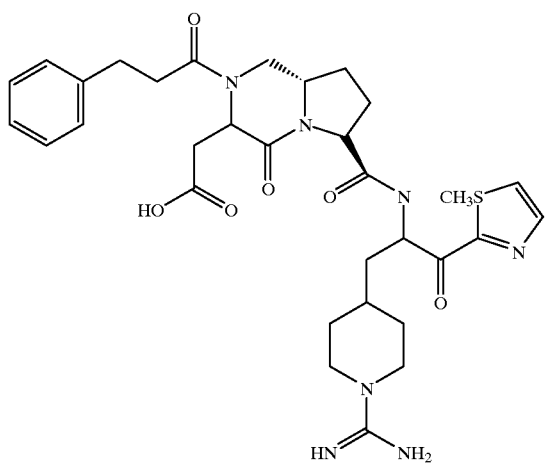 |
| 0585 | 4-Oxo-2-(3-phenyl-propionyl)-octahydro-pyrrolo[1,2-a]pyrazine-6-carboxylic acid[1-(1-carbamimidoyl-piperidin-3-ylmethyl)-2-oxo-2-thiazol-2-yl-ethyl]-methyl-amide | 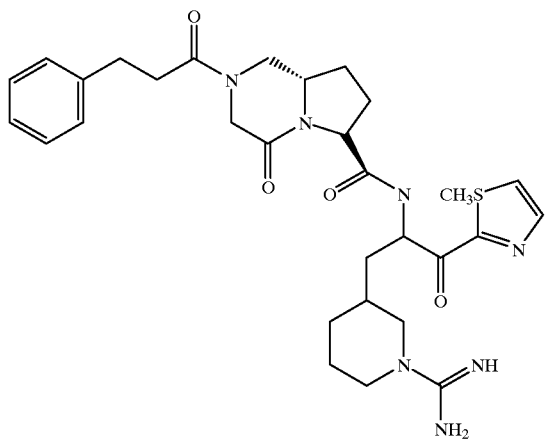 |

| | | |
|---|---|---|
| 0590 | 4-Oxo-2-(3-phenyl-propionyl)-octahydro-pyrrolo[1,2-a]pyrazine-6-carboxylic acid(3-guanidino-propyl)-methyl-amide | 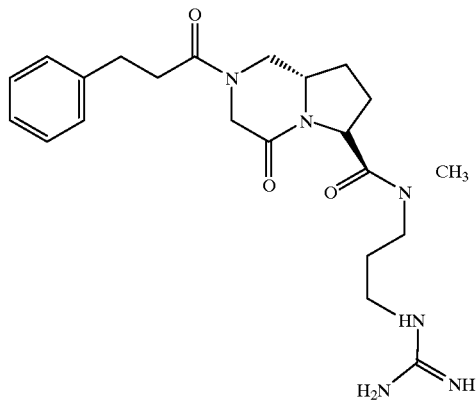 |
| 0595 | 2-(Naphthalene-2-carbonyl)-4-oxo-octahydro-pyrrolo[1,2-a]pyrazine-6-carboxylic acid[4-guanidino-1-(thiazole-2-carbonyl)-butyl]-amide | 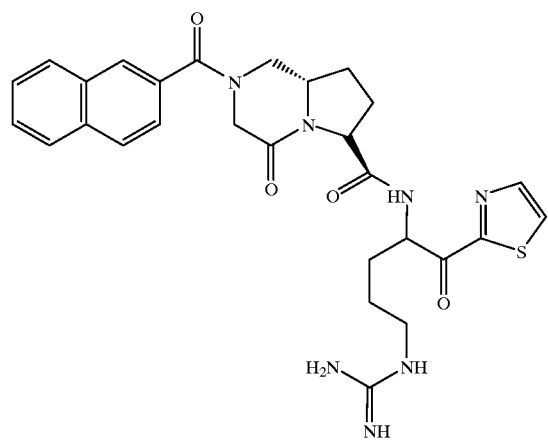 |
| 0600 | 2-(Naphthalene-1-carbonyl)-4-oxo-octahydro-pyrrolo[1,2-a]pyrazine-6-carboxylic acid[4-guanidino-1-(thiazole-2-carbonyl)-butyl]-amide | 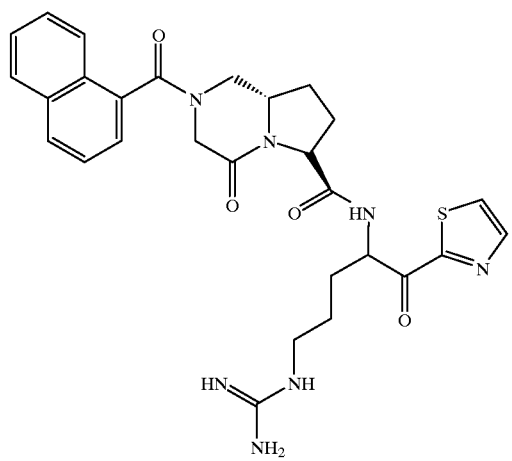 |

| | | |
|---|---|---|
| 0605 | 2-(3-Naphthalen-1-yl-proplonyl)4-oxo-octahydro-pyrrolo[1,2-a]pyrazine-6-carboxylic acid[4-guanidino-1-(thiazole-2-carbonyl)-butyl]-amide | 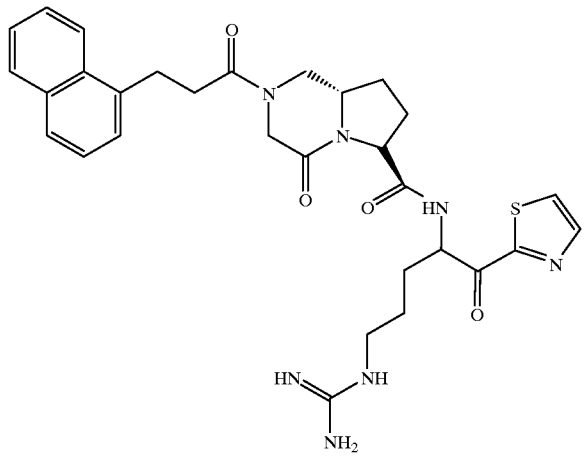 |
| 0610 | 2-(4-tert-Butyl-benzoyl)-4-oxo-octahydro-pyrrolo[1,2-a]pyrazine-6-carboxylic acid[4-guanidino-1-(thiazole-2-carbonyl)-butyl]-amide | 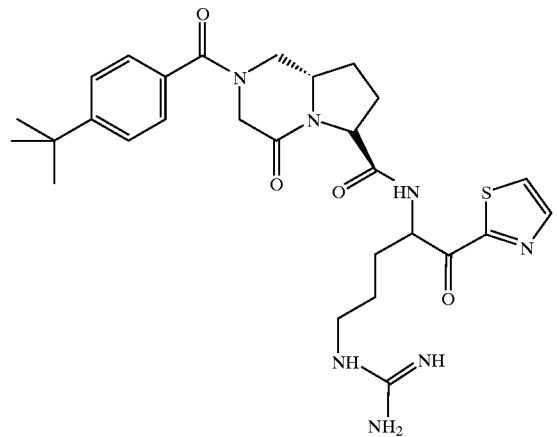 |
| 0615 | 2-(Benzo[1,3]dioxole-5-carbonyl)-4-oxo-octahydro-pyrrolo[1,2-a]pyrazine-6-carboxylic acid[4-guanidino-1-(thiazole-2-carbonyl)-butyl]-amide | 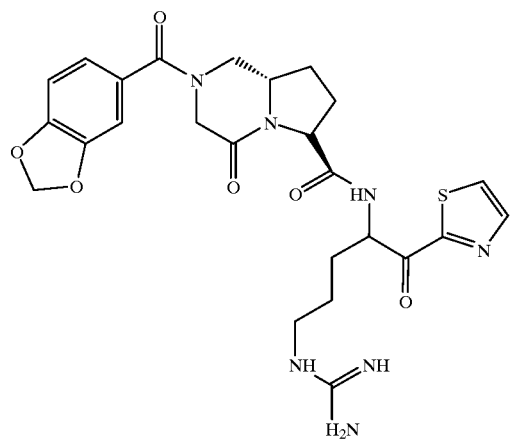 |

| | | |
|---|---|---|
| 0620 | 2-(3-Benzo[1,3]dioxol-5-yl-propionyl)-4-oxo-octahydro-pyrrolo[1,2-a]pyrazine-6-carboxylic acid[4-guanidino-1-(thiazole-2-carbonyl)-butyl]-amide | 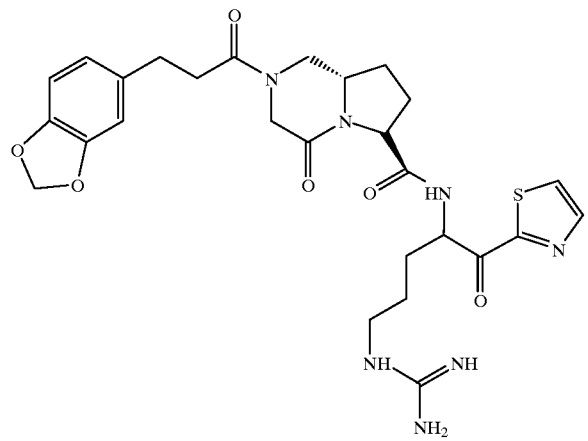 |
| 0625 | 2-[2-(2-Methyl-benzylidene)-but-3-enoyl]-4-oxo-octahydro-pyrrolo[1,2-a]pyrazine-6-carboxylic acid[1-(1-carbamimidoyl-piperidin-3-ylmethyl)-2-oxo-2-thiazol-2-yl-ethyl]-amide | 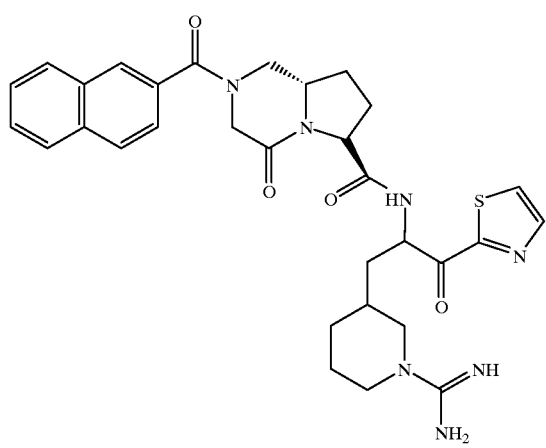 |
| 0630 | 2-[2-(2-Methyl-benzylidene)-but-3-enoyl]-4-oxo-octahydro-pyrrolo[1,2-a]pyrazine-6-carboxylic acid[1-(1-carbamimidoyl-piperidin-4-ylmethyl)-2-oxo-2-thiazol-2-yl-ethyl]-amide | 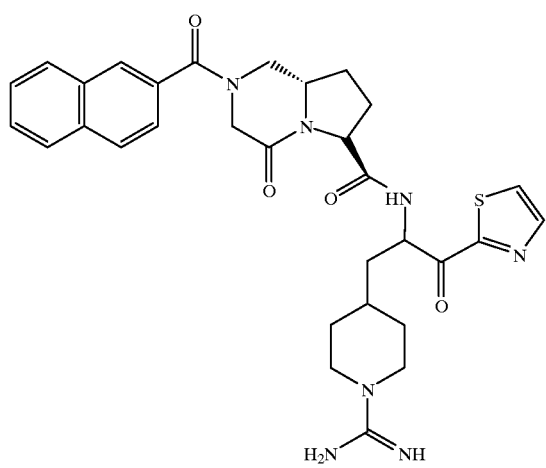 |

-continued

| | | |
|---|---|---|
| 0635 | 2-(2-Benzylidene-pent-3-enoyl)-4-oxo-octahydro-pyrrolo[1,2-a]pyrazine-6-carboxylic acid (3-guanidino-propyl)-amide | 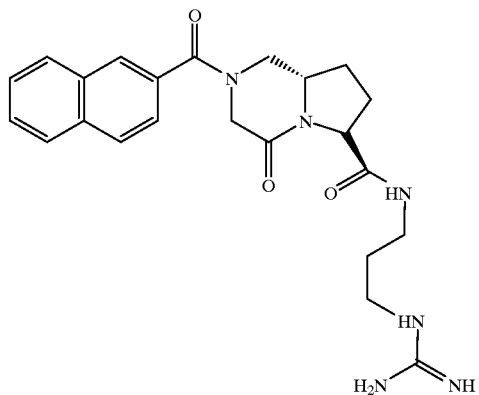 |
| 0640 | 4-Oxo-2-(3-phenyl-propionyl)-octahydro-pyrrolo[1,2-a]pyrazine-6-carboxylic acid 4-carbamimidoyl-benzylamide | 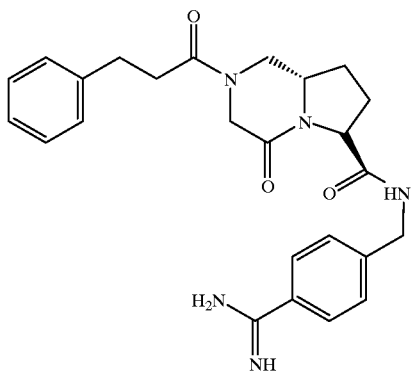 |
| 0645 | 4-Oxo-2-(3-phenyl-propionyl)-octahydro-pyrrolo[1,2-a]pyrazine-6-carboxylic acid[4-imidazol-1-yl-1-(thiazole-2-carbonyl)-butyl]-amide | 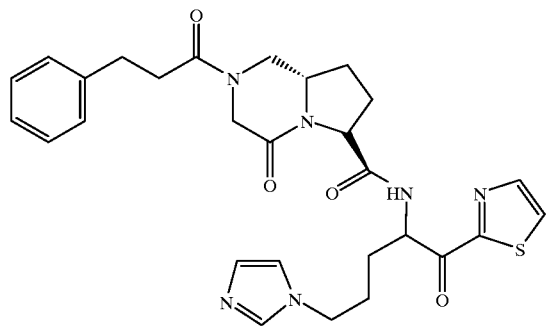 |
| 0650 | 4-Oxo-2-(3-phenyl-propionyl)-octahydro-pyrrolo[1,2-a]pyrazine-6-carboxylic acid[4-(2-amino-imidazol-1-yl)-1-(thiazole-2-carbonyl)-butyl]-amide | 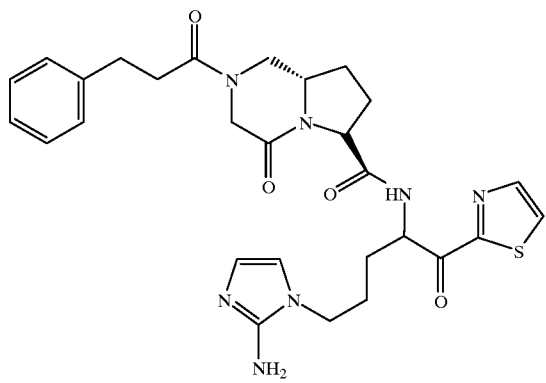 |

-continued 0655 4-Oxo-2-(3-phenyl-propionyl)-octahydro-
pyrrolo[1,2-a]pyrazine-6-carboxylic acid[3-(2-
amino-6-methyl-pyrimidin-4-yl)-1-(thiazole-2-
carbonyl)-propyl]-amide

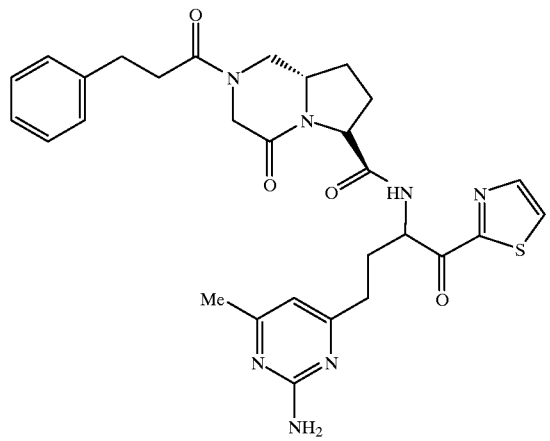

0670 4-Oxo-2-(3-phenyl-propionyl)-octahydro-
pyrrolo[1,2-a]pyrazine-6-carboxylic acid[3-(2-
amino-6-chloro-pyrimidin-4-yl)-1-(thiazole-2-
carbonyl)-propyl]-amide

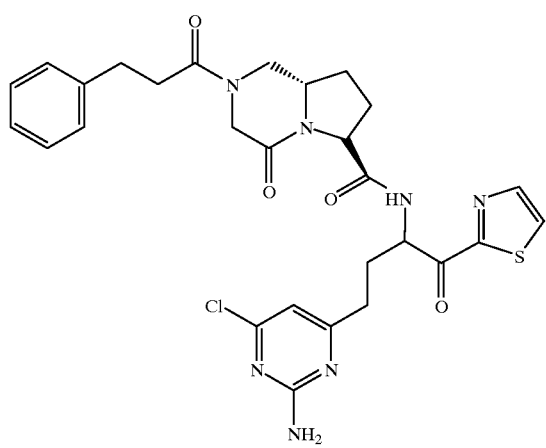

0675 4-Oxo-2-(3-phenyl-propionyl)-octahydro-
pyrrolo[1,2-a]pyrazine-6-carboxylic acid[3-(6-
amino-pyridin-2-yl)-1-(thiazole-2-carbonyl)-
propyl]-amide

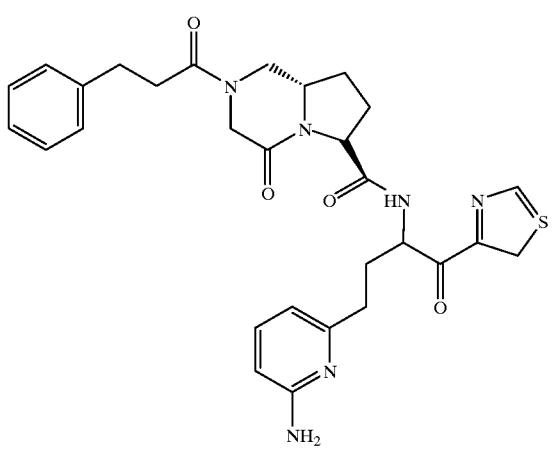

| | | |
|---|---|---|
| 0680 | 4-Oxo-2-(3-phenyl-propionyl)-octahydro-pyrrolo[1,2-a]pyrazine-6-carboxylic acid[3-(2-amino-pyridin-4-yl)-1-(thiazole-2-carbonyl)-propyl]-amide | 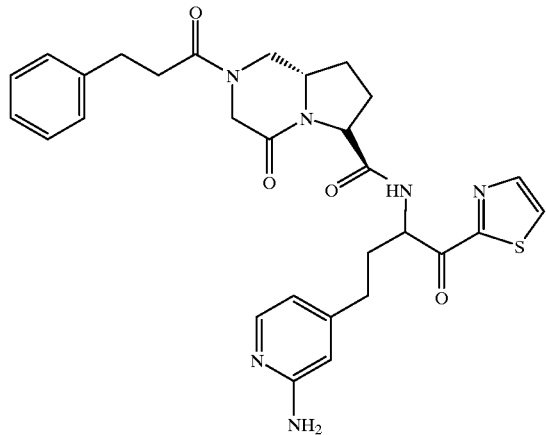 |
| 0685 | 4-Oxo-2-(3-phenyl-propionyl)-octahydro-pyrrolo[1,2-a]pyrazine-6-carboxylic acid[2-(2-amino-pyridin-4-yl)-1-(thiazole-2-carbonyl)-ethyl]-amide | 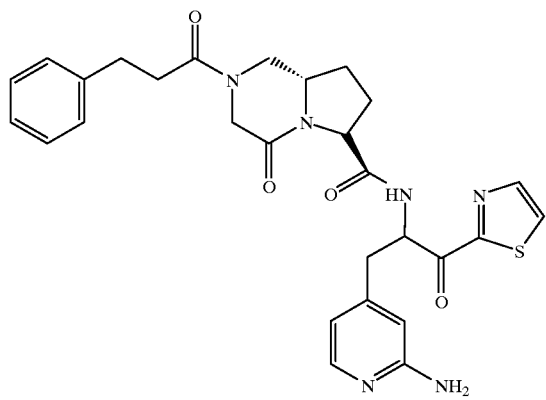 |
| 0690 | 4-Oxo-2-(3-phenyl-propionyl)-octahydro-pyrrolo[1,2-a]pyrazine-6-carboxylic acid[2-(6-amino-pyridin-2-yl)-1-(thiazole-2-carbonyl)-ethyl]-amide | 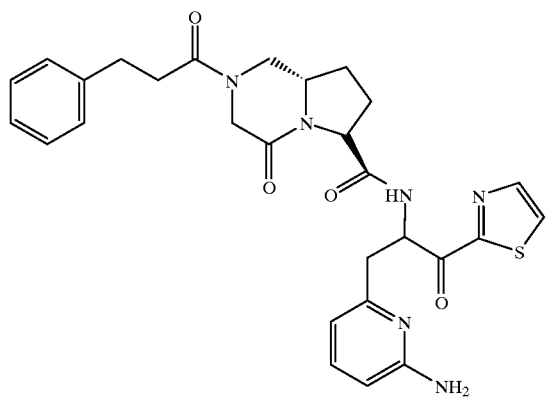 |

| | | |
|---|---|---|
| 0695 | 2-[4-Oxo-2-(3-phenyl-propionyl)-octahydro-pyrrolo[1,2-a]pyrazine-6-carbonyl]-3-(thiazole-2-carbonyl)-1,2,3,4-tetrahydro-isoquinoline-6-carboxamidine | 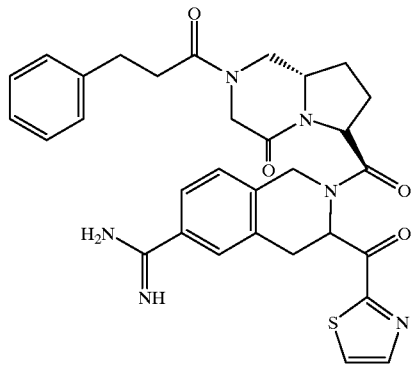 |
| 0700 | 2-[4-Oxo-2-(3-phenyl-propionyl)-octahydro-pyrrolo[1,2-a]pyrazine-6-carbonyl]-3-(thiazole-2-carbonyl)-1,2,3,-tetrahydro-isoquinoline-7-carboxamidine | 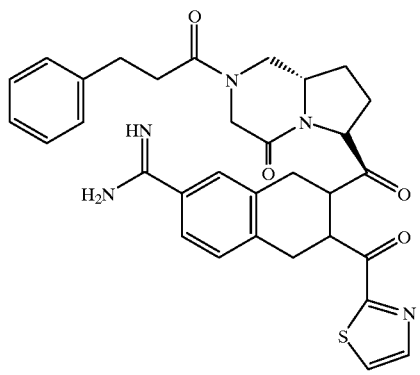 |
| 0705 | N-[1-[4-Oxo-2-(3-phenyl-propionyl)-octahydro-pyrrolo[1,2-a]pyrazine-6-carbonyl]-5-(thiazole-2-carbonyl)-pyrrolidin-3-yl]-guanidine | 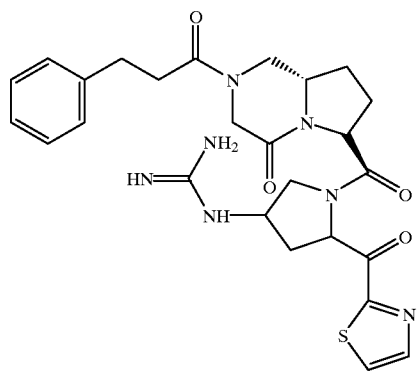 |
| 0710 | 4-Oxo-2-(3-phenyl-propionyl)-octahydro-pyrrolo[1,2-a]pyrazine-6-carboxylic acid[1-(4-amino-cyclohexyl)-2-oxo-2-thiazol-2-yl-ethyl]-amide | 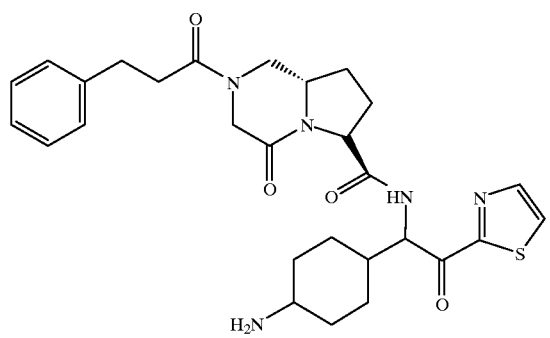 |

-continued
| | | |
|---|---|---|
| 0715 | 4-Oxo-2-(3-phenyl-propionyl)-octahydro-pyrrolo[1,2-a]pyrazine-6-carboxylic acid[1-(4-amino-cyclohexylmethyl)-2-oxo-2-thiazol-2-yl-ethyl]-amide | 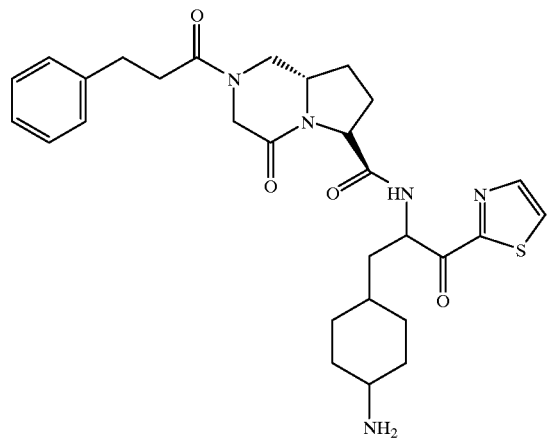 |
| 0720 | 4-Oxo-2-(3-phenyl-propionyl)-octahydro-pyrrolo[1,2-a]pyrazine-6-carboxylic acid[1-(4-amino-benzyl)-2-oxo-2-thiazol-2-yl-ethyl]-amide | 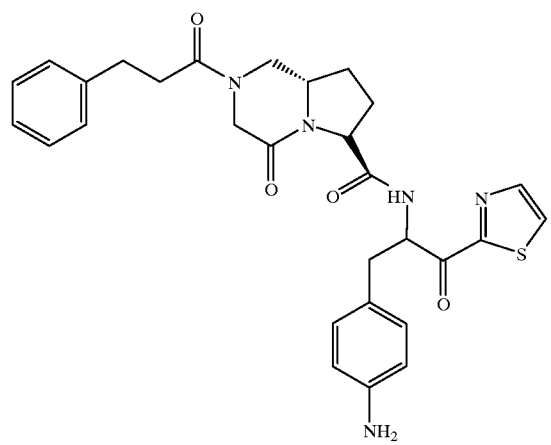 |
| 0725 | 4-Oxo-2-(3-phenyl-propionyl)-octahydro-pyrrolo[1,2-a]pyrazine-6-carboxylic acid[1-(4-aminomethyl-benzyl)-2-oxo-2-thiazol-2-yl-ethyl]-amide | 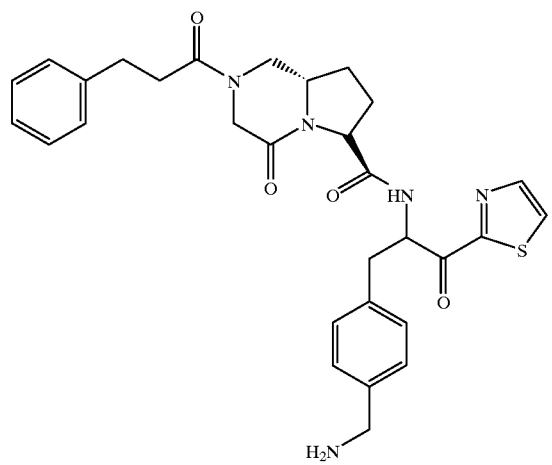 |

-continued

| | | |
|---|---|---|
| 0730 | 4-Oxo-2-(3-phenyl-propionyl)-octahydro-pyrrolo[1,2-a]pyrazine-6-carboxylic acid[1-(3-aminomethyl-benzyl)-2-oxo-2-thiazol-2-yl-ethyl]-amide | 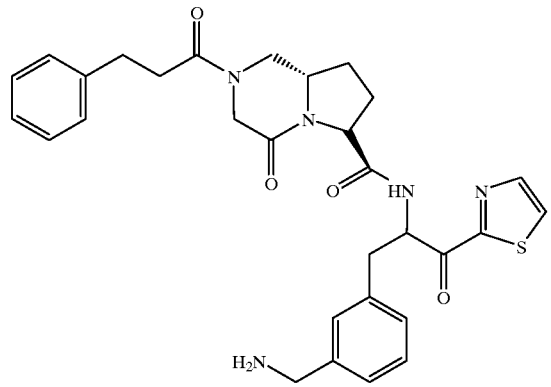 |
| 0735 | 4-Oxo-2-(3-phenyl-propionyl)-octahydro-pyrrolo[1,2-a]pyrazine-6-carboxylic acid(2-oxo-1-piperidin-4-ylmethyl-2-thiazol-2-yl-ethyl)-amide | 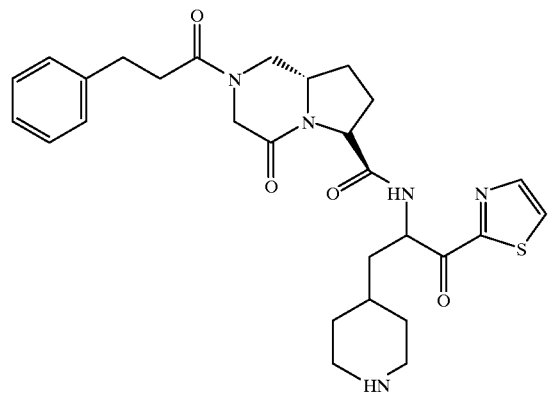 |
| 0740 | 4-Oxo-2-(3-phenyl-propionyl)-octahydro-pyrrolo[1,2-a]pyrazine-6-carboxylic acid(2-oxo-1-piperidin-3-yl-2-thiazol-2-yl-ethyl)-amide | 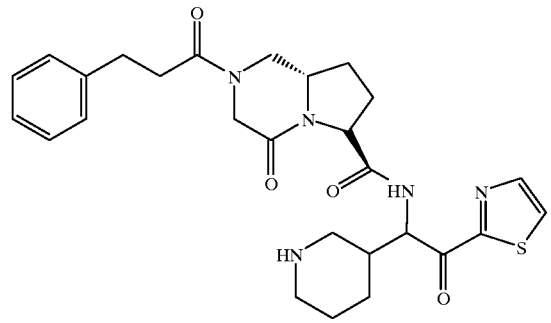 |
| 0745 | 4-Oxo-2-(3-phenyl-propionyl)-octahydro-pyrrolo[1,2-a]pyrazine-6-carboxylic acid[1-(3-guanidino-cyclohexylmethyl)-2-oxo-2-thiazol-2-yl-ethyl]-amide | 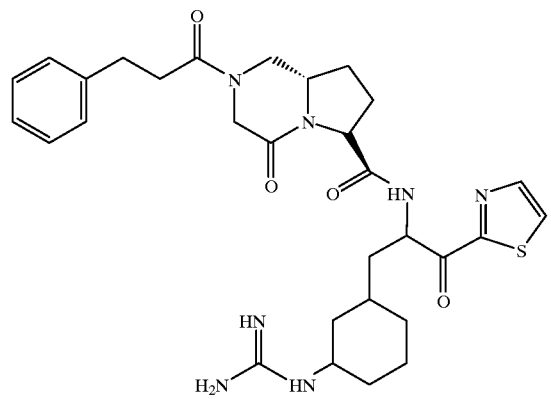 |

| | | |
|---|---|---|
| 0750 | 4-Oxo-2-(3-phenyl-propionyl)-octahydro-pyrrolo[1,2-a]pyrazine-6-carboxylic acid[1-(4-guanidino-cyclohexylmethyl)-2-oxo-2-thiazol-2-yl-ethyl]-amide | 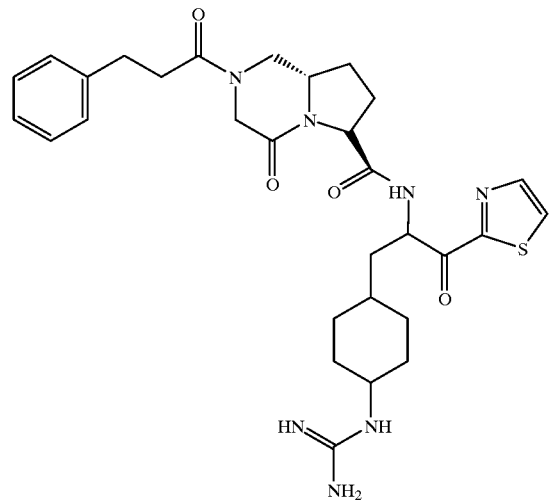 |
| 0755 | 4-Oxo-2-(3-phenyl-propionyl)-octahydro-pyrrolo[1,2-a]pyrazine-6-carboxylic acid[1-(2-guanidino-cyclohexylmethyl)-2-oxo-2-thiazol-2-yl-ethyl]-amide | 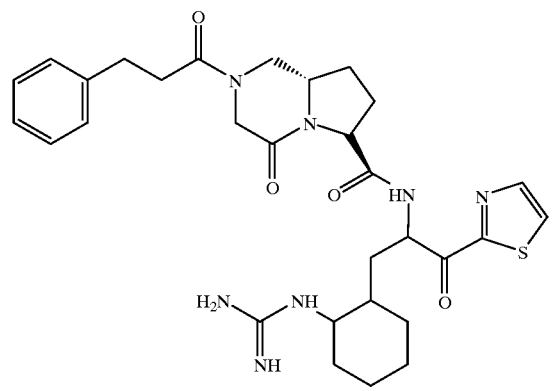 |
| 0760 | 4-Oxo-2-(3-phenyl-propionyl)-octahydro-pyrrolo[1,2-a]pyrazine-6-carboxylic acid[1-(5-benzyl-thiazole-2-carbonyl)-4-guanidino-butyl]-amide | 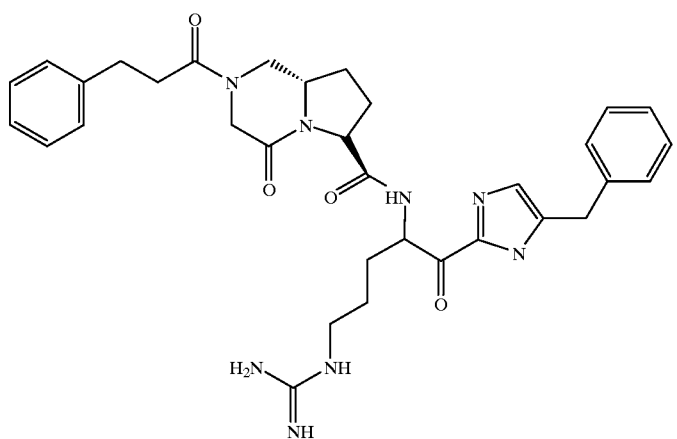 |

-continued
| | | |
|---|---|---|
| 0765 | 4-Oxo-2-(3-phenyl-propionyl)-octahydro-pyrrolo[1,2-a]pyrazine-6-carboxylic acid[4-guanidino-1-(5-phenyl-thiazole-2-carbonyl)-butyl]-amide | 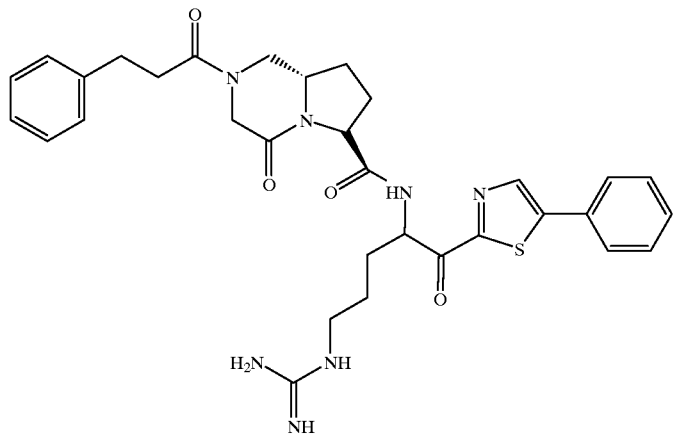 |
| 0770 | 4-Oxo-2-(3-phenyl-propionyl)-octahydro-pyrido[1,2-a]pyrazine-6-carboxylic acid[4-guanidino-1-(thiazole-2-carbonyl)-butyl]-amide | 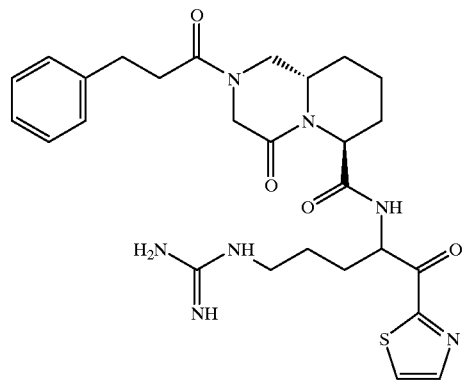 |
| 0775 | 5-Oxo-7-(3-phenyl-propionyl)-octahydro-2-thia-4a,7-diaza-naphthalene-4-carboxylic acid [4-guanidino-1-(thiazole-2-carbonyl)-butyl]-amide | 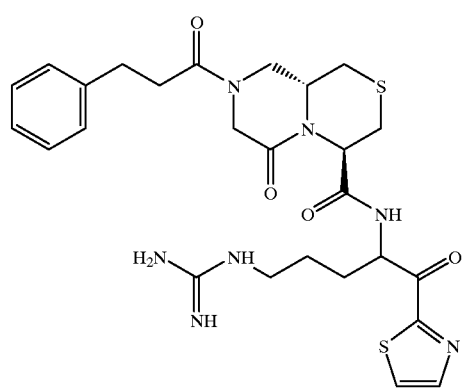 |

| | | |
|---|---|---|
| 0780 | 5-Oxo-7-(3-phenyl-propionyl)-octahydro-2-thia-4a,7-diaza-naphthalene-4-carboxylic acid [1-(4-carbamimidoyl-benzyl)-2-oxo-2-thiazol-2-yl-ethyl]-amide | 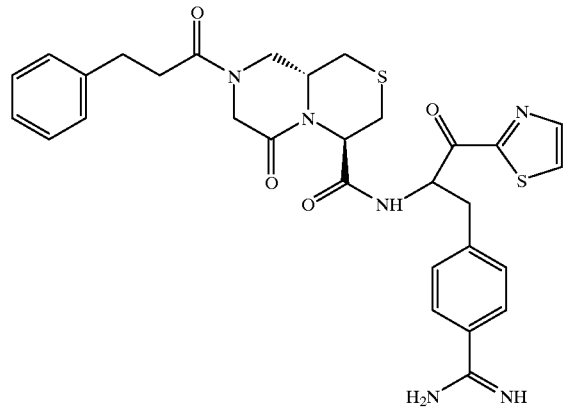 |
| 0785 | 5-Oxo-7-(3-phenyl-propionyl)-octahydro-2-thia-4a,7-diaza-naphthalene-4-carboxylic acid [1-(3-carbaminidoyl-benzyl)-2-oxo-2-thiazol-2-yl-ethyl]-amide | 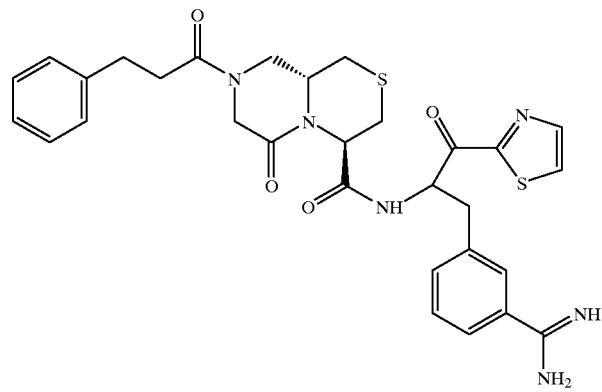 |
| 0790 | 5-Oxo-7-(3-phenyl-propionyl)-octahydro-2-thia-4a,7-diaza-naphthalene-4-carboxylic acid [1-(1-carbamimidoyl-piperidin-3-ylmethyl)-2-oxo-2-thiazol-2-yl-ethyl]-amide | 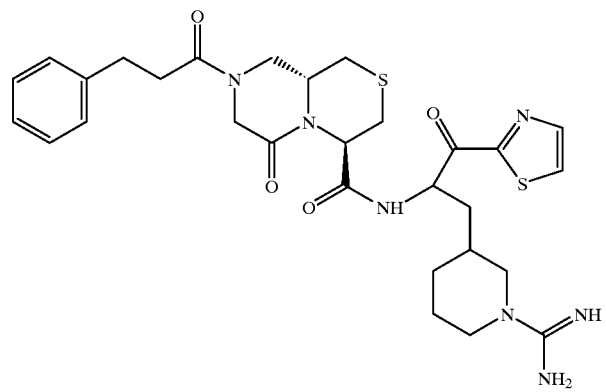 |

| | | |
|---|---|---|
| 0795 | 5-Oxo-7-(3-phenyl-propionyl)-octahydro-2-thia-4a,7-diaza-naphthalene-4-carboxylic acid [1-(1-carbamimidoyl-piperidin-4-ylmethyl)-2-oxo-2-thiazol-2-yl-ethyl]-amide | 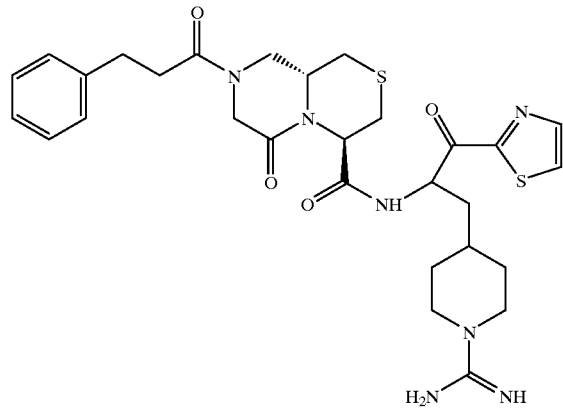 |
| 0800 | [4-[4-Guanidino-1-(thiazole-2-carbonyl)-butylcarbamoyl]-5-oxo-7-(3-phenyl-propionyl)-octahydro-2-thia-4a,7-diaza-naphthalen-6-yl]-acetic acid | 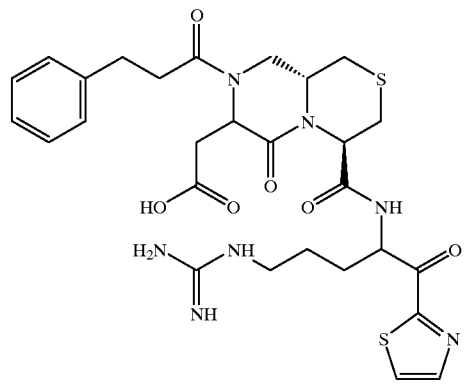 |
| 0805 | 5-Oxo-7-(3-phenyl-propionyl)-octahydro-2-thia-4a,7-diaza-naphthalene-4-carboxylic acid [4-guanidino-1-(thiazole-2-carbonyl)-butyl]-amide | 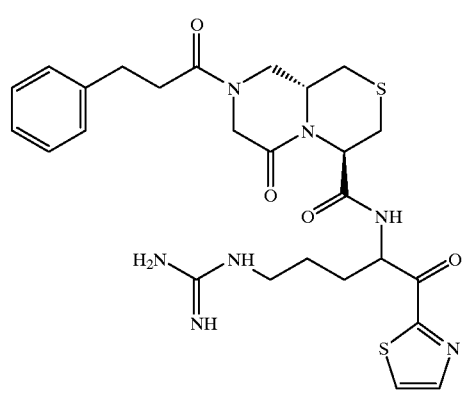 |

| | | |
|---|---|---|
| 0810 | 3-[4-[4-Guanidino-1-(thiazole-2-carbonyl-butylcarbamoyl]-5-oxo-7-(3-phenyl-propionyl)-octahydro-2-thia-4a,7-diaza-naphthalen-6-yl]-propionic acid | 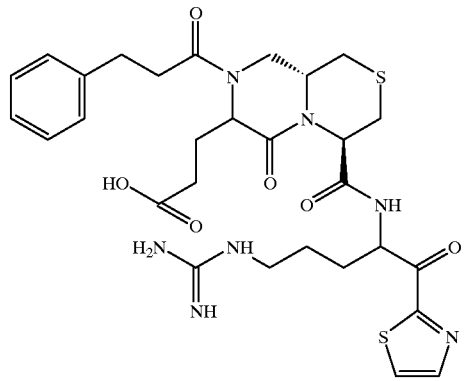 |
| 0815 | 5-Oxo-7-(3-phenyl-propionyl)-octahydro-2-thia-4a,7-diaza-naphthalene-4-carboxylic acid [3-guanidino-propyl]-amide | 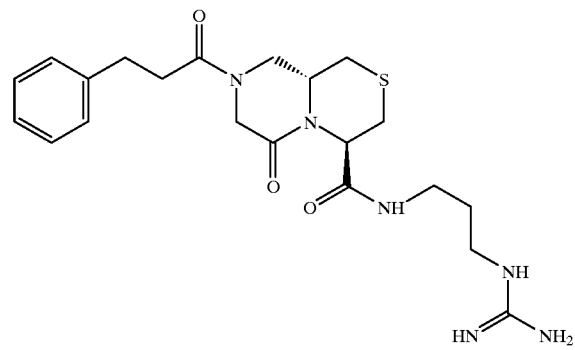 |
| 0820 | 5-Oxo-7-(3-phenyl-propionyl)-octahydro-2-thia-4a,7-diaza-naphthalene-4-carboxylic acid [1-(1-carbamimidoyl-piperidin-3-ylmethyl)-2-oxo-2-thiazol-2-yl-ethyl]-amide | 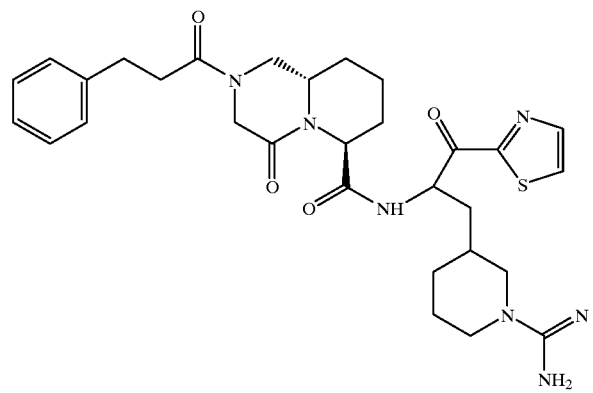 |
| 0825 | 4-Oxo-2-(3-phenyl-propionyl)-octahydro-pyrrolo[1,2-a]pyrazine-6-carboxylic acid[4-guanidino-1-(hydroxy-thiazol-2-yl-methyl)-butyl]-amide | 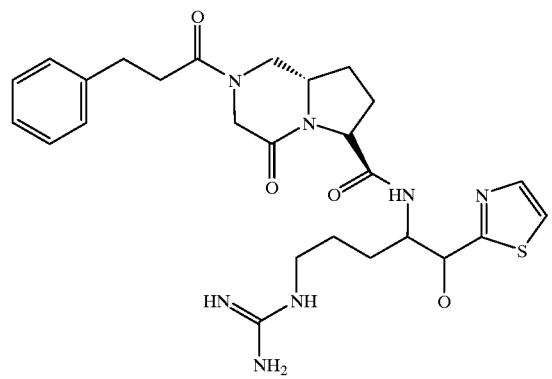 |

| | | |
|---|---|---|
| 0830 | 4-Oxo-2-(3-phenyl-propionyl)-octahydro-pyrrolo[1,2-a]pyrazine-6-carboxylic acid(4-guanidino-1-thiazol-2-ylmethyl-butyl)-amide | 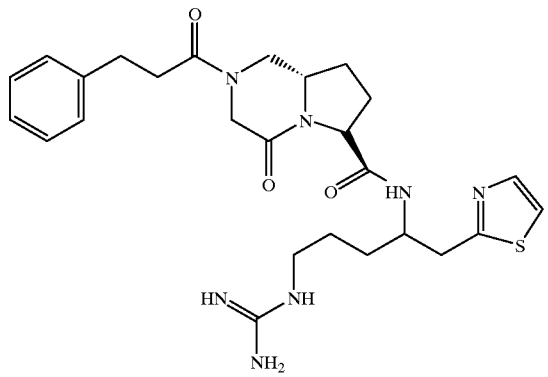 |
| 0835 | 4-Oxo-2-(3-phenyl-propionyl)-octahydro-pyrrolo[1,2-a]pyrazine-6-carboxylic acid[4-guanidino-1-thiazol-2-yl-butyl)-amide | 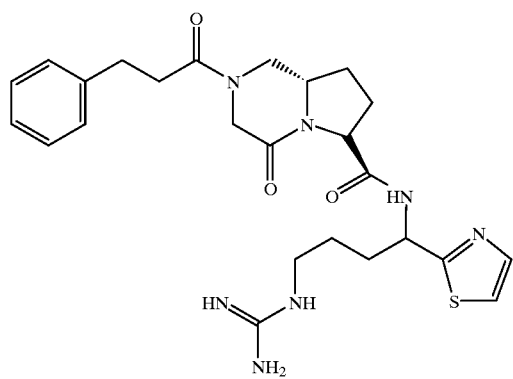 |
| 0840 | 4-oxo-2-(3-phenyl-propionyl)-octahydro-pyrrolo[1,2-a]pyrazine-6-carboxylic acid[4-methoxy-1-(thiazole-2-carbonyl)-butyl]-amide | 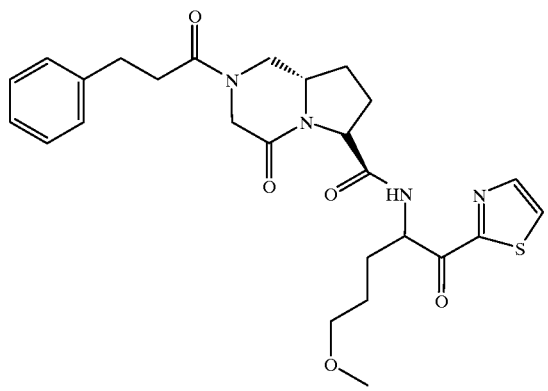 |
| 0845 | [6-[4-Methoxy-1-(thiazole-2-carbonyl)-butylcarbamoyl]-4-oxo-2-(3-phenyl-propionyl)-octahydro-pyrrolo[1,2-a]pyrazin-3-yl]-acetic acid | 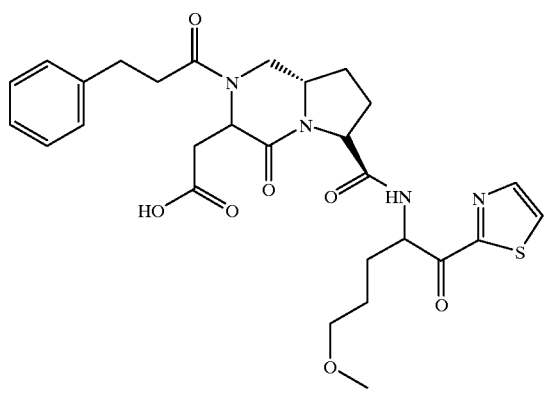 |

| | | |
|---|---|---|
| 0850 | [2-(5-Methoxy-2-([4-oxo-2-(3-phenyl-propionyl)-octahydro-pyrrolo[1,2-a]pyrazine-6-carbonyl]-amino)-pentanoyl)-thiazol-5-yl]-acetic acid | 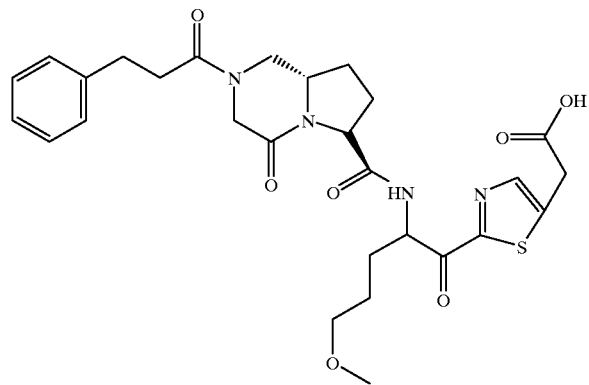 |
| 0855 | 4-Oxo-2-(3-phenyl-propionyl)-octahydro-pyrrolo[1,2-a]pyrazine-6-carboxylic acid[4-amino-1-(thiazole-2-carbonyl)-butyl]-amide | 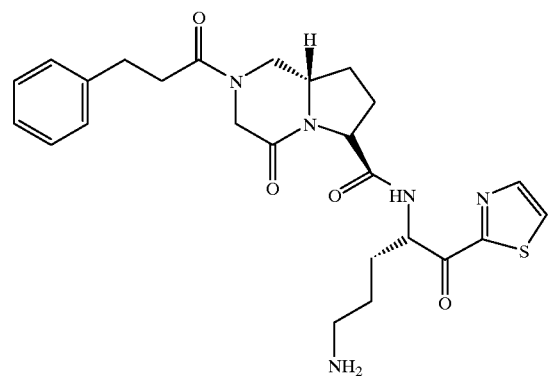 |
| 0860 | 4-Oxo-2-(3-phenyl-propionyl)-octahydro-pyrrolo[1,2-a]pyrazine-6-carboxylic acid[5-amino-1-(thiazole-2-carbonyl)-pentyl]-amide | 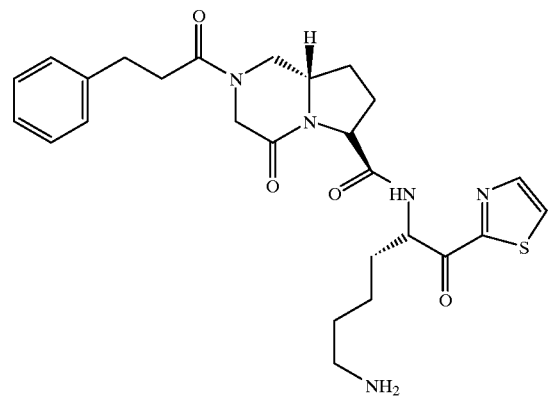 |

-continued

| 0865 | 4-Oxo-2-(3-phenyl-propionyl)-octahydro-pyrrolo[1,2-a]pyrazine-6-carboxylic acid[5-guanidino-1-(thiazole-2-carbonyl)-pentyl]-amide | 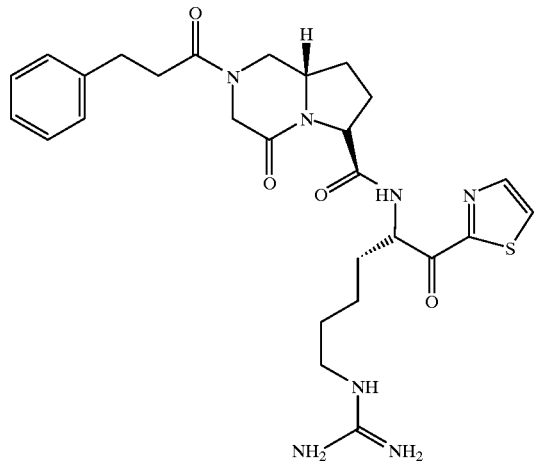 |

| 0870 | 2-(3-Naphthalen-2-yl-propionyl)-4-oxo-octahydro-pyrrolo[1,2-a]pyrazine-6-carboxylic acid[4-guanidino-1-(thiazole-2-carbonyl)-butyl]-amide | 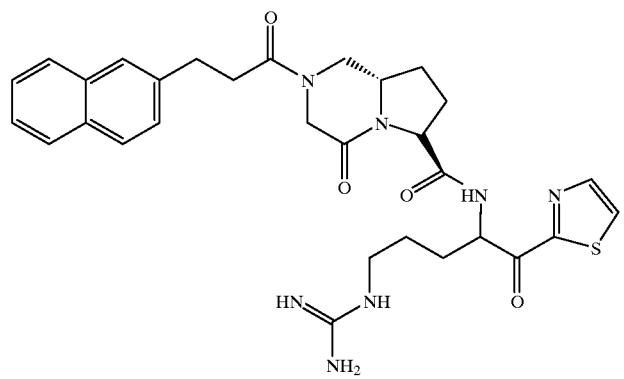 |

| 0875 | 4-Oxo-2-(3-phenyl-propionyl)-octahydro-pyrrolo[1,2-a]pyrazine-6-carboxylic acid[4-guanidino-1-(1-methyl-1H-imidazole-2-carbonyl)-butyl]-amide | 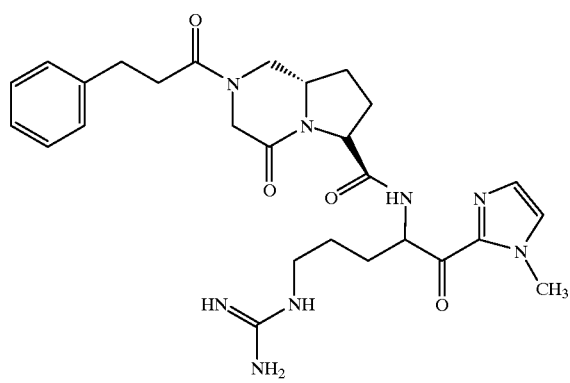 |

-continued 0880 4-Oxo-2-(3-phenyl-propionyl)-octahydro-pyrrolo[1,2-a]pyrazine-6-carboxylic acid[4-guanidino-1-(thiazole-2-carbonyl)-butyl]-amide

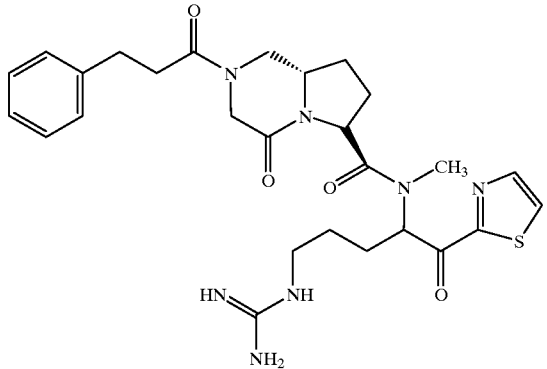

0885 8,8-Dimethyl-4-oxo-2-(3-phenyl-propionyl)-octahydro-pyrrolo[1,2-a]pyrazine-6-carboxylic acid[4-guanidino-1-(thiazole-2-carbonyl)-butyl]-amide

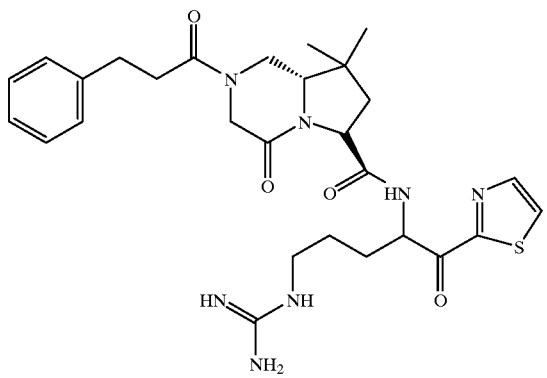

Preferred compounds according to formula (VIII) include:
0325 3-Aminomethyl-2-benzoyl-4-oxo-octahydro-pyrrolo[1,2-a]pyridine-6-carboxylic acid [1-(benzothiazole-2-carbonyl)-4-guanidino-butyl]-amide
0330 3-Aminomethyl-4-oxo-2phenylacetyl-octahydro-pyrrolo[1,2-a]pyrazine-6-carboxylic acid [1-(benzothiazole-2-carbonyl)-4-guanidino-butyl]-amide
0515 4-Oxo-2-(3-phenyl-propionyl)-octahydro-pyrrolo[1,2-a]pyrazine-6-carboxylic acid [1-(3-carbamimidoyl-benzyl)-2-oxo-2-thiazol-2-yl-ethyl]-amide
0530 4-Oxo-2-(3-phenyl-propionyl)-octahydro-pyrrolo[1,2-a]pyrazine-6-carboxylic acid [1-(1-carbamimidoyl-piperidin-2-ylmethyl)-2-oxo-2-thiazol-2-yl-ethyl]-amide
0545 [6-[1-(1-Carbamimidoyl-piperidin-4-ylmethyl)-2-oxo-2-thiazol-2-yl-ethylcarbamoyl]-4-oxo-2-(3-phenyl-propionyl)-octahydro-pyrrolo[1,2-a]pyrazin-3-yl)-acetic acid
0550 3-[6-[1-(1-Carbamimidoyl-piperidin-4-ylmethyl)-2-methyl)-2-oxo-2-thiazol-2-yl-ethylcarbamoyl]-4-oxo-2-(3-phenyl-propionyl)-octahydro-pyrrolo[1,2-a]pyrazin-3-yl)-acetic acid
0555 [6-[1-(1-Carbamimidoyl-piperidin-3-ylmethyl)-2-oxo-2-thiazol-2-yl-ethylcarbamoyl]-4-oxo-2-(3-phenyl-propionyl)-octahydro-pyrrolo[1,2-a]pyrazin-3-yl)-acetic acid
0560 [6-(3-Guanidino-propylcarbamoyl)-4-oxo-2-(3-phenyl-propionyl)-octahydro-pyrrolo[1,2-a]pyrazin-3-yl)-acetic acid
0565 3-[6-(3-Guanidino-propylcarbamoyl)-4-oxo-2-(3-phenyl-propionyl)-octahydro-pyrrolo[1,2-a]pyrazin-3-yl)-propionic acid
0575 4-Oxo-2-(3-phenyl-propionyl)-octahydro-pyrrolo[1,2-]pyrazine-6-carboxylic acid [1-(1-carbamimidoyl-piperidin-4-ylmethyl)-2-oxo-2-thiazol-2-yl-ethyl]-methyl-amide
0580 [6-([1-Carbamimidoyl-piperidin-4-ylmethyl)-2-oxo-2-thiazol-2-yl-ethyl]-methyl-carbamoyl)-4-oxo-2-(3-phenyl-propionyl)-octahydro-pyrrolo[1,2-a]pyrazin-3-yl]-acetic acid
0585 4-Oxo-2-(3-phenyl-propionyl)-octahydro-pyrrolo[1,2-a]pyrazine-6-carboxylic acid [1-(1-carbamimidoyl-piperidin-3-ylmethyl)-2-oxo-2-thiazol-2-yl-ethyl]-methyl-amide
0590 4-Oxo-2-(3-phenyl-propionyl)-octahydro-pyrrolo[1,2-a]pyrazine-6-carboxylic acid (3-guanidino-propyl)-methyl-amide
0595 2-(Naphthalene-2-carbonyl)-4-oxo-octahydro-pyrrolo[1,2-a]pyrazine-6-carboxylic acid [4-guanidino-1-(thiazole-2-carbonyl)-butyl]-amide
0625 2-[2-(2-Methyl-benzylidene)-but-3-enoyl]-4-oxo-octahydro-pyrrolo[1,2-a]pyrazine-6-carboxylic acid [1-(1-carbamimidoyl-piperidin-3-ylmethyl)-2-oxo-2-thiazol-2-yl-ethyl]-amide
0630 2-[2-(2-Methyl-benzylidene)-but-3-enoyl]-4-oxo-octahydro-pyrrolo[1,2-a]pyrazine-6-carboxylic acid [1-(1-carbamimidoyl-piperidin-4-ylmethyl)-2-oxo-2-thiazol-2-yl-ethyl]-amide
0635 2-(2-Benzylidene-pent-3-enoyl)-4-oxo-octahydro-pyrrolo[1,2-a]pyrazine-6-carboxylic acid (3-guanidino-propyl)-amide
0625 2-[2-(2-Methyl-benzylidene-but-3-enoyl]-4-oxo-octahydro-pyrrolo[1,2-a]pyrazine-6-carboxylic acid [1-(1-carbamimidoyl-piperidin-3-ylmethyl)-2-oxo-2-thiazol-2-yl-ethyl]-amide 0630 2-[2-(2-Methyl-benzylidene-but-3-enoyl]-4-oxo-octahydro-pyrrolo[1,2-a]pyrazine-6-carboxylic acid [1-(1-carbamimidoyl-piperidin-4-ylmethyl)-2-oxo-2-thiazol-2-yl-ethyl]-amide 0635 2-(2-Benzylidene-pent-3-enoyl)-4-oxo-octahydro-pyrrolo[1,2-a]pyrazine-6-carboxylic acid (3-guanidino-propyl)-amide 0645 4-Oxo-2-(3-phenyl-propionyl)-octahydro-pyrrolo[1,2-a]pyrazine-6-carboxylic acid [4-imidazol-1-yl-1-(thiazole-2-carbonyl)-butyl]-amide 0670 4-Oxo-2-(3-phenyl-propionyl)-octahydro-pyrrolo[1,2-a]pyrazine-6-carboxylic acid [3-(2-amino-6-chloro-pyrimidin-4-yl)-1-(thiazole-2-carbonyl)-propyl]-amide 0675 4-Oxo-2-(3-phenyl-propionyl)-octahydro-pyrrolo[1,2-a]pyrazine-6-carboxylic acid [3-(6-amino-pyridin-2-yl)-1-(thiazole-2-carbonyl)-propyl]-amide 0680 4-Oxo-2-(3-phenyl-propionyl)-octahydro-pyrrolo[1,2-a]pyrazine-6-carboxylic acid [3-(2-amino-pyridin-4-yl)-1-(thiazole-2-carbonyl)-propyl]-amide 0685 4-Oxo-2-(3-phenyl-propionyl)-octahydro-pyrrolo[1,2-a]pyrazine-6-carboxylic acid [2-(2-amino-pyridin-4-yl)-1-(thiazole-2-carbonyl)-ethyl]-amide 0690 4-Oxo-2-(3-phenyl-propionyl)-octahydro-pyrrolo[1,2-a]pyrazine-6-carboxylic acid [2-(6-amino-pyridin-2-yl)-1-(thiazole-2-carbonyl)-ethyl]-amide 0695 2-[4-Oxo-2-(3-phenyl-propionyl)-octahydro-pyrrolo[1,2-a]-pyrazine-6-carbonyl]-3-thiazole-2-carbonyl)-1,2,3,4-tetrahydro-isoquinoline-6-carboxamidine 0700 2-[4-Oxo-2-(3-phenyl-propionyl)-octahydro-pyrrolo[1,2-a]-pyrazine-6-carbonyl]-3-thiazole-2-carbonyl)-1,2,3,4-tetrahydro-isoquinoline-7-carboxamidine 0705 N-[1-[4-Oxo-2-(3-phenyl-propionyl)-octahydro-pyrrolo[1,2-a]pyrazine-6-carbonyl]-5-(thiazole-2-carbonyl)-pyrrolidin-3-yl]-guanidine 0710 4-Oxo-2-(3-phenyl-propionyl)-octahydro-pyrrolo[1,2-a]pyrazine-6-carboxylic acid [1-(4-amino-cyclohexyl)-2-oxo-2-thiazol-2-yl-ethyl]-amide 0730 4-Oxo-2-(3-phenyl-propionyl)-octahydro-pyrrolo[1,2-a]pyrazine-6-carboxylic acid [1-(3-aminomethyl-benzyl)-2-oxo-2-thiazol-2-yl-ethyl]-amide 0745 4-Oxo-2-(3-phenyl-propionyl)-octahydro-pyrrolo[1,2-a]pyrazine-6-carboxylic acid [1-(3-guanidino-cyclohexylmethyl)-2-oxo-2-thiazol-2-yl-ethyl]-amide 0755 4-Oxo-2-(3-phenyl-propionyl)-octahydro-pyrrolo[1,2-a]pyrazine-6-carboxylic acid [1-(2-guanidino-cyclohexylmethyl)-2-oxo-2-thiazol-2-yl-ethyl]-amide 0795 5-Oxo-7-(3-phenyl-propionyl)-octahydro-2-thia-4a,7-diaza-naphthalene-4-carboxylic acid [1-(1-carbamimidoyl-piperidin-4-ylmethyl)-2-oxo-2-thiazol-2-yl-ethyl]-amide 0800 [4-[4-Guanidino-1-(thiazole-2-carbonyl)-butylcarbamoyl]-5-oxo-7-(3-phenyl-propionyl)-octahydro-2-thia-4a,7-diaza-naphthalene-6-yl]-acetic acid 0810 [3-[4-Guanidino-1-(thiazole-2-carbonyl)-butylcarbamoyl]-5-oxo-7-(3-phenyl-propionyl)-octahydro-2-thia-4a,7-diaza-naphthalene-6-yl]-propionic acid 0815 5-Oxo-7-(3-phenyl-propionyl)-octahydro-2-thia-4a,7-diaza-naphthalene-4-carboxylic acid [3-guanindino-propyl]-amide 0820 5-Oxo-7-(3-phenyl-propionyl)-octahydro-2-thia-4a,7-diaza-naphthalene-4-carboxylic acid [1-(1-carbamimidoyl-piperidin-3-ylmethyl)-2-oxo-2-thiazol-2-yl-ethyl]-amide 0830 4-Oxo-2-(3-phenyl-propionyl)-octahydro-pyrrolo[1,2-a]pyrazine-6-carboxylic acid (4-guanidino-1-thiazol-2-ylmethyl-butyl)-amide 0835 4-Oxo-2-(3-phenyl-propionyl)-octahydro-pyrrolo[1,2-a]pyrazine-6-carboxylic acid [4-guanidino-1-thiazol-2-yl-butyl)-amide.

More preferred compounds according to formula VIII include:

0335 2-Benzoyl-4-oxo-octahydro-pyrrolo[1,2-a]pyrazine-6-carboxylic acid [4-guanidino-1-(thiazole-2-carbonyl)-butyl]-amide 0650 4-Oxo-2-(3-phenyl-propionyl)-octahydro-pyrrolo[1,2-a]pyrazine-6-carboxylic acid [4-(2-amino-imidazol-1-yl)-1-(thiazole-2-carbonyl)-butyl]-amide 0655 4-Oxo-2-(3-phenyl-propionyl)-octahydro-pyrrolo[1,2-a]pyrazine-6-carboxylic acid [3-(2-amino-6-methyl-pyrimidin-4-yl)-1-(thiazole-2-carbonyl)-propyl]-amide 0715 4-Oxo-2-(3-phenyl-propionyl)-octahydro-pyrrolo[1,2-a]pyrazine-6-carboxylic acid [1-(4-amino-cyclohexylmethyl)-2-oxo-2-thiazol-2-yl-ethyl]-amide 0720 4-Oxo-2-(3-phenyl-propionyl)-octahydro-pyrrolo[1,2-a]pyrazine-6-carboxylic acid [1-(4-amino-benzyl)-2-oxo-2-thiazol-2yl-ethyl]-amide 0725 4-Oxo-2-(3-phenyl-propionyl)-octahydro-pyrrolo[1,2-a]pyrazine-6-carboxylic acid [1-(4-aminomethyl-benzyl)-2-oxo-2-thiazol-2yl-ethyl]-amide 0735 4-Oxo-2-(3-phenyl-propionyl)-octahydro-pyrrolo[1,2-a]pyrazine-6-carboxylic acid (2-oxo-1-piperidin-4-ylmethyl-2-thiazol-2-yl-ethyl)-amide 0740 4-Oxo-2-(3-phenyl-propionyl)-octahydro-pyrrolo[1,2-a]pyrazine-6-carboxylic acid (2-oxo-1-piperidin-34-yl-2-thiazol-2-yl-ethyl)-amide 0750 4-Oxo-2-(3-phenyl-propionyl)-octahydro-pyrrolo[1,2-a]pyrazine-6-carboxylic acid [1-(4-guanidino-cyclohexylmethyl)-2-oxo-2-thiazol-2-yl-ethyl]-amide 0760 4-Oxo-2-(3-phenyl-propionyl)-octahydro-pyrrolo[1,2-a]pyrazine-6-carboxylic acid [1-(5-benzyl-thiazole-2-carbonyl)-4-guanidino-butyl]-amide 0765 4-Oxo-2-(3-phenyl-propionyl)-octahydro-pyrrolo[1,2-a]pyrazine-6-carboxylic acid [4-guanidino-1-(5-phenyl-thiazole-2-carbonyl)-butyl]-amide 0770 4-Oxo-2-(3-phenyl-propionyl)-octahydro-pyrrolo[1,2-a]pyrazine-6-carboxylic acid [4-guanidino-1-(thiazole-2-carbonyl)-butyl]-amide 0775 5-Oxo-7-(3-phenyl-propionyl)-octahydro-2-thia-4a,7-diaza-naphthalene-4-carboxylic acid [4-guanidino-1-(thiazole-2-carbonyl)-butyl]-amide 0780 5-Oxo-7-(3-phenyl-propionyl)-octahydro-2-thia-4a,7-diaza-naphthalene-4-carboxylic acid [1-(4-carbamimidoyl-benzyl)-2-oxo-2-thiazol-2-yl-ethyl]-amide 0785 5-Oxo-7-(3-phenyl-propionyl)-octahydro-2-thia-4a,7-diaza-naphthalene-4-carboxylic acid [1-(3-carbamimidoyl-benzyl)-2-oxo-2-thiazol-2-yl-ethyl]-amide 0790 5-Oxo-7-(3-phenyl-propionyl)-octahydro-2-thia-4a,7-diaza-naphthalene-4-carboxylic acid [1-(1-carbamimidoyl-piperidin-3-ylmethyl)-2-oxo-2-thiazol-2-yl-ethyl]-amide 0805 5-Oxo-7-(3-phenyl-propionyl)-octahydro-2-thia-4a,7-diaza-naphthalene-4-carboxylic acid [4-guanidino-1-(thiazole-2-carbonyl)-butyl]-amide 0825 4-Oxo-2-(3-phenyl-propionyl)-octahydro-pyrrolo[1,2-a]pyrazine-6-carboxylic acid [4-guanidino-1-(hydroxy-thiazol-2-yl-methyl)-butyl]-amide 0840 4-Oxo-2-(3-phenyl-propionyl)-octahydro-pyrrolo[1,2-a]pyrazine-6-carboxylic acid [4-methoxy-1-(thiazol-2-carbonyl)-butyl]-amide 0845 [6-[4-Methoxy-1-(thiazole-2-carbonyl)-butylcarbamoyl]-4-oxo-2-(3-phenyl-propionyl)-octahydro-pyrrolo[1,2-a]pyrazin-3-yl]-acetic acid 0850 [2-(5-Methoxy-2-([4-oxo-2-(3-phenyl-propionyl)-octahydro-pyrrolo[1,2-a]pyrazine-6-carbonyl]-amino)-pentanoyl)-thiazol-5-yl]-acetic acid 0855 4-Oxo-2-(3-phenyl-propionyl)-octahydro-pyrrolo[1,2-a]pyrazine-6-carboxylic acid [4-amino-1-(thiazole-2-carbonyl)-butyl]-amide 0860 4-Oxo-2-(3-phenyl-propionyl)-octahydro-pyrrolo[1,2-a]pyrazine-6-carboxylic acid [5-amino-1-(thiazole-2-carbonyl)-pentyl]-amide 0865 4-Oxo-2-(3-phenyl-propionyl)-octahydro-pyrrolo[1,2-a]pyrazine-6-carboxylic acid [5-guanidino-1-(thiazole-2-carbonyl)-pentyl]-amide.

Most preferred compounds according to formula VIII include:

0345 4-Oxo-2-(3-phenyl-propionyl)-octahydro-pyrrolo[1,2-a]pyrazine-6-carboxylic acid [4-guanidino-1-(5-methyl-thiazole-2-carbonyl)-butyl]-amide; and 0340 4-Oxo-2-(3-phenyl-propionyl)-octahydro-pyrrolo[1,2-a]-pyrazine-6-carboxylic acid [4-guanidino-1-(thiazole-2-carbonyl)-butyl]-amide.

Preferred compounds according to formula IX include:

0890  3-Amino-4-oxo-2-phenyl-hexahydro-pyrrolo[2,1-b][1,3]thiazine-6-carboxylic acid[1-(benzothiazole-2-carbonyl)-4-guanidino-butyl]-amide

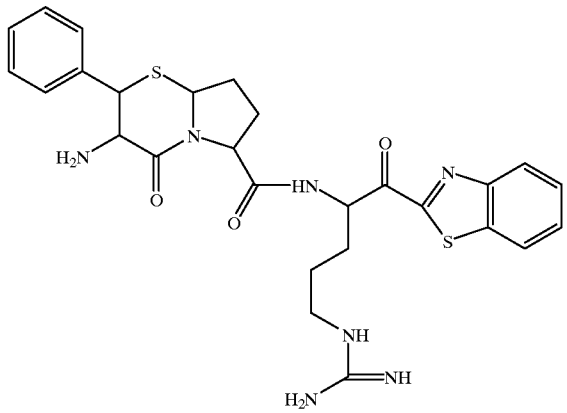

0895  3-Amino-2-benzyl-4-oxo--hexahydro-pyrrolo[2,1-b][1,3]thiazine-6-carboxylic acid[1-(benzothiazole-2-carbonyl)-4-guanidino-butyl]-amide

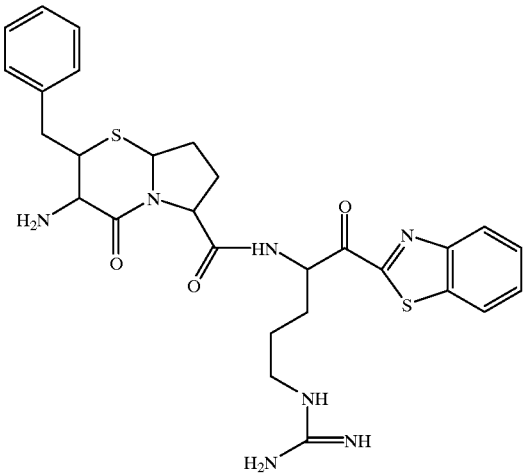

| 0900 | 3-Amino-2-cyclohexyl-4-oxo-hexahydro-pyrrolo[2,1-b][1,3]thiazine-6-carboxylic acid[1-(benzothiazole-2-carbonyl)-4-guanidino-butyl]-amide | 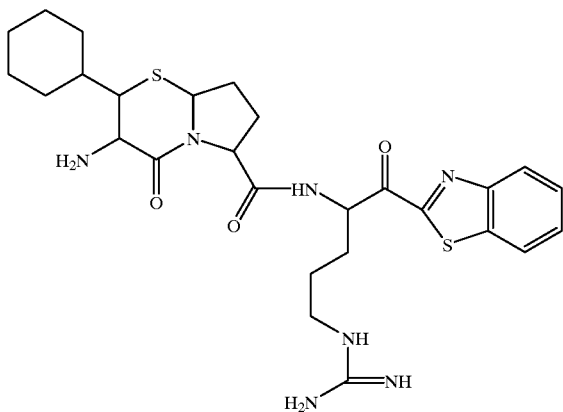 |

Preferred compounds according to formula X include:

| 0905 | 7-Benzyl-6-oxo-octahydro-pyrido[2,1-c][1,4]thiazine-4-carboxylic acid[1-(benzothiazole-2-carbonyl)-4-guanidino-butyl]-amide | 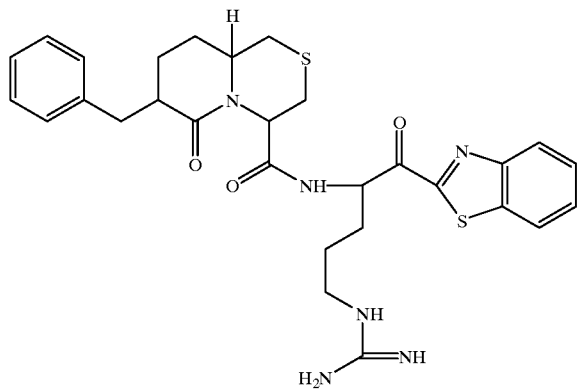 |

| 0910 | 7-(4-tert-Butyl-benzyl)-6-oxo-octahydro-pyrido[2,1-c][1,4]thiazine-4-carboxylic acid [1-(benzothiazole-2-carbonyl)-4-guanidino-butyl]-amide | 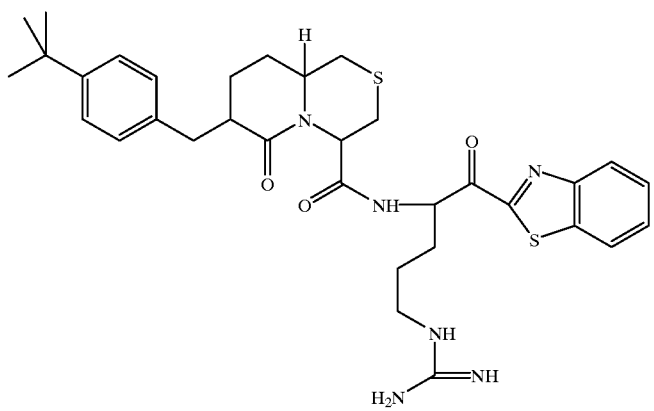 |

| | | |
|---|---|---|
| 0915 | 6-Oxo-octahydro-pyrido[2,1-c][1,4]thiazine-4-carboxylic acid[4-guanidino-1-(thiazole-2-carbonyl)-butyl]-amide | 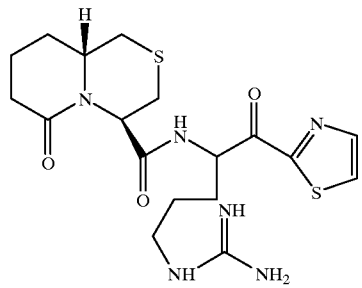 |
| 0925 | 7-Benzyl-6-oxo-octahydro-pyrido[2,1-c][1,4]thiazine-4-carboxylic acid[4-guanidino-1-(thiazole-2-carbonyl)butyl]-amide | 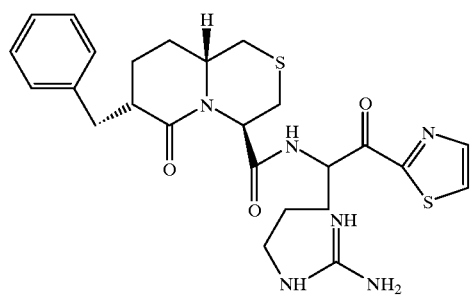 |
| 0935 | 7-Benzyl-6-oxo-octahydro-pyrido[2,1-c][1,4]thiazine-4-carboxylic acid[4-guanidino-1-(thiazole-2-carbonyl)butyl]-amide | 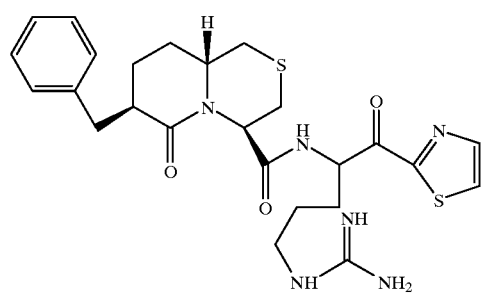 |
| 0940 | 6-Oxo-7-phenethyl-octahydro-pyrido[2,1-c][1,4]thiazine-4-carboxylic acid[4-guanidino-1-(thiazole-2-carbonyl)-butyl]-amide | 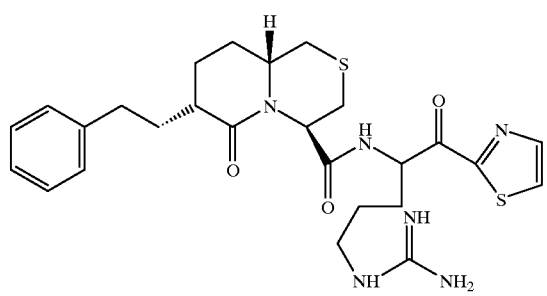 |
| 0950 | 7-Benzyl-2,2,6-trioxo-octahydro-2 1>6_pyrido[2,1-c][1,4]thiazine-4-carboxylic acid[4-guanidino-1-(thiazole-2-carbonyl)-butyl]-amide | 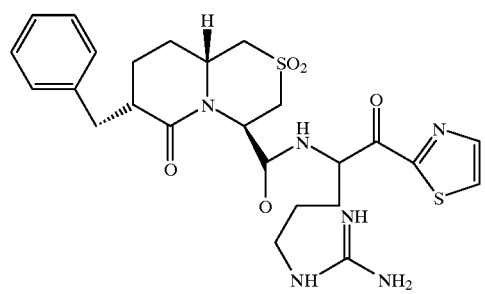 |

More preferred compounds according to formula X include: 925 7-Benzyl-6-oxo-octahydro-pyrido[2,1-c][1,4]thiazine-4-carboxylic acid [4-guanidino-1-(thiazole-2-carbonyl)butyl]-amide; and 940 6-Oxo-7-phenethyl-octahydro-pyrido[2,1-c][1,4]thiazine-4-carboxylic acid [4-guanidino-1-(thiazole-2-carbonyl)-butyl]-amide.

Preferred compounds according to formula III include:

0960 4-oxo-1-(3-phenyl-propionyl)-octahydropyrrolo[1,2]pyrimidine-6-carboxylic acid[4-guanidino-1-(thiazole-2-carbonyl)-butyl]-amide

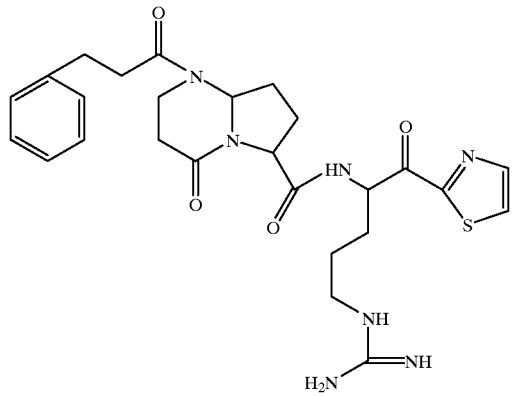

0965 4-oxo-1-(phenethylsulfonyl)-octahydropyrrolo[1,2]pyrimidine-6-carboxylic acid[4-guanidino-1-(thiazole-2-carbonyl)-butyl]-amide

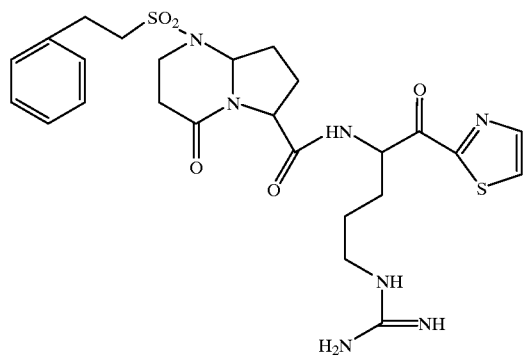

For preparation of the compounds of formula (VII) various methods can be employed depending upon the particular starting materials and/or intermediates involved. The following scheme is one particular method of preparation.

SCHEME 1

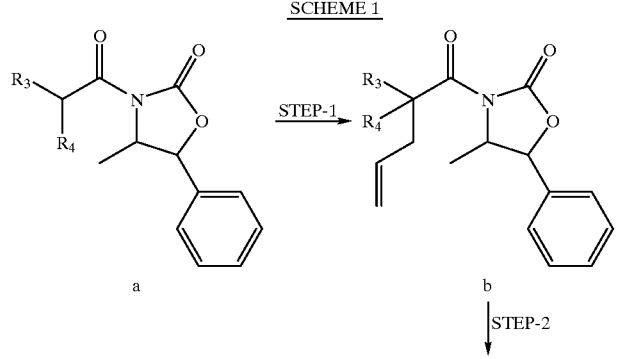

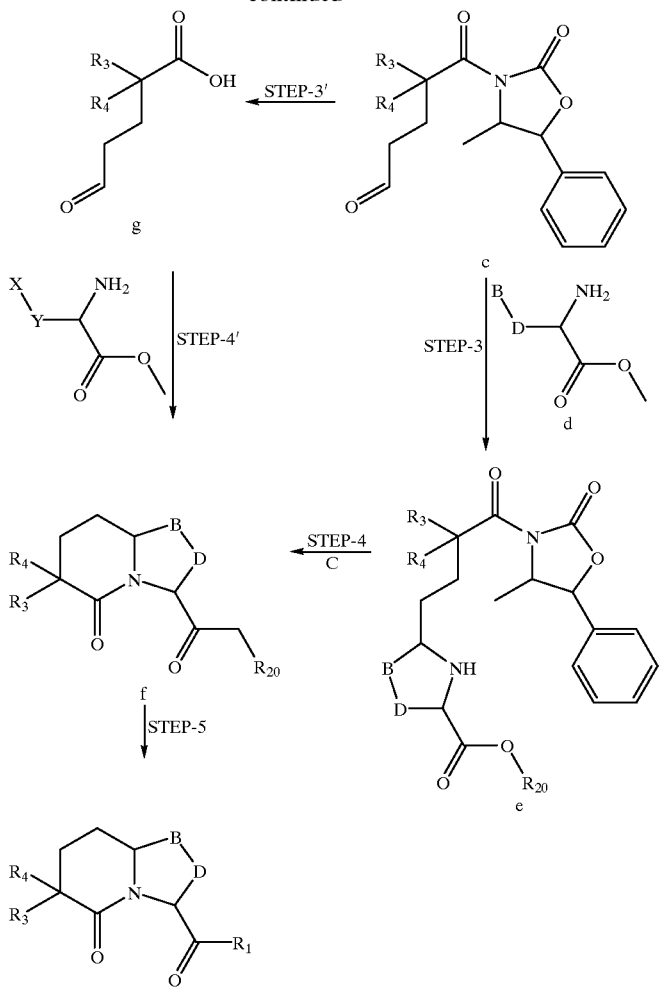

Step 1:

The alkylation of a is done with appropriate bases according to the procedure described in Evans et al (J. Am. Chem. Soc., 1981, 103, 2127; ibid, 1982, 104, 1737; Aldrichimica Acta, 1982, 15, 23) to give b.

Step 2:

Compound b upon hydroboration and oxidation following conditions available in the literature (Synthesis, 1980, 151) results in the aldehyde c.

Step 3:

The formation of adduct e from aldehyde c with d is done by stirring the reactant in aromatic solvents e.g. benzene or toluene in presence of catalytic amount of suitable acid e.g, p-toluenesulfonic acid.

Step 3':

The inter conversion of aldehyde c to aldehyde g is readily achieved by appropriate protection deprotection protocals found in T. Greene, Protective Groups in Organic Synthesis, (John Wiley & Sons, 1981).

Step 4:

The cylization of adduct e to f may readily be achieved by appropriate Lewis acids e.g, trimethyl aluminum in suitable solvents e.g. dichloromethane, the methodology found in T. Greene, supra.

Step 4':

Alternatively, the compound f can be derived from the treatment of aldehyde g with d in presence of suitable aromatic solvents e.g, benzene.

Step 5:

The ester function (—CO(O)O—$R_{20}$) of the bicyclic intermediate of formula f is then subjected to hydrolysation using an appropriate agent such as HCl in an appropriate solvent such as ethyl ether to yield to the free carboxylic acid. The resulting compound is then coupled to $R_1H$ with a peptide coupling agent such as BOP in an appropriate solvent such as DMF to yield a bicyclic coupled compound of formula (VIII). Suitable conditions for peptide bond formation are well known in th art of peptide chemistry. For example see *Principles of Peptide Synthesis*, Bodanszky M., Springer-Verlag, Berlin, Heidelberg, New York, Tokyo 1984; and *The Peptides, Analysis, Synthesis, Biology, Vol. 1*, edited by Gross E., and Meienhofer J., Academic Press, New York, San Francisco, London, 1979.

For preparation of the compounds of formula (VIII) various methods can be employed depending upon the particular starting materials and/or intermediates involved. The following scheme is one particular method of preparation.

SCHEME 2

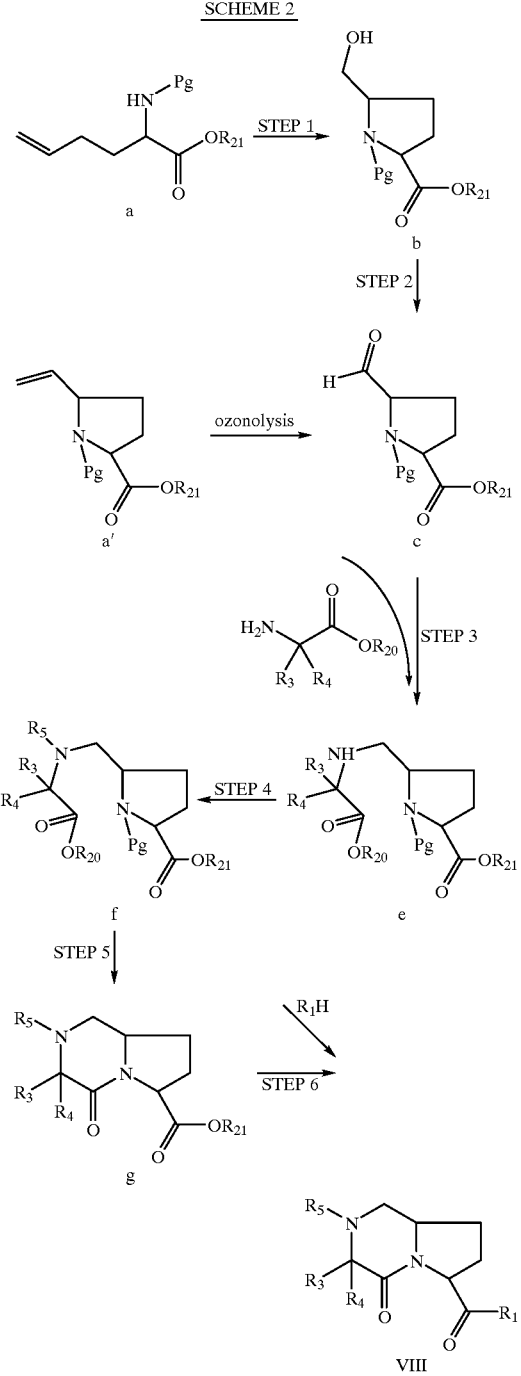

wherein:

Pg is a nitrogen protecting group;
each of $R_{20}$; and $R_{21}$ is independently a $C_{1-6}$ alkyl; and X, $R_1$, $R_3$, $R_4$ and $R_5$ are as previously defined.

The process in scheme 2 is briefly described as follows:

STEP 1:

The amino and carboxylic functions of the unsaturated compound of formula (a) are protected with appropriate protecting groups. A variety of protecting groups known for reactive functional groups and suitable protection and deprotection protocols may be found in T. Greene, *Protective Groups In Organic Synthesis*, (John Wiley & Sons, 1981). The appropriate protecting group to use in a particular synthetic scheme will depend on many factors, including the presence of other reactive functional groups and the reaction conditions desired for removal. The unsaturated compound of formula is easily obtained by methods and protocols known to chemist skill on the art. The protected unsaturated compound of formula (a) is subjected to appropriate conditions to allow cyclisation using an appropriate reagent such as mercuric acetic in an inert solvent such as tetrahydrofuran (THF) to yield to a protected amino alcohol of formula (b).

STEP 2

The protected amino alcohol of formula (b) is oxidized using an appropriate oxidizing agent such as sulfur trioxide pyridine complex in an appropriate solvent such as diclhoromethane or dimethylformamide to yield to a protected amino aldehyde of formula (c). Alternatively, intermediate (C) can be made by the ozonolysis of a compound of formula (a') prepared according to Collado et al, J. Org. Chem., 1995, 60:5011.

STEP 3

The protected amino aldehyde of formula (c) is coupled with an amino acid alkyl ester of formula (d) by first forming the imine followed by contacting the obtained imine with an appropriate reagent such as sodium triacetoxy borohydride $NaBH(OAc)_3$ to yield to a cyclic intermediate of formula (e).

STEP 4

The cyclic intermediate of formula (e) is functionalized at the amino position to yield to the amino substituted cyclic intermediate of formula (f). Conditions appropriate for such reactions are well known in the art and will depend on the nature of the $R_5$ substituent.

STEP 5

The amino protecting group of the cyclic intermediate of formula (f) is removed under appropriate conditions and the resulting compound is then subjected to appropriate condition for internal ring closure such as low heat in an inert solvent or as a raw compound to yield to a bicyclic intermediate of formula (g). The bicyclic intermediate of formula (g) can also be obtained by hydrolysing the ester function (—C(O)O—$R_{20}$) of the cyclic intermediate of formula (g) to the free carboxylic acid followed by standard peptide coupling using an appropriate coupling reagent such as benzotriazole-1-yloxy-tris-(dimethylamino)phosphonium hexafluorophosphate (BOP) in an inert solvent such as dimethyl formamide (DMF).

STEP 6

The ester function (—C(O)O—$R_{21}$) of the bicyclic intermediate of formula (g) is then subjected to hydrolysation using an appropriate agent such as HCl in an appropriate solvent such as ethyl ether to yield to the free carboxylic acid. The resulting compound is then coupled to $R_1H$ with a peptide coupling agent such as BOP in an appropriate solvent such as DMF to yield a bicyclic coupled compound of formula (VIII). Suitable conditions for peptide bond formation are well known in th art of peptide chemistry. For example see *Principles of Peptide Synthesis*, Bodanszky M., Springer-Verlag, Berlin, Heidelberg, New York, Tokyo 1984; and *The Peptides, Analysis, Synthesis, Biology, Vol. 1*, edited by Gross E., and Meienhofer J., Academic Press, New York, San Francisco, London, 1979.

For preparation of the compounds of formula (IX) various methods can be employed depending upon the particular starting materials and/or intermediates involved. The following scheme is one particular method of preparation.

SCHEME 3

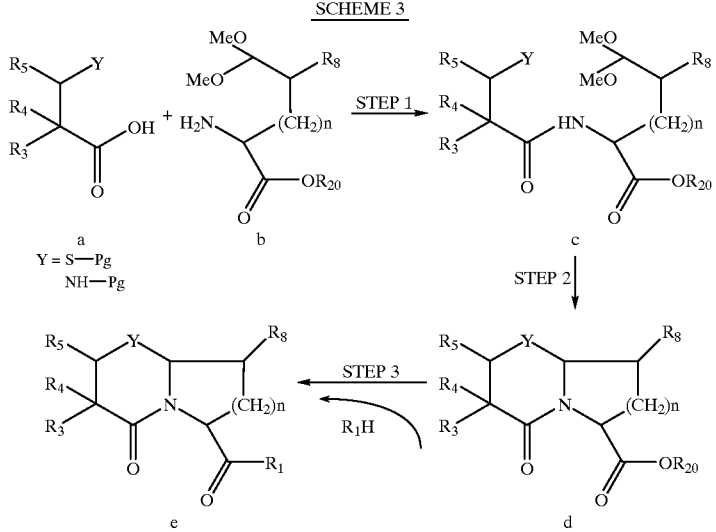

wherein:
Pg is a sulfur or amino protecting group;
L is a leaving group;
each of $R_{20}$; and $R_{21}$ is independently a $C_{1-6}$ alkyl; and $R_1$, $R_3$, $R_4$ and $R_5$ are as previously defined.

The process depicted in scheme 3 is briefly described as follows:

STEP 1:

The carboxylic acid compound (a) is coupled to the cyclic amine compound (b) with a peptide coupling agent such as benzotriazol-1-yloxy-tris-(dimethylamino)phosphonium hexafluorophosphate (BOP reagent) in the presence of a base such as n-methylmorpholine in an appropriate solvent such as dimethylformamide (DMF) or dichloromethane (DCM) to yield to an amido compound of formula (c). Suitable conditions for peptide bond formation are well known in th art of peptide chemistry. For example see *Principles of Peptide Synthesis*, Bodanszky M., Springer-Verlag, Berlin, Heidelberg, New York, Tokyo 1984; and *The Peptides, Analysis, Synthesis, Biology*, Vol. 1, edited by Gross E., and Meienhofer J., Academic Press, New York, San Francisco, London, 1979.

STEP 2

The compound of formula (c) is subjected to appropriate conditions to allow internal cyclisation to yield a bicyclic intermediate of formula (d). For example, acid mediated cyclisation using p-toluenesulfonic acid or TFA in an appropriate solvent such as dichloroethane.

STEP 3

The ester function (—C(O)O—$R_{20}$) of the bicyclic intermediate of formula (d) is subjected to hydrolysis using an appropriate agent such as lithium hydroxide (LiOH) in an appropriate solvent such as tetrahydrofuran (THF) to yield to the free carboxylic acid. The resulting compound is then coupled to $R_1H$ with a peptide coupling agent such as BOP in an appropriate solvent such as DMF to give compound (e). Suitable conditions for peptide bond formation are well known in the art of peptide chemistry. For example see *Principles of Peptide Synthesis,*, Bodanszky M., Springer-Verlag, Berlin, Heidelberg, New York, Tokyo 1984; and *The Peptides, Analysis, Synthesis, Biology*, Vol. 1, edited by Gross E., and Meienhofer J., Academic Press, New York, San Francisco, London, 1979.

For preparation of the compounds of formula (X) various methods can be employed depending upon the particular starting materials and/or intermediates involved. The following scheme 4 is one particular method of preparation.

SCHEME 4

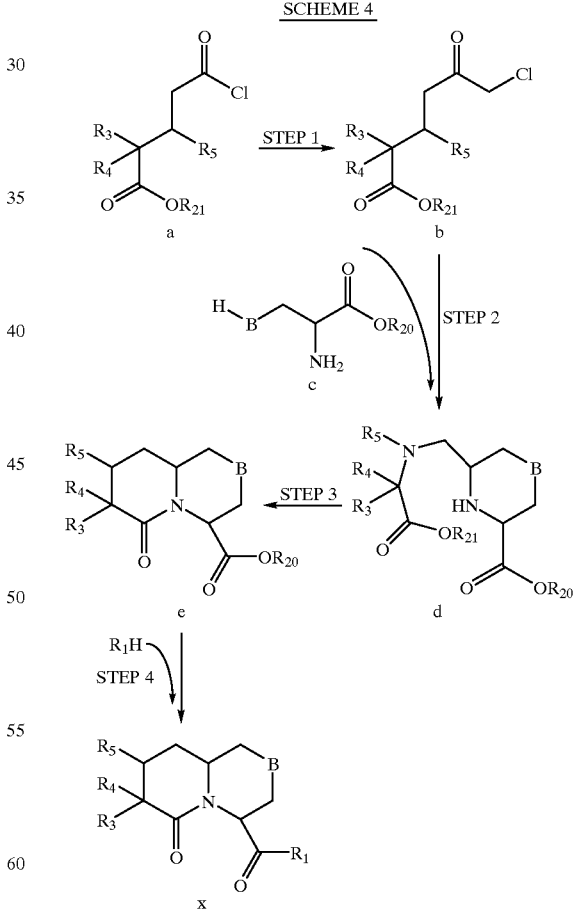

wherein:
each of $R_{20}$ and $R_{21}$ is independently a $C_{1-6}$ alkyl; and B, $R_1$, $R_3$, $R_4$, and $R_5$ are as previously defined.

The process defined in scheme 4 is briefly described as follows:

STEP 1:

The halogenated compound of formula (a) is converted to a halomethyl ketone of formula (b) using an appropriate reagent, such as diazomethane in an inert solvent such as diethyl ether at a temperature of about −25° C. to about 0° C. The resulting mixture is then treated under acidic conditions to yield to the halomethyl ketone of formula (b).

STEP 2

The halomethyl ketone of formula (b) is coupled with an amino acid alkyl ester of formula (c) with an appropriate base such as sodium cyanoborohydride in an organic solvent such as methanol (MeOH) to yield to a cyclic intermediate of formula (d).

STEP 3

The cyclic intermediate of formula (d) is treated under acidic conditions using an appropriate acid such as camphorsulfonic acid in an appropriate solvent such as toluene to yield to a bicyclic intermediate of formula (e).

STEP 4

The ester function (—C(O)O—R$_{20}$) of the bicyclic intermediate of formula (e) is subjected to hydrolysation using an appropriate reagent such as LiOH to yield to the free carboxylic acid. The resulting compound is then coupled to R$_1$H with a peptide coupling agent such as BOP in an appropriate solvent such as dimethylformamide to yield to a coupled bicyclic compound of formula (X). Suitable conditions for peptide bond formation are well known in th art of peptide chemistry. For example see *Principles of Peptide Synthesis,*, Bodanszky M., Springer-Verlag, Berlin, Heidelberg, New York, Tokyo 1984; and *The Peptides, Analysis, Synthesis, Biology, Vol.* 1, edited by Gross E., and Meienhofer J., Academic Press, New York, San Francisco, London, 1979.

Compounds of the present invention are further characterized by their ability to inhibit the catalytic activity of thrombin, which is demonstrated in the assay as follows. Compounds of the present invention may be prepared for assay by dissolving them in buffer to give solutions ranging in concentrations from 1 to 100 μM. In an assay to determine the inhibitory dissociation constant, K$_i$, for a given compound, a chromogenic or fluorogenic substrate of thrombin would be added to a solution containing a test compound and thrombin; the resulting catalytic activity of the enzyme would be spectrophotometrically determined. This type of assay is well known to those skilled in the art.

The compounds of the present invention may be used as anti-coagulants in vitro or ex vivo as in the case of contact activation with foreign thrombogenic surfaces such as is found in tubing used in extracorporeal shunts. The compounds of the invention may also be used to coat the surface of such thrombogenic conduits. To this end, the compounds of the invention are obtained as lyophilized powders, redissolved in isotonic saline and added in an amount sufficient to maintain blood in an anticoagulated state.

The therapeutic agents of the present invention may be administered alone or in combination with pharmaceutically acceptable carriers. The proportion of each carrier is determined by the solubility and chemical nature of the compound, the route of administration, and standard pharmaceutical practice. For example, the compounds may be injected parenterally; this being intramuscularly, intravenously, or subcutaneously. For parenteral administration, the compound may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may also be administered sublingually in the form of troches or lozenges in which each active ingredient is mixed with sugar or corn syrups, flavouring agents and dyes, and then dehydrated sufficiently to make the mixture suitable for pressing into solid form. The compounds may be administered orally in the form of solutions which may contain colouring and/or flavouring agents.

Physicians will determine the dosage of the present therapeutic agents which will be most suitable. Dosages may vary with the mode of administration and the particular compound chosen. In addition, the dosage may vary with the particular patient under treatment.

When the composition is administered orally, a larger quantity of the active agent will typically be required to produce the same effect as caused with a smaller quantity given parenterally.

To further assist in understanding the present invention, the following non-limiting examples of such thrombin inhibitory compounds are provided. The following examples, of course, should not be construed as specifically limiting the present invention, variations presently known or later developed, which would be within the purview of one skilled in the art and considered to fall within the scope of the present invention as described herein. The preferred compounds as of the present invention are synthesized using conventional preparative steps and recovery methods known to those skilled in the art of organic and bio-organic synthesis, while providing a new a unique combination for the overall synthesis of such compound. Preferred synthetic routes for intermediates involved in the synthesis as well as the resulting anti-thrombotic compounds of the present invention follow.

EXAMPLE 1

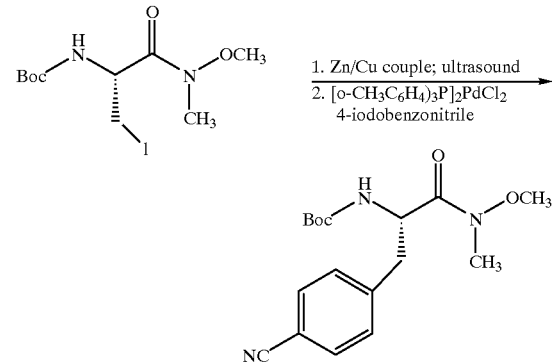

A solution of tert-butyloxycarbonyl-iodo-alanine-N,O-dimethylamide (2.68 g, 7.5 mmol) (*J. Org. Chem.* 1992, 57, 3397–3404) in dry benzene (30 mL), and dry N,N-dimethylacetamide (2.0 mL) was added to a dry nitrogen-purged round bottom flask charged with zinc-copper couple (0.90 g). The resulting mixture was sonicated under nitrogen until no starting material remained (as judged by TLC). Bis(tri-o-tolylphosphine)palladium dichloride (0.35 g, 0.40 mmol) was added followed by 4-iodobenzonitrile (1.72 g, 7.5 mmol). The resulting mixture was stirred under a nitrogen atmosphere with heating, allowed to cool, ethyl acetate (100 mL) was added, and the mixture filtered into a separatory funnel. Sequential washing with aqueous HCl (50 mL; 0.1N), distilled H$_2$O (3×50 mL), drying over Na$_2$SO$_4$, filtration, and concentration under reduced pressure yielded the crude product. Flash chromatography over silica gel (light petroleum-ethyl acetate gradient) afforded the purified compound.

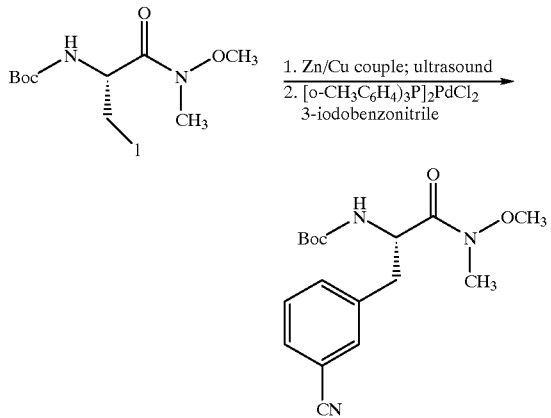

A solution of tert-butyloxycarbonyl-iodo-alanine-N,O-dimethylamide (2.68 g, 7.5 mmol) (*J. Org. Chem.* 1992, 57, 3397–3404) in dry benzene (30 mL), and dry N,N-dimethylacetamide (2.0 mL) was added to a dry nitrogen-purged round bottom flask charged with zinc-copper couple (0.90 g). The resulting mixture was sonicated under nitrogen until no starting material remained (as judged by TLC). Bis(tri-o-tolyphosphine)palladium dichloride (0.35 g, 0.40 mmol) was added followed by 3-iodobenzonitrile (1.72 g, 7.5 mmol). The resulting mixture was stirred under a nitrogen atmosphere with heating, allowed to cool, ethyl acetate (100 mL) was added, and the mixture filtered into a separatory funnel. Sequential washing with aqueous HCl (50 mL; 0.1N), distilled H$_2$O (3×50 mL), drying over Na$_2$SO$_4$, filtration, and concentration under reduced pressure yielded the crude product. Flash chromatography over silica gel (light petroleum-ethyl acetate gradient) afforded the purified compound.

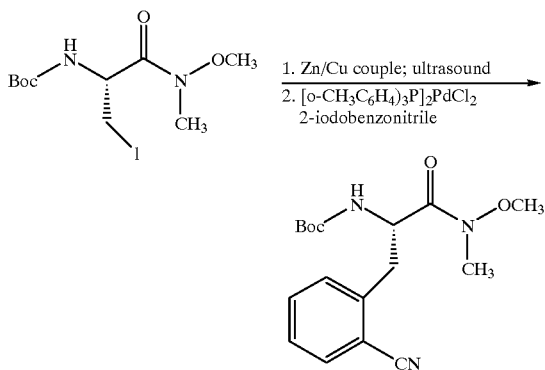

A solution of tert-butyloxycarbonyl-iodo-alanine-N,O-dimethylamide (2.68 g, 7.5 mmol) (*J. Org. Chem.* 1992, 57, 3397–3404) in dry benzene (30 mL), and dry N,N-dimethylacetamide (2.0 mL) was added to a dry nitrogen-purged round bottom flask charged with zinc-copper couple (0.90 g). The resulting mixture was sonicated under nitrogen until no starting material remained (as judged by TLC). Bis(tri-o-tolylphosphine)palladium dichloride (0.35 g, 0.40 mmol) was added followed by 2-iodobenzonitrile (1.72 g, 7.5 mmol). The resulting mixture was stirred under a nitrogen atmosphere with heating, allowed to cool, ethyl acetate (100 mL) was added, and the mixture filtered into a separatory funnel. Sequential washing with aqueous HCl (50 mL; 0.1N), distilled H$_2$O (3×50 mL), drying over Na$_2$SO$_4$, filtration, and concentration under reduced pressure yielded the crude product. Flash chromatography over silica gel (light petroleum-ethyl acetate gradient) afforded the purified compound.

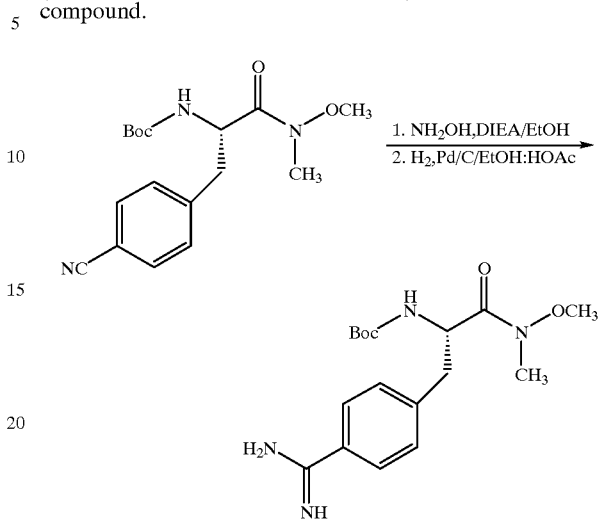

To a solution of tert-butyloxycarbonyl-para-cyano-phenylalanine-N,O-dimethylamide (1.33 g, 4.0 mmol) in dry ethanol (20 mL) was added hydroxlyamine hydrochloride (0.416 g, 6.0 mmol), and diisopropylethylamine (1.02 mL, 6.0 mmol). The mixture was refluxed and then cooled. The precipitate was filtered, washed with cold ethanol, diisopropylether, dried with MgSO$_4$, concentrated under reduced pressure, and used directly in the next step. The semi-solid was suspended in a mixture of acetic acid (20 mL), and dry ethanol (40 mL) with warming. Subsequently, Pd/C catalyst (0.30 g, 10% Pd) was added, and hydrogen was bubbled through the mixture with warming. The hydrogenation was continued until no starting material could be detected as judged by TLC. The catalyst was removed by filtration, the solution was concentrated under reduced pressure (50 mL), HCl (50 mL, 1N) was added, and the mixture was concentrated once again to 50 mL. The solution was chilled overnight yielding the title compound.

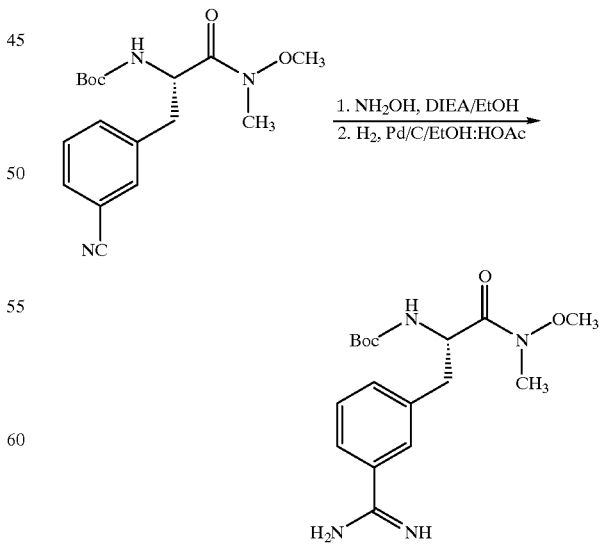

To a solution of tert-butyloxycarbonyl-meta-cyano-phenylalanine-N,O-dimethylamide (1.33 g, 4.0 mmol) in dry ethanol (20 mL) was added hydroxlyamine hydrochloride (0.416 g, 6.0 mmol), and diisopropylethylamine (1.02 mL, 6.0 mmol). The mixture was refluxed and then cooled. The precipitate was filtered, washed with cold ethanol, diisopropylether, dried with MgSO$_4$, concentrated under reduced pressure, and used directly in the next step. The semi-solid was suspended in a mixture of acetic acid (20 mL), and dry ethanol (40 mL) with warming. Subsequently, Pd/C catalyst (0.30 g, 10% Pd) was added, and hydrogen was bubbled through the mixture with warming. The hydrogenation was continued until no starting material could be detected as judged by TLC. The catalyst was removed by filtration, the solution was concentrated under reduced pressure (50 mL), HCl (50 mL, 1N) was added, and the mixture was concentrated once again to 50 mL. The solution was chilled overnight yielding the title compound.

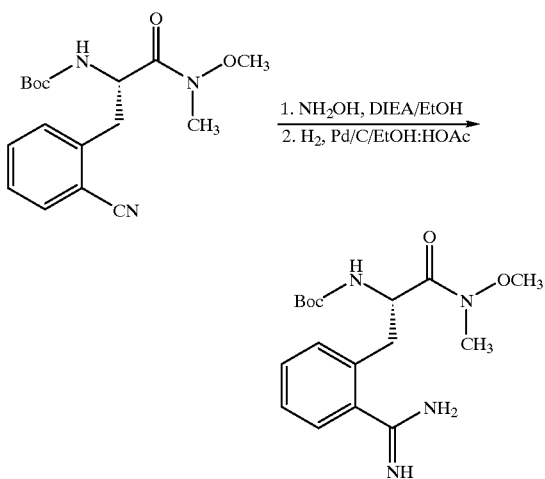

To a solution of tert-butyloxycarbonyl-ortho-cyano-phenylalanine-N,O-dimethylamide (1.33 g, 4.0 mmol) in dry ethanol (20 mL) was added hydroxlyamine hydrochloride (0.416 g, 6.0 mmol), and diisopropylethylamine (1.02 mL, 6.0 mmol). The mixture was refluxed and then cooled. The precipitate was filtered, washed with cold ethanol, diisopropylether, dried with MgSO$_4$, concentrated under reduced pressure, and used directly in the next step. The semi-solid was suspended in a mixture of acetic acid (20 mL), and dry ethanol (40 mL) with warming. Subsequently, Pd/C catalyst (0.30 g, 10% Pd) was added, and hydrogen was bubbled through the mixture with warming. The hydrogenation was continued until no starting material could be detected as judged by TLC. The catalyst was removed by filtration, the solution was concentrated under reduced pressure (50 mL), HCl (50 mL, 1N) was added, and the mixture was concentrated once again to 50 mL. The solution was chilled overnight yielding the title compound.

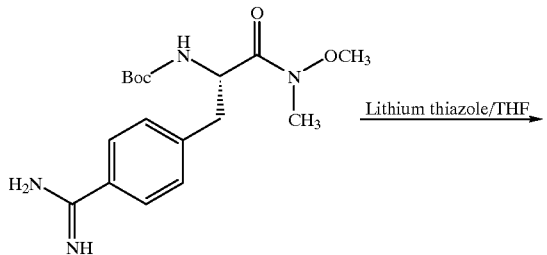

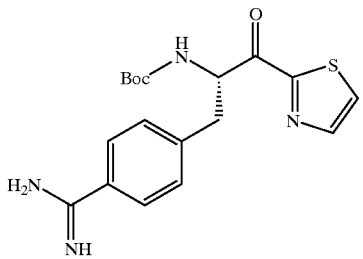

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. tert-Butyloxycarbonyl-para-amidino-phenylalanine-N,O-dimethylamide (1.15 g, 3.3 mmol) in THF (15 mL) was then added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

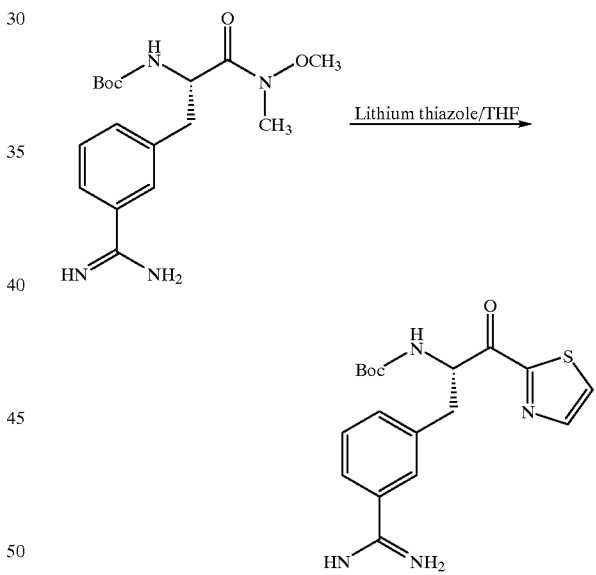

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. tert-Butyloxycarbonyl-meta-amidino-phenylalanine-N,O-dimethylamide (1.15 g, 3.3 mmol) in THF (15 mL) was then added dropwise and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

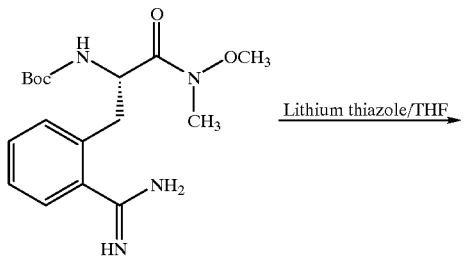

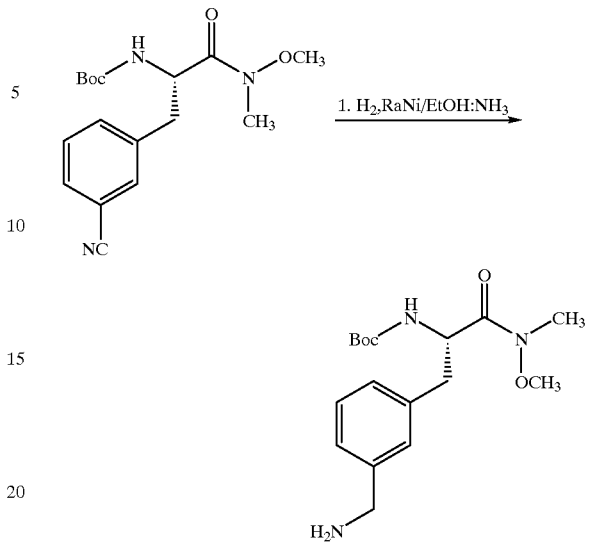

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. tert-Butyloxycarbonyl-ortho-amidino-phenylalanine-N,O-dimethylamide (1.15 g, 3.3 mmol) in THF (15 mL) was then added dropwise, and the resulting mixture stirred. The reaction was quenched with saturated aqueous ammonium chloride. The mixture was diluted with ethyl acetate (150 mL) and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

tert-Butyloxycarbonyl-meta-cyano-phenylalanine-N,O-dimethylamide (1.33 g, 4.0 mmol) was dissolved in ethanol saturated with ammonia (30 mL), and sponge Raney Ni (100 mg) added. The solution was shaken under H$_2$ at room temperature (40 psi). The solution was filtered through celite, and concentrated under reduced pressure to yield a clear residue. The residue was dissolved in ethyl acetate (250 mL), and washed with 1N NaOH (2×50 mL), and brine (2×50 mL). The solution was dried with MgSO$_4$, filtered, and concentrated under reduced pressure.

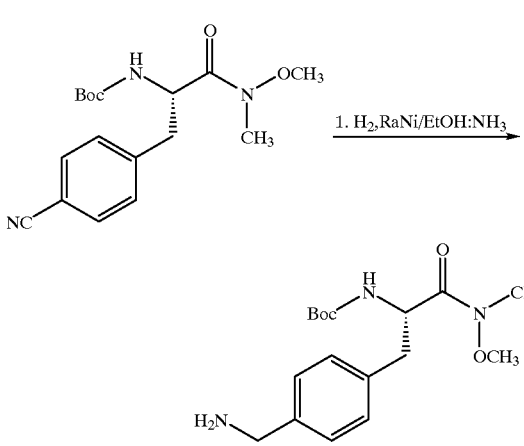

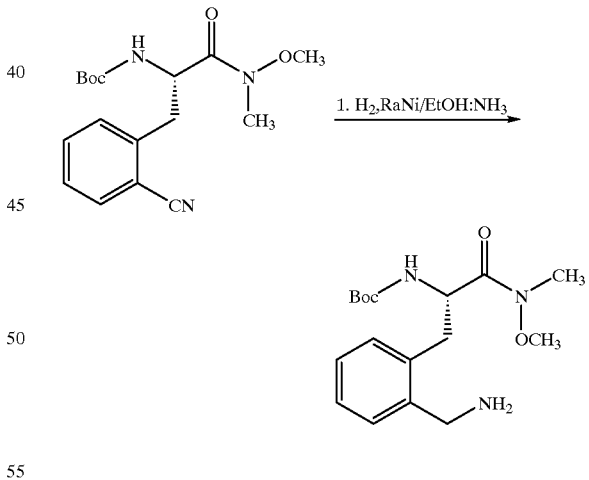

tert-Butyloxycarbonyl-para-cyano-phenylalanine-N,O-dimethylamide (1.33 g, 4.0 mmol) was dissolved in ethanol saturated with ammonia (30 mL), and sponge Raney Ni (100 mg) added. The solution was shaken under H$_2$ at room temperature (40 psi). The solution was filtered through celite, and concentrated under reduced pressure to yield a clear residue. The residue was dissolved in ethyl acetate (250 mL), and washed with 1N NaOH (2×50 mL), and brine (2×50 mL). The solution was dried with MgSO$_4$, filtered, and concentrated under reduced pressure.

tert-Butyloxycarbonyl-ortho-cyano-phenylalanine-N,O-dimethylamide (1.33 g, 4.0 mmol) was dissolved in ethanol saturated with ammonia (30 mL), and sponge Raney Ni (100 mg) added. The solution was shaken under H$_2$ at room temperature (40 psi). The solution was filtered through celite, and concentrated under reduced pressure to yield a clear residue. The residue was dissolved on ethyl acetate (250 mL), and washed with 1N NaOH (2×50 mL), and brine (2×50 mL). The solution was dried with MgSO$_4$, filtered, and concentrated under reduced pressure.

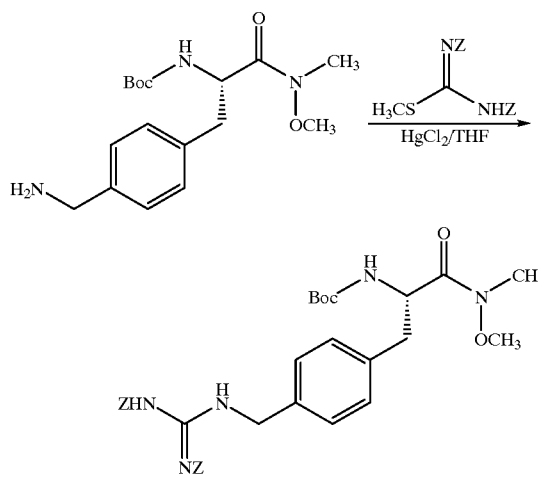

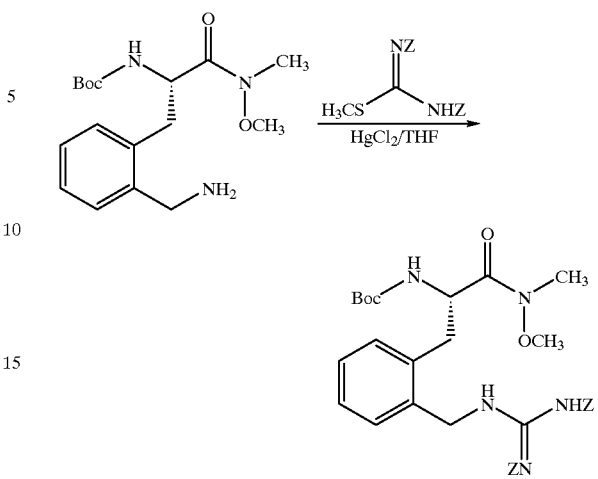

tert-Butyloxycarbonyl-para-aminomethyl-phenylalanine-N,O-dimethylamide (1.00 g, 3.1 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl$_2$ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the purified compound.

tert-Butyloxycarbonyl-ortho-aminomethyl-phenylalanine-N,O-dimethylamide (1.00 g, 3.1 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl$_2$ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the purified compound.

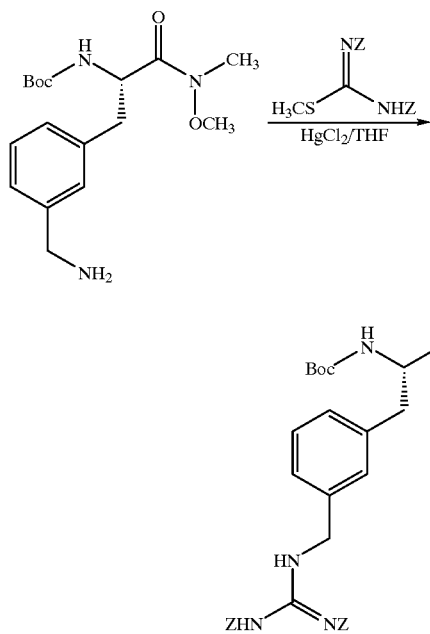

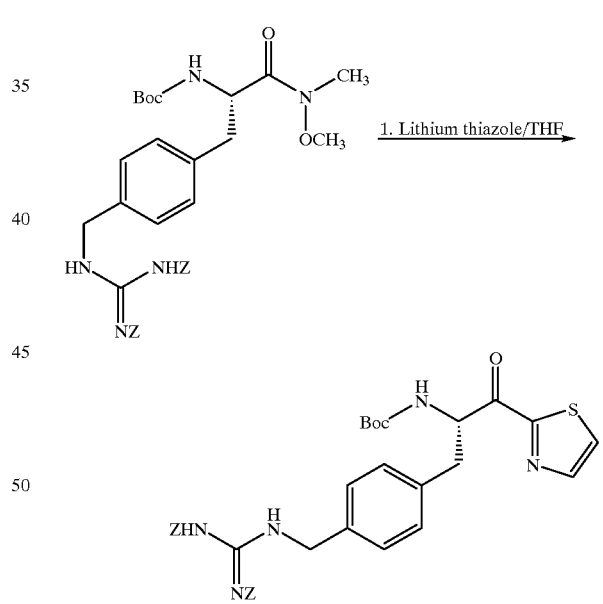

tert-Butyloxycarbonyl-meta-aminomethyl-phenylalanine-N,O-dimethylamide (1.00 g, 3.1 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl$_2$ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the purified compound.

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. The protected amino acid (1.36 g, 3.3 mmol) in THF (15 mL) was then added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

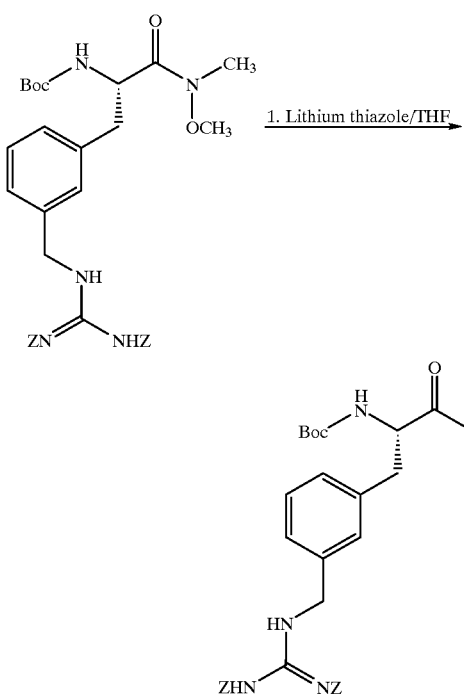

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. The protected amino acid (1.36 g, 3.3 mmol) in THF (15 mL) was then added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with $MgSO_4$, filtered, and concentrated under reduced pressure. The crude material was purified on silica gel (ethyl acetate/hexane), and concentrated under reduced pressure.

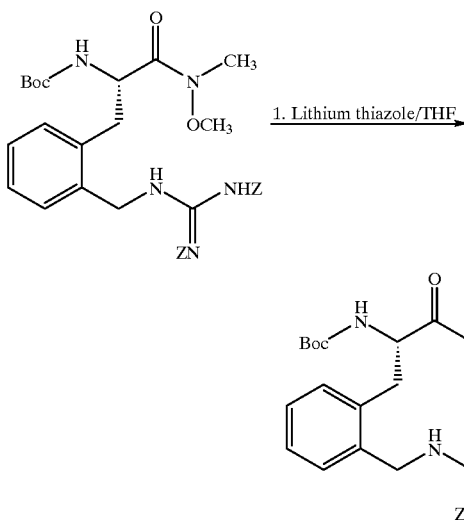

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred. The protected amino acid (1.36 g, 3.3 mmol) in THF (15 mL) was then added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with magnesium sulfate, filtered, and concentrated under reduced pressure. The crude material was purified on silica gel (ethyl acetate/hexane), and concentrated under reduced pressure.

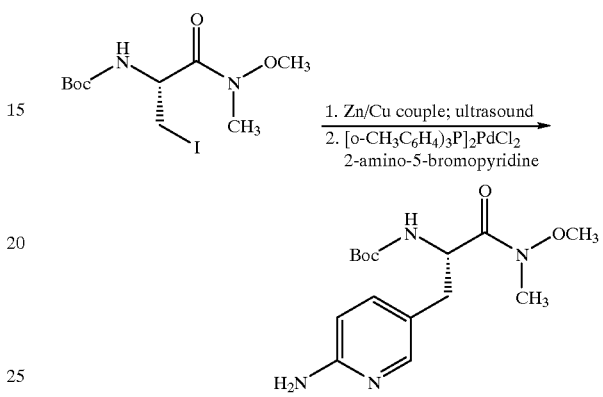

A solution of tert-butyloxycarbonyl-iodo-alanine-N,O-dimethylamide (2.68 g, 7.5 mmol) (*J. Org. Chem.* 1992, 57, 3397–3404) in dry benzene (30 mL), and dry N,N-dimethylacetamide (2.0 mL) was added to a dry nitrogen-purged round bottom flask charged with zinc-copper couple (0.90 g). The resulting mixture was sonicated under nitrogen until no starting material remained (as judged by TLC). Bis(tri-o-tolylphosphine)palladium dichloride (0.35 g, 0.40 mmol) was added followed by 2-iodobenzonitrile (1.72 g, 7.5 mmol). The resulting mixture was stirred under a nitrogen atmosphere with heating, allowed to cool, ethyl acetate (100 mL) was added, and the mixture filtered into a separatory funnel. Sequential washing with aqueous HCl (50 mL; 0.1N), distilled $H_2O$ (3×50 mL), drying over $Na_2SO_4$, filtration, and concentration under reduced pressure yielded the crude product. Flash chromatography over silica gel (light petroleum/ethyl acetate gradient) afforded the purified compound.

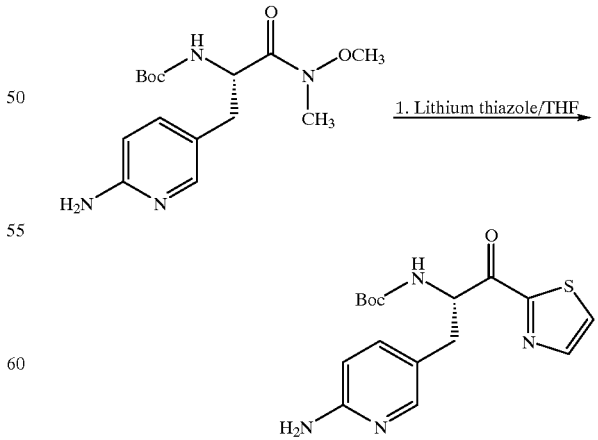

To a solution of thiazole (1.28 g, 15.0 mmol) in anhydrous THF (30 mL) was added n-BuLi (1.6M/hexane, 8.9 mL, 13.9 mmol) dropwise at −78° C., and the solution stirred.

The amino acid-N,O-dimethylamide (1.07 g, 3.3 mmol) in anhydrous THF (15 mL) was then added dropwise and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

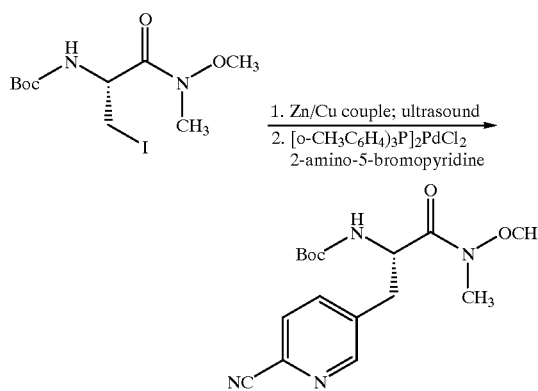

A solution of tert-butyloxycarbonyl-iodo-alanine-N,O-dimethylamide (2.68 g, 7.5 mmol) (*J. Org. Chem.* 1992, 57, 3397–3404) in dry benzene (30 mL), and dry N,N-dimethylacetamide (2.0 mL) was added to a dry nitrogen-purged round bottom flask charged with zinc-copper couple (0.90 g). The resulting mixture was sonicated under nitrogen until no starting material remained (as judged by TLC). Bis(tri-o-tolylphosphine)palladium dichloride (0.35 g, 0.40 mmol) was added followed by 2-iodobenzonitrile (1.72 g, 7.5 mmol). The resulting mixture was stirred under a nitrogen atmosphere with heating, allowed to cool, ethyl acetate (100 mL) was added, and the mixture filtered into a separatory funnel. Sequential washing with aqueous HCl (50 mL; 0.1N), distilled H$_2$O (3×50 mL), drying over Na$_2$SO$_4$, filtration, and concentration under reduced pressure yielded the crude product. Flash chromatography over silica gel (light petroleum/ethyl acetate gradient) afforded the purified compound.

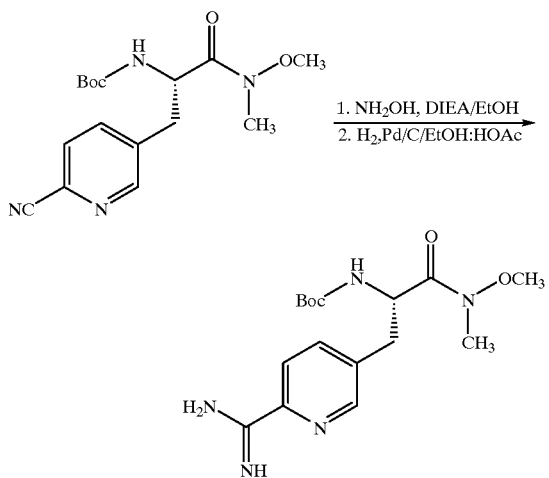

To a solution of tert-butyloxycarbonyl-(4-cyano)3-pyridylalanine-N,O-dimethylamide (1.34 g, 4.0 mmol) in dry ethanol (20 mL) was added N,O-hydroxlyamine hydrochloride (0.416 g, 6.0 mmol), and diisopropylethylamine (1.02 mL, 6.0 mmol). The mixture was refluxed and then cooled. The precipitate was filtered, washed with cold ethanol, diisopropylether, dried with MgSO$_4$, concentrated under reduced pressure, and used directly in the next step. The semi-solid was suspended in a mixture of acetic acid (20 mL), and dry ethanol (40 mL) with warming. Subsequently, Pd/C catalyst (0.30 g, 10% Pd) was added, and hydrogen was bubbled through the mixture with warming. The hydrogenation was continued until no starting material could be detected as judged by TLC. The catalyst was removed by filtration, and the solution was concentrated under reduced pressure (50 mL), HCl (50 mL, 1N) was added, and the mixture was concentrated once again to 50 mL. The solution was chilled overnight yielding the title compound.

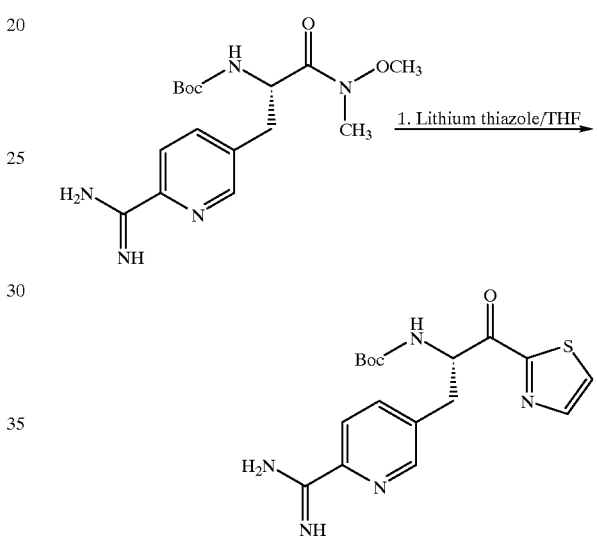

To s solution of thiazole (1.28 g, 15.0 mmol) in anhydrous THF (30 mL) wad added n-BuLi (1.6M/hexane, 8.9 mL, 13.9 mmol) dropwise at −78° C., and the solution stirred. The amino acid-N,O-dimethylamide (1.16 g, 3.3 mmol) in anhydrous THF (15 mL) was then added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel ethyl acetate/hexane), and concentrated under reduced pressure.

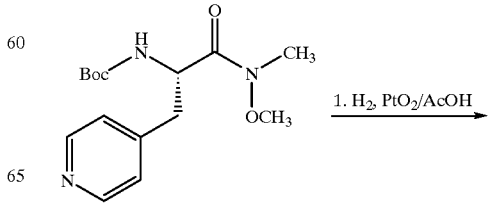

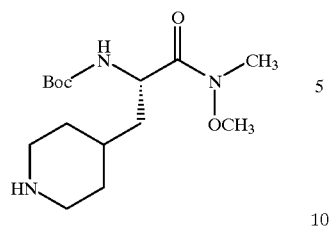

tert-butyloxycarbonyl-3-(4-pyridyl)alanine-N,O-dimethylamide (4.50 g, 14.4 mmol) was dissolved in acetic acid (100 mL), and PtO₂ (100 mg) added. The solution was shaken under H₂ until gas uptake ceased. The solution was filtered through celite, and concentrated under reduced pressure yielding tert-butyloxycarbonyl-3-(4-piperidyl)alanine-N,O-dimethylamide. The residue was dissolved in ethyl acetate (250 mL), washed with 1N NaOH (2×50 mL), dried with MgSO₄, filtered, and concentrated under reduced pressure to yield the title compound.

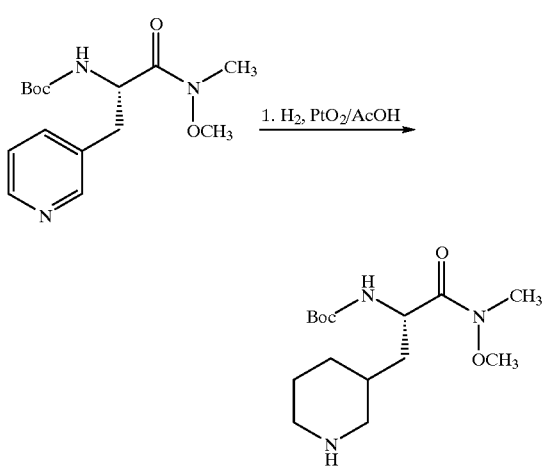

tert-Butyloxycarbonyl-3-(3-pyridyl)alanine-N,O-dimethylamide (4.50 g, 14.4 mmol) was dissolved in acetic acid (100 mL), and PtO₂ (100 mg) added. The solution was shaken under H₂ until gas uptake ceased. The solution was filtered through celite, and concentrated under reduced pressure yielding tert-butyloxycarbonyl-3-(3-piperidyl)alanine-N,O-dimethylamide. The residue was dissolved in ethyl acetate (250 mL), washed with 1N NaOH (2×50 mL), brine (2×50 mL), dried with MgSO₄, filtered, and concentrated under reduced pressure to yield the title compound.

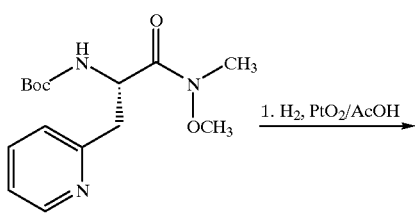

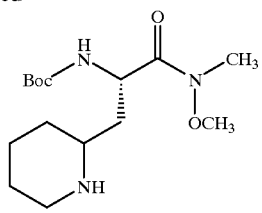

tert-Butyloxycarbonyl-3-(2-pyridyl)alanine-N,O-dimethylamide (4.50 g, 14.4 mmol) was dissolved in acetic acid (100 mL), and PtO₂ (100 mg) added. The solution was shaken under H₂ until gas uptake ceased. The solution was filtered through celite, and concentrated under reduced pressure yielding tert-butyloxycarbonyl-3-2-piperidyl)alanine-N,O-dimethylamide. The residue was dissolved in ethyl acetate (250 mL), washed with 1N NaOH (2×50 mL), brine (2×50 mL), dried with MgSO₄, filtered, and concentrated under reduced pressure to yield the title compound.

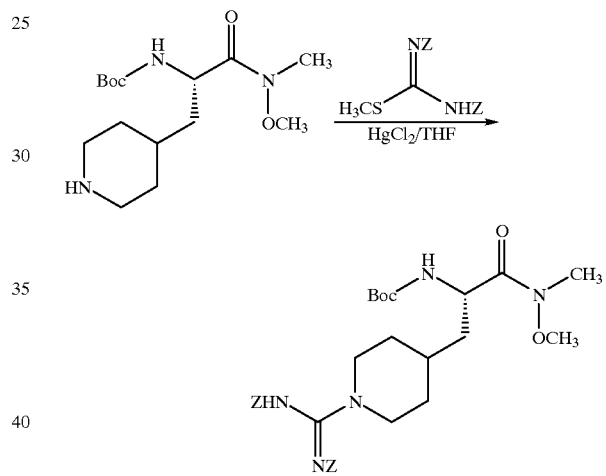

tert-Butyloxycarbonyl-3-(4-piperidyl)alanine-N,O-dimethylamide (1.00 g, 3.2 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl₂ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the title compound.

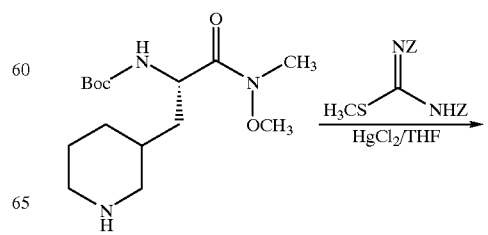

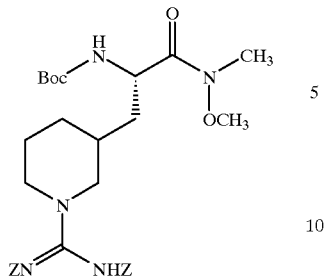

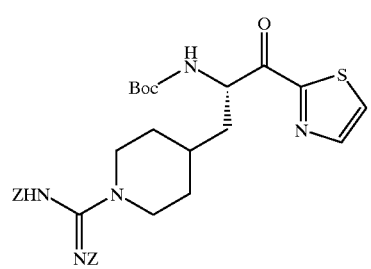

tert-Butyloxycarbonyl-3-(3-piperidyl)alanine-N,O-dimethylamide (1.00 g, 3.2 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl$_2$ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the title compound.

To a solution of thiazole in anhydrous THF (1.23 g, 14.4 mmol) was added n-BuLi (1.6M/hexane, 8.4 mL, 13.4 mmol) dropwise at −78° C. and the solution stirred. The guanidylated 4-piperidylalanine derivative (2.00 g, 3.2 mmol) in anhydrous THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure.

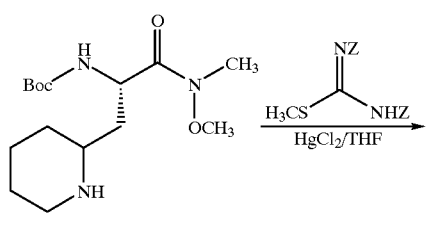

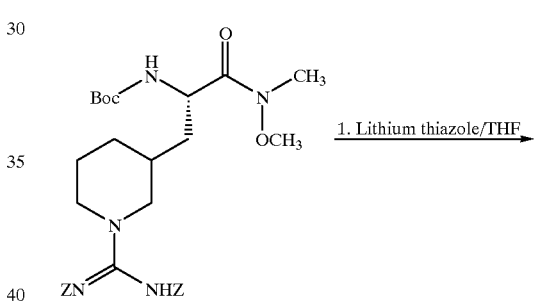

tert-Butyloxycarbonyl-3-(2-piperidyl)alanine-N,O-dimethylamide (1.00 g, 3.2 mmol) was dissolved in dry THF (10 mL) under nitrogen with stirring. The solution was cooled, N,N'-bis-(benzyloxycarbonyl)-S-methyl-isothiourea (1.14 g, 3.2 mmol), and HgCl$_2$ (0.95 g, 3.5 mmol) added. The solution was concentrated under reduced pressure, the remaining residue was suspended in ethyl acetate (200 mL), and filtered through celite. The filtrate was concentrated under reduced pressure. Flash chromatography over silica gel (hexane/ethyl acetate gradient) afforded the title compound.

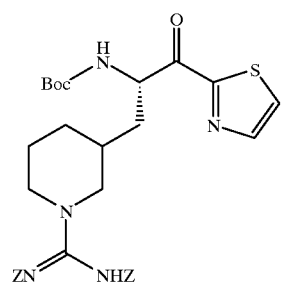

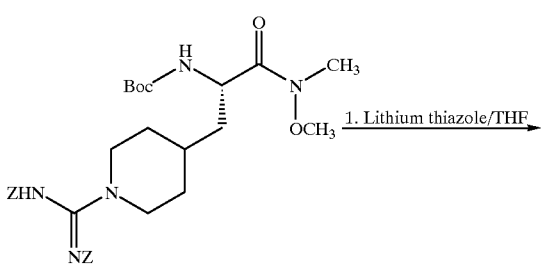

To a solution of thiazole in anhydrous THF (1.23 g, 14.4 mmol) was added n-BuLi (1.6M/hexane, 8.4 mL, 13.4 mmol) dropwise at −78° C. with stirring. The mixture was stirred at −78° C. for 1 h. The guanidylated 3-piperidylalanine derivative (2.00 g, 3.2 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure.

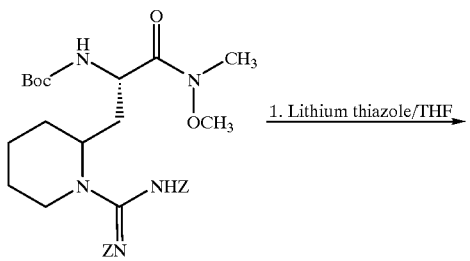

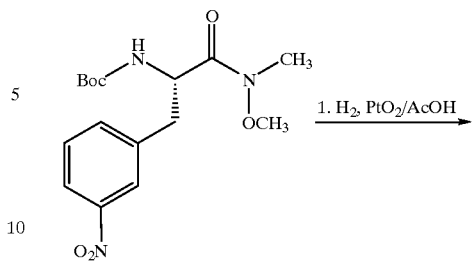

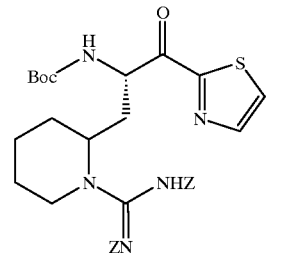

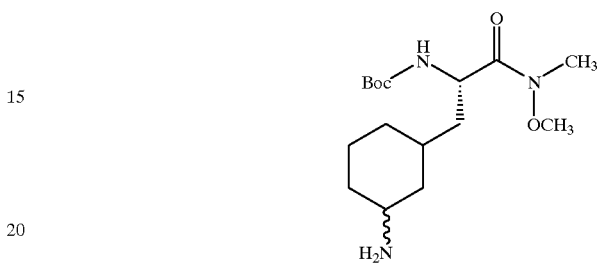

To a solution of thiazole in anhydrous THF (1.23 g, 14.4 mmol) was added n-BuLi (1.6M/hexane, 8.4 mL, 13.4 mmol) dropwise at −78° C. with stirring. The mixture was stirred at −78° C. for 1 h. The guanidylated 2-piperidylalanine derivative (2.00 g, 3.2 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with $MgSO_4$, filtered, and concentrated under reduced pressure.

tert-Butyloxycarbonyl-meta-nitro-phenylalanine-N,O-dimethylamide (13.88 g, 39.3 mmol) was dissolved in acetic acid (100 mL), and $PtO_2$ (100 mg) added. The solution was shaken under $H_2$ until gas uptake ceased. The solution was filtered through celite, concentrated under reduced pressure, taken up in $H_2O$ (150 mL), and lyophilized. The semi-solid was dissolved in ethyl acetate (350 mL), washed with 1N NaOH (3×50 mL), and brine (3×50 mL). The solution was dried with $MgSO_4$, filtered, and concentrated under reduced pressure yielding the title compound.

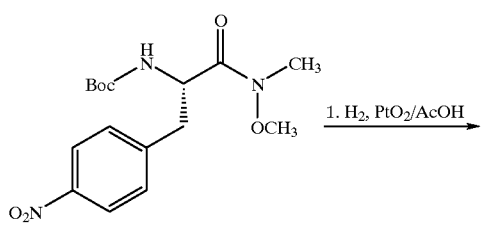

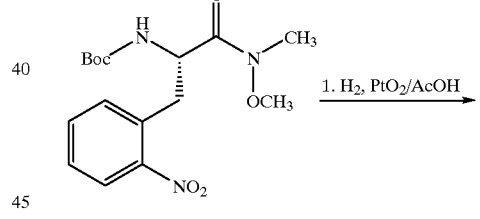

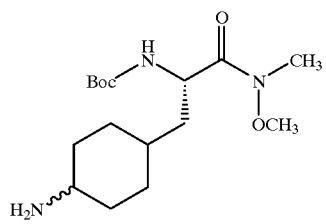

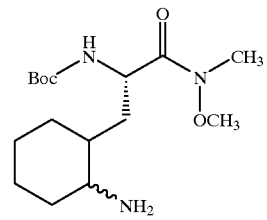

tert-Butyloxycarbonyl-para-nitro-phenylalanine-N,O-dimethylamide (13.88 g, 39.3 mmol) was dissolved in acetic acid (100 mL), and $PtO_2$ (100 mg) added. The solution was shaken under $H_2$ until gas uptake ceased. The solution was filtered through celite, concentrated under reduced pressure, taken up in $H_2O$ (150 mL), and lyophilized. The semi-solid was dissolved in ethyl acetate (350 mL), wash with 1N NaOH (3×50 mL), and brine (3×50 mL). The solution was dried with $MgSO_4$, filtered, and concentrated under reduced pressure yielding the title compound.

tert-Butyloxycarbonyl-ortho-nitro-phenylalanine-N,O-dimethylamide (13.88 g, 39.3 mmol) was dissolved in acetic acid (100 mL), and $PtO_2$ (100 mg) added. The solution was shaken under $H_2$ until gas uptake ceased. The solution was filtered through celite, concentrated under reduced pressure, taken up in $H_2O$ (150 mL), and lyophilized. The semi-solid was dissolved in ethyl acetate (350 mL), washed with 1N NaOH (3×50 mL), and brine (3×50 mL). The solution was dried with $MgSO_4$, filtered, and concentrated under reduced pressure yielding the title compound.

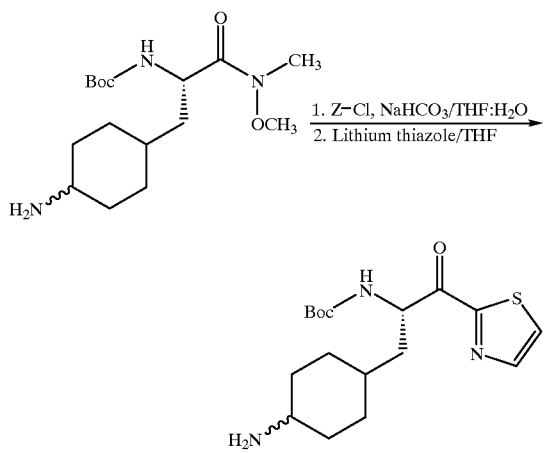

1. tert-Butyloxycarbonyl-3-(cis/trans-4-aminocyclohexyl)alanine-N,O-dimethylamide (1.00 g, 3.0 mmol) was dissolved in saturated aqueous sodium bicarbonate, and THF [60 mL, (1:1)] with stirring. The solution was cooled and a solution of benzyl chloroformate (0.43 mL, 3.0 mmol) in THF (10 mL) was added dropwise. Excess solid sodium bicarbonate was added, the THF was removed under reduced pressure, and the remaining aqueous phase was poured into ethyl acetate (250 mL), and mixed thoroughly. The aqueous phase was discarded and the remaining solution was washed with saturated aqueous sodium bicarbonate (2×50 mL), 4N aqueous sodium bisulfate (2×50 mL), and brine (2×50 mL). The solution was dried with MgSO$_4$, filtered, and concentrated under reduced pressure. The semi-solid was chromatographed on silica gel (ethyl acetate/hexane).

2. To a solution of thiazole (1.16 g, 13.7 mmol) in anhydrous THF was added n-BuLi (1.6M/hexane, 8.0 mL, 12.8 mmol) dropwise at −78° C. and the solution stirred. The above protected amino acid amide (1.41 g, 3.0 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

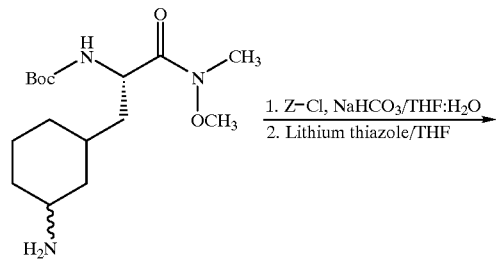

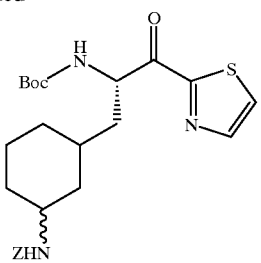

1. tert-Butyloxycarbonyl-3-(cis/trans-3-aminocyclohexyl)alanine-N,O-dimethylamide (1.00 g, 3.0 mmol) was dissolved in saturated aqueous sodium bicarbonate, and THF [60 mL, (1:1)] with stirring. The solution was cooled and a solution of benzyl chloroformate (0.43 mL, 3.0 mmol) in THF (10 mL) was added dropwise. Excess solid sodium bicarbonate was added, the THF was removed under reduced pressure, and the remaining aqueous phase was poured into ethyl acetate (250 mL), and mixed thoroughly. The aqueous phase was discarded and the remaining solution was washed with saturated aqueous sodium bicarbonate (2×50 mL), 4N aqueous sodium bisulfate (2×50 mL), and brine (2×50 mL). The solution was dried with MgSO$_4$, filtered, and concentrated under reduced pressure. The semi-solid was chromatographed on silica gel (ethyl acetate/hexane).

2. To a solution of thiazole (1.16 g, 13.7 mmol) in anhydrous THF was added n-BuLi (1.6M/hexane, 8.0 mL, 12.8 mmol) dropwise at −78° C. and the solution stirred. The above protected amino acid amide (1.41 g, 3.0 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

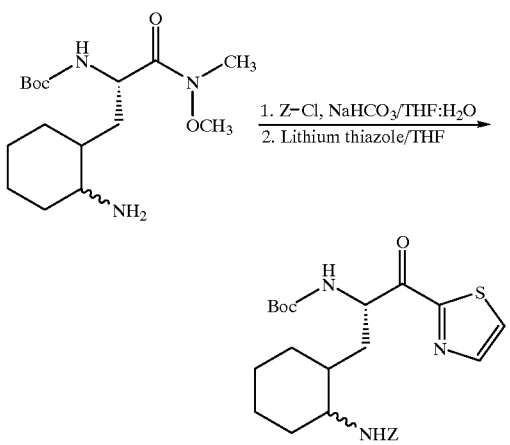

1. tert-Butyloxycarbonyl-3-(cis/trans-2-aminocyclohexyl)alanine-N,O-dimethylamide (1.00 g, 3.0 mmol) was dissolved in saturated aqueous sodium bicarbonate, and THF [60 mL, (1:1)] with stirring. The solution was cooled and a solution of benzyl chloroformate (0.43 mL, 3.0 mmol) in THF (10 mL) was added dropwise.

Excess solid sodium bicarbonate was added, the THF was removed under reduced pressure, and the remaining aqueous phase was poured into ethyl acetate (250 mL), and mixed thoroughly. The aqueous phase was discarded and the remaining solution was washed with saturated aqueous sodium bicarbonate (2×50 mL), 4N aqueous sodium bisulfate (2×50 mL), and brine (2×50 mL). The solution was dried with MgSO$_4$, filtered, and concentrated under reduced pressure. The semi-solid was chromatographed on silica gel (ethyl acetate/hexane).

2. To a solution of thiazole (1.16 g, 13.7 mmol) in anhydrous THF was added n-BuLi (1.6M/hexane, 8.0 mL, 12.8 mmol) dropwise at −78° C. and the solution stirred. The above protected amino acid amide (1.41 g, 3.0 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

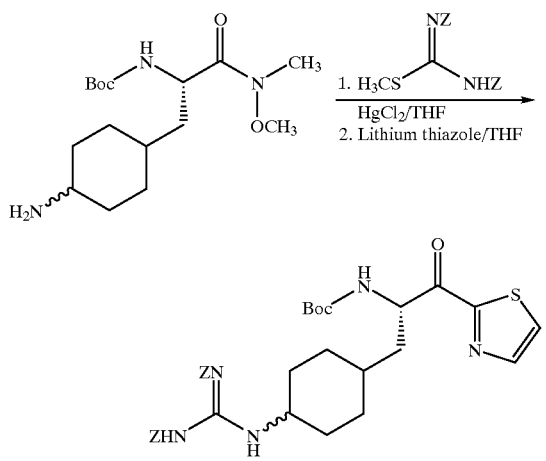

1. tert-Butyloxycarbonyl-3-(cis/trans-4-aminocyclohexyl)alanine-N,O-dimethylamide (2.0 g, 6.1 mmol) was dissolved in dry THF (20 mL) under nitrogen with stirring. The solution was cooled to 0° C., N,N'-bis-(benzyloxycarbonyl)-S-methyl-isothiourea (2.18 g, 6.1 mmol), and HgCl$_2$ (1.81 g, 6.7 mmol) added. The solution was concentrated under reduced pressure, the remaining residue was suspended in ethyl acetate (300 mL), and filtered through celite. The filtrate was concentrated under reduced pressure. Flash chromatography over silica gel (hexane/ethyl acetate gradient) afforded the purified product.

2. To a solution of thiazole (2.32 g, 27.3 mmol) in anhydrous THF was added n-BuLi (1.6M/hexane, 15.9 mL, 25.4 mmol) dropwise at −78° C. and the solution stirred. The above guanidylated amino acid (3.88 g, 6.1 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

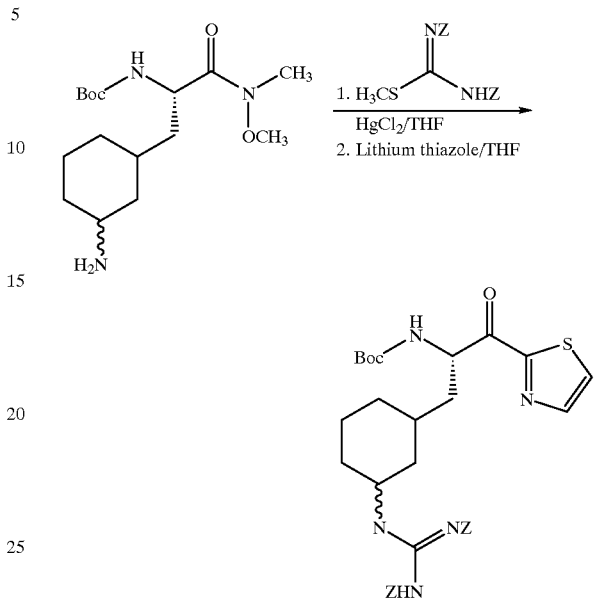

1. tert-Butyloxycarbonyl-3-(cis/trans-3-aminocyclohexyl)alanine-N,O-dimethylamide (2.0 g, 6.1 mmol) was dissolved in dry THF (20 mL) under nitrogen with stirring. The solution was cooled to 0° C., N,N'-bis-(benzyloxycarbonyl)-S-methyl-isothiourea (2.18 g, 6.1 mmol), and HgCl$_2$ (1.81 g, 6.7 mmol) added. The solution was concentrated under reduced pressure, the remaining residue was suspended in ethyl acetate (300 mL), and filtered through celite. The filtrate was concentrated under reduced pressure. Flash chromatography over silica gel (hexane/ethyl acetate gradient) afforded the purified product.

2. To a solution of thiazole (2.32 g, 27.3 mmol) in anhydrous THF was added n-BuLi (1.6M/hexane, 15.9 mL, 25.4 mmol) dropwise at −78° C. and the solution stirred. The above guanidylated amino acid (3.88 g, 6.1 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO$_4$, filtered, and concentrated under reduced pressure. The crude material was purified on silica gel (ethyl acetate/hexane), and concentrated under reduced pressure.

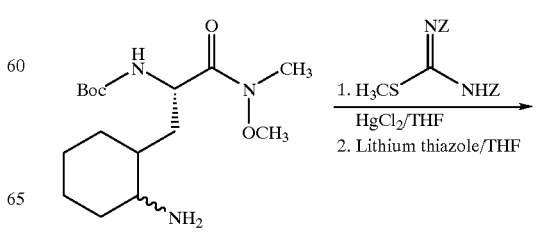

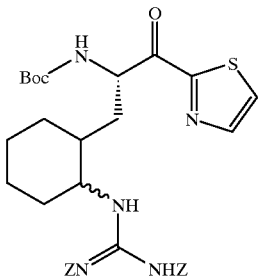

1. tert-Butyloxycarbonyl-3-(cis/trans-2-aminocyclohexyl)alanine-N,O-dimethylamide (2.0 g, 6.1 mmol) was dissolved in dry THF (20 mL) under nitrogen with stirring. The solution was cooled at 0° C., N,N'-bis-(benzyloxycarbonyl)-S-methyl-isothiourea (2.18 g, 6.1 mmol), and HgCl₂ (1.81 g, 6.7 mmol) added. The solution was concentrated under reduced pressure, the remaining residue was suspended in ethyl acetate (300 mL), and filtered through celite. The filtrate was concentrated under reduced pressure. Flash chromatography over silica gel (hexane/ethyl acetate gradient) afforded the purified product.

2. To a solution of thiazole (2.32 g, 27.3 mmol) in anhydrous THF was added n-BuLi (1.6M/hexane, 15.9 mL, 25.4 mmol) dropwise at −78° C. and the solution stirred. The above guanidylated amino acid (3.88 g, 6.1 mmol) in THF (15 mL) was added dropwise, and the resulting mixture stirred. The reaction was quenched with saturated aqueous ammonium chloride. The mixture was diluted with ethyl acetate (150 mL), and the organic layer washed with saturated aqueous ammonium chloride (2×50 mL), brine (50 mL), dried with MgSO₄, filtered, and concentrated under reduced pressure. The crude material was purified on silica gel (ethyl acetate/hexane), and concentrated under reduced pressure.

EXAMPLE 2

Synthesis of Intermediates

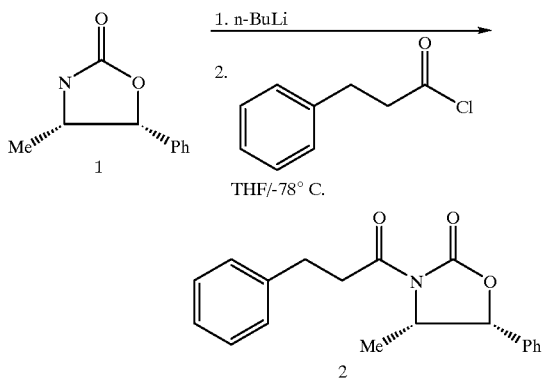

(4S,5R)-3-(1-oxo-3-phenylpropyl)-4-(phenyl)-5-(methyl)-2-oxazolidone (2). A solution of 10.0 g (1.0 equiv., 56.4 mmol) of (4S,5R)-4-phenyl-5-methyl-2-oxazolidone (1) in 250 mL of dry THF, stirred at −78° C. under argon, was treated dropwise with n-butyllithium (1.6 M in hexane, 1.1 eq., 38.8 mL). After stirring for 30 min., 8.4 mL (1.0 equiv., 56.4 mmol) of hydrocinnamoyl chloride was introduced dropwise over a 10 minute period. The resulting mixture was warmed to 0° C., stirred for an additional hour, and quenched with saturated ammonium chloride. The solvent was removed in vacuo and the resulting white solid dissolved in ethyl acetate and ddH₂O. The aqueous phase was removed and extracted with two additional portions of ethyl acetate. The extracts were combined, washed with saturated sodium chloride, dried over sodium sulfate, and the solvent was removed in vacuo to afford a white crystalline solid (2) (in 91% yield).

m.p. 95–96.5; [α]$_D$-35.8 (c=1, CH₂Cl₂); [α]$_D$-26.6 (c=1.018, CH₂Cl₂).

¹HNMR (CDCl₃) δ 0.89 (d, 3H, CH₃, J=6.6 Hz), 3.00–3.05 (m, 2H), 3.26–3.34 (m, 2H), 4.73–4.78 (m, 1H), 5.64 d, 1H, J=7.4 Hz), 7.22–7.46 (m, 10H).

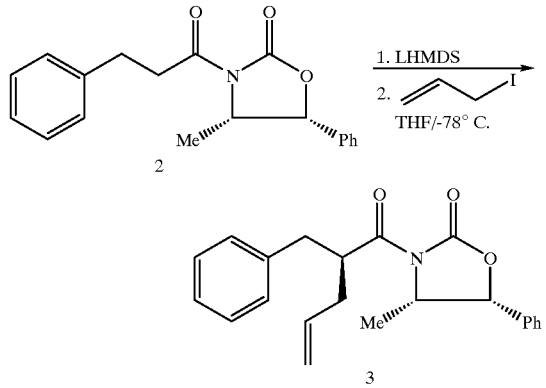

A solution of 5.0 g (1.00 equiv., 16.2 mmol) of (2) in 100 mL of dry THF, was cooled to −78° C. Enolization was achieved with 17.8 mL (1.1 equiv., 17.8 mmol) of lithium bis-trimethylsilylamide, which was added dropwise via syringe. The solution was stirred for 30 min. before 4.45 mL (3.0 equiv., 48.5 mmol) of allyl iodide was introduced and the reaction warmed to −15° C. After 1 h the reaction was quenched with saturated ammonium chloride and extracted (3X) with ethyl acetate. The organic phase was washed with sodium metabisulfite, dried over sodium sulfate and the solvent removed in vacuo to afford an off-colour oil. Purification was achieved by flash chromatography on silica gel using a stepwise gradient (15:1, 12:1, 10:1) to yield (3), a colourless oil (95%).

[α]$_D$ 47.5 (c=3.12, CH₂Cl₂).

¹HNMR (CDCl₃) δ 0.82 (d, 3H, CH₃, J=6.6), 2.31–2.40 (m, 1H, RCH=CHCH₂), 2.49–2.57 (m, 1H, RCH=CHCH₂), 2.84–3.00 (m, 2H, Ph—CH₂), 4.32–4.37 (m, 1H, CH—(N)CO), 4.53–4.58 (m, 1H, CH₃—CH—), 5.03–5.13 (m, 2H, ABX, CH=CH₂), 5.21 (d, 1H, Ph—CH, J=7.1 Hz), 5.81–5.89 (m, 1H, CH=CH₂), 7.20–7.42 (m, 10H, ArH);

¹³C (CDCl₃) δ 14.4, 36.2, 38.2, 43.9, 54.7, 78.4, 117.1, 125.4, 126.3, 128.2, 128.5, 129.0, 133.1, 134.8, 138.9, 152.4, 174.9.

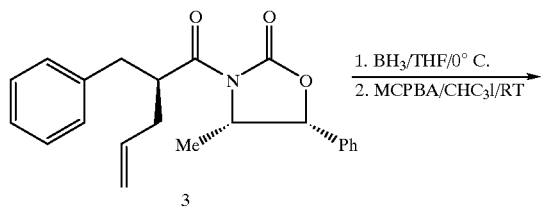

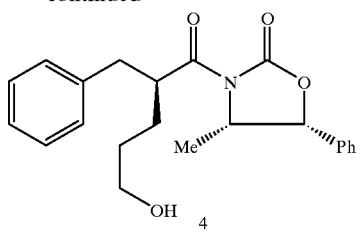

A sample of the allyl compound, (3), (4.75 g, 13.6 mmol) in THF (100 mL) was treated with 13.6 mL (1.0 equiv., 13.6 mmol) of a 1.0 M solution of borane-tetrahydrofuran complex at 0° C. and stirred for 2h. The solvent was evaporated and chloroform (100 mL) added via syringe. Oxidation of the organoborane was achieved by the addition of 4.7 g (2.0 equiv., 27.2 mmol) of 3-chloroperoxybenzoic acid at 0° C., with warming to ambient temperature and stirring for an additional hour. The organic phase was washed with 5% $Na_2CO_3$, dd$H_2O$, and dried over sodium sulfate. Due to the instability of the alcohol, a quick column was performed to remove the extreme polar and nonpolar material which originated from the 3-chloroperoxybenzoic acid. The alcohol (4) was obtained in a yield of 65%.

$[\alpha]_D$ 39.3 (c=1.038, $CH_2Cl_2$).

$^1$HNMR (CDCl$_3$) δ 1.07 (d, 3H, C$\underline{H}_3$—CH, J=6.5 Hz), 1.81–1.93 (m, 3H, CH$_2$—C$\underline{H}$—H), 2.10–2.19 (m, 1H, CH$_2$—C$\underline{H}$—H), 3.10–3.17 (m, 2H, Ph—C$\underline{H}_2$), 3.873.90 (m, 2H, C$\underline{H}_2$OH), 4.43–4.49 (m, 1H, C$\underline{H}$—CO), 4.70–4.75 (m, 1H, CH$_3$—C$\underline{H}$), 5.36 (d, 1H, Ph—C$\underline{H}$, J=7.1 Hz), 7.41–7.63 (m, 10H, Ar$\underline{H}$);

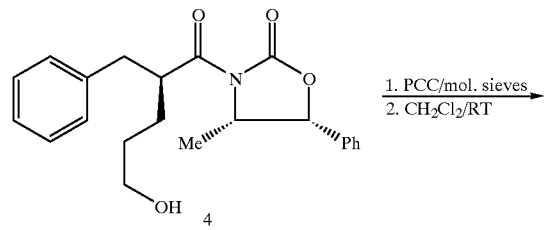

To a solution of the alcohol (4) (1.0 g, 2.7 mmol), dissolved in dichloromethane (27 mL), 876 mg (1.5 equiv., 4.1 mmol) of pyridinium chlorochromate and 1.0 g of 4 angstrom molecular sieves were introduced and the mixture changed from bright orange to a black colour. The reaction was monitored by TLC and after 30 min., if starting material remained, additional molecular sieves were added. The solution was filtered through celite and the solvent was evaporated. The residue was dissolved in ethyl acetate and washed with saturated sodium chloride. If the orange colour persisted in the organic phase, additional filterings through celite pads were performed. The aldehyde was obtained in a quantitative yield as a transparent, colourless oil (5).

$^1$HNMR (CDCl$_3$) δ 0.84 (d, 3H, CH$_3$—CH, J=6.6 Hz), 1.87–1.94 (m, 1H, CH$_2$—C$\underline{H}$(H)—CHO), 2.04–2.13 (m, 1H, CH$_2$—C$\underline{H}$(H)—CHO), 2.45–2.50 (m, 2H, Ph—C$\underline{H}_2$), 2.79–2.85 (dd, 1H, C$\underline{H}_2$—CHO, J=13.3 & J=6.6), 2.92–2.99 (dd, 1H, C$\underline{H}_2$—CHO, J=13.2 & J=8.8), 4.19–4.22 (m, 1H, C$\underline{H}$—CO), 4.46–4.51 (m, 1H, CH$_3$—CH), 5.13–5.25 (m, 1H, Ph—C$\underline{H}$), 7.20–7.39 (m, 10H, Ar$\underline{H}$), 9.69 (s, 1H, C$\underline{H}$O);

$^{13}$C (CDCl$_3$) δ 14.2, 23.8, 39.0, 41.2, 43.8, 54.9, 78.6, 125.3, 126.4, 128.2, 128.4, 128.5, 128.9, 132.8, 138.4, 152.4, 174.9, 201.1.

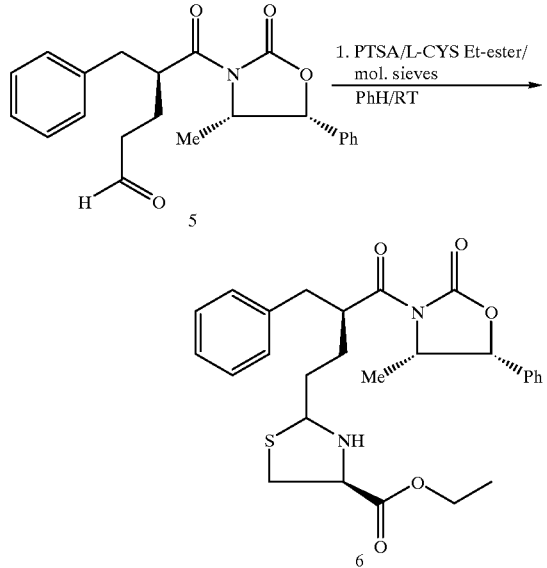

The aldehyde, (5), (2.6 g, 7.10 mmol) was dissolved in benzene (70 mL) and a catalytic amount of p-toluenesulfonic acid was added, followed by 1.58 g (1.2 equiv., 8.52 mmol) of L-cysteine ethyl ester and 4 Å molecular sieves. The reaction was allowed to stir overnight at ambient temperature followed by removal of solvent in vacuo. The residue was dissolved in chloroform, washed with saturated sodium chloride, dd$H_2O$, and dried over sodium sulfate. The solvent was removed in vacuo to afford a gummy solid (6).

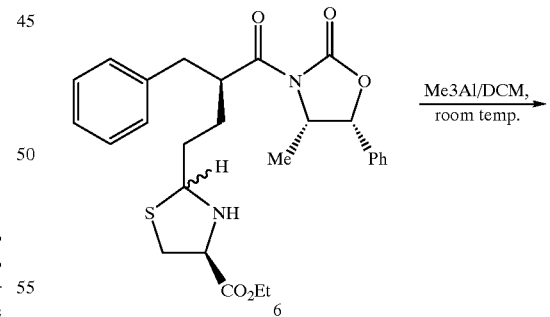

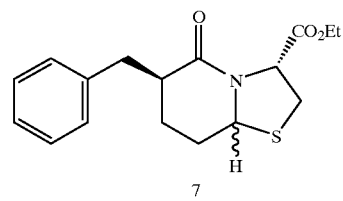

2.0M trimethylaluminum in hexane (2.4 mL, 4.8 mmol, 3 equivalents) was added slowly to starting material (6) (800 mg, 1.61 mmol) stirring in anhydrous dichloromethane under argon, using ovendried equipment. After stirring overnight, HPLC indicated that the reaction had gone to completion.

The mixture was quenched with excess methanol, then filtered on a short silica gel column (washing through with excess 10% methanol in ethylacetate. Evaporation gave 784 mg of crude material that was purified using 2:1 hexane; EtOAc on a silica gel column affording 258 mg (0.81 mmol being a 50% yield) of pure compound (7), a 6S-benzylhexahydro-5-oxo-5H-thiazolo[3,2-a]pyridine-3R-ethyl ester as a white/yellow solid.

$^1$HNMR (CDCl$_3$) δ 1.28–1.31 (m, 3H), 1.72–1.81 (m, 3H), 2.10–2.13 (m, 1H), 2.66 (dd, 1H, J=11.5 and 6.0 Hz), 3.29–3.34 (m, 2H), 4.19–4.29 (m, 2H), 4.88 (dd, 1H, J=9.0 and 5.0 Hz), 5.22 (dd, 1H, J=8.0 and 6.0 Hz), 7.18–7.23 (m, 3H), 7.28–7.31 (m, 2H).

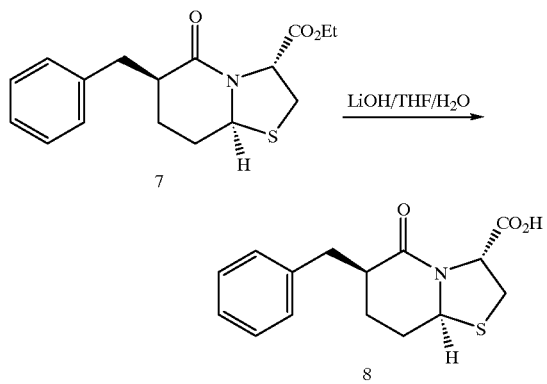

LiOH.H2O (48 mg, 1.12 mmol) in 10 mL of water was added to starting material (7) (240 mg, 0.76 mmol) dissolved in 10 mL of dioxane. After 1 hour, TLC in 1:1 Hexane:EtOAc showed no starting material. The reaction was quenched with 10% citric acid, then extracted twice with dichloromethane. Drying and evaporating the combined organic layers gave 354 mg of crude product. This was redissolved in dichloromethane, then precipitated by adding excess hexane. The product was filtered to give 200 mg (0.68 mmol being a 90% yield)) of an off-white solid, (8), also known as 6S-benzylhexahydro-5-oxo-5H-thiazolo[3,2-a]pyridine-3R-carboxylic acid.

$^1$H NMR (CDCl$_3$) δ 1.71–1.82 (m, 3H), 2.12–2.17 (m, 1H), 2.67 (dd, 1H, J=14 and 11 Hz), 2.77–2.81 (m, 1H), 3.30–3.40 (m, 3H), 4.81 (dd, 1H, J=8.5 and 4.9 Hz), 5.16 (t, 1H, J=7.5 Hz), 7.18–7.31 (m, 5H).

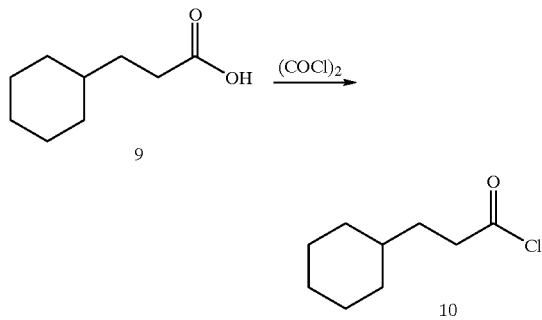

Oxalyl chloride (9) (25 g, 0.197 mol) was cooled to 0° C. and cyclohexane propionic acid (20 ml, 0.14 mol) was added. This was left to stir overnight. The resultant mixture was distilled to give an 84% yield of the colorless liquid (10), cyclohexyl propionic acid chloride.

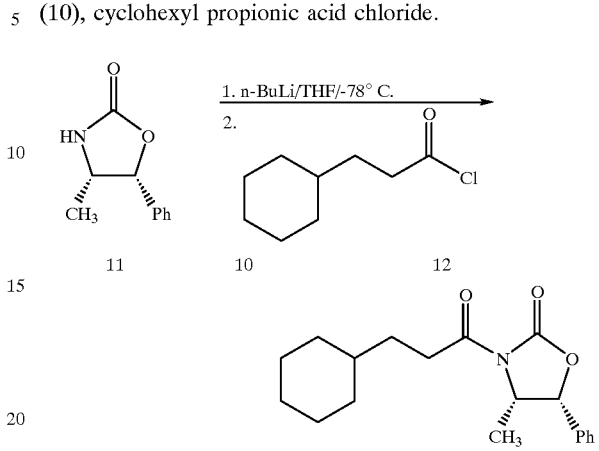

The chiral auxiliary (11) (13.6 g, 76.7 mmol, 1 eq) was dissolved in dry THF and cooled to −78° C. Then n-BuLi (52.8 mL, 84.4 mmol, 1.2 equiv.) was added and left for 30 mins (dark orange solution). The acid chloride (10) (13.4 g, 76.6 mmol, 1 eq) was then added and left to stir overnight. Work-up was done by quenching with saturated NH$_4$Cl extracting with ethylacetate, washing the extracts with water and brine, drying over sodium sulphate and concentration. A fast column, with dry loading, (6:1 hexane ethyl acetate) was run to purify the product. This afforded in a white solid (12) which was recrystallized from ether and hexane to give the title compound in 78% yield.

[α]D=−20.1(c=1, EtOH); MP/BP mp=90.5–91.5° C.

1H NMR (CDCl3)d 0.86–1.10 (m, 5H), 1.18–1.30 (m, 4H), 1.54–1.75 (m, 7H), 2.86–2.97 (m, 2H0, 4.70–4.76 (m, 1H), 5.65 (d, 1H, J→7.2 Hz), 7.28–7.42 (m, 5H).

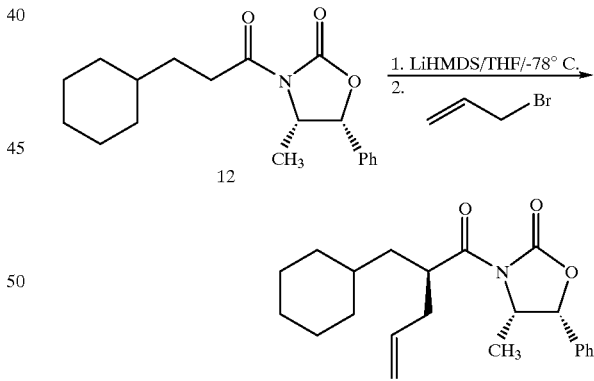

The starting material (12) (9.13 g, 29 mmol, 1 eq) was dissolved in dry THF and cooled to −78° C., after which LiHMDS (31.9 mL, 31.9 mmol, 1.1 eq) was added dropwise over 40 mins. Then, 30 minutes later, allyl bromide (7.5 mL, 86.9 mmol, 3 eq) was added slowly over 10 mins. The mixture was left to warm overnight. Work-up included quenching with sat. ammonium chloride, extraction with ethyl acetate, washing with 10% sodium thiosulphate, decolourising with charcoal, drying over sodium sulphate and concentration in vacuo. The product was obtained as a yellow oil (13) in 96% yield.

[α]D=+9.5 (c=1.0, EtOH)

¹H NMR (CDCl3) d 0.92–1.10 (m, 5H), 1.10–1.39 (m, 5H), 1.63–1.75 (m, 6H), 2.27–2.42 (m, 2H), 4.01–4.14 (m, 1H), 4.76–4.85 (m, 1H), 5.00–5.07 (m, 2H0, 5.65 (d, 1H, J=7 Hz), 5.64–5.88 (m, 1H0, 7.27–7.46 (m, 5H).

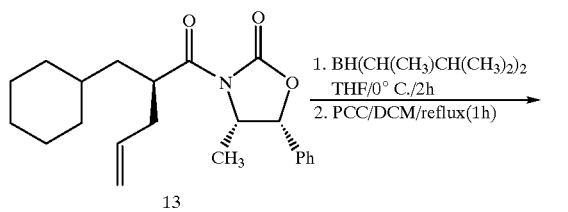

2-methyl-2-butene was added dropwise to borane dimethylsulphide complex at −12° C. The reaction was maintained at this temperature for 15 minutes and then it was warmed to 0° C., after which it was stirred for 2 hours. The disiamyl borane was then added to a mixture of the starting material 13 in THF using a double-ended needle at 0° C. The mixture was then stirred for 2 hours after which the solvents were removed and the residue dissolved in dichloromethane. It was carefully added to a suspension of pyridinium chlorochromate in dichloromethane contained in a flask equipped with a reflux condenser. After the initial exothermic reaction had subsided, the mixture was refluxed at 50° C. for 1 hour. the dark brown liquid was dissolved in ethyl acetate and filtered through Florisil. The black residue of PCC was extracted with ethyl acetate and also filtered through the same Florisil pad. Concentration of the filtrates resulted in a 78% yield of a yellow gummy product (14).

[α]D=−17.8 (c=1.245, EtOH)

¹H NMR (CDCl3) d 0.89–1.18 (m, 5H), 1.20–1.47 (m, 8H), 1.60–1.74 (m, 6H), 1.83–2.00 (m, 1H), 2.48–2.53 (m, 2H), 3.90–4.10 (m, 1H0, 4.12–4.16 (m, 1H), 4.76–4.80 (m, 1H0, 5.67 (d, 1H, J=7 Hz), 7.27–7.46 (m, 5H), 9.77 (s, 1H).

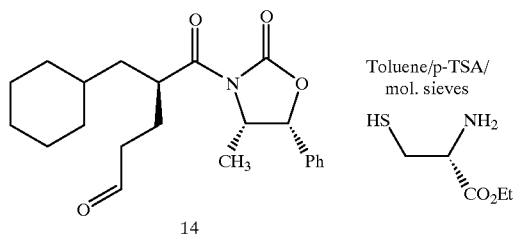

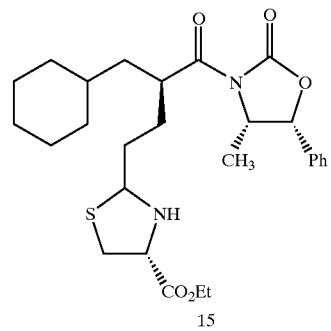

The resulting aldehyde (14) (7.7 g crude, 20.8 mmol 1 equiv.) was dissolved in 75 mL of toluene. To the solution was added a catalytic amount of p-toluenesulphonic acid (50 mg), 10 g of 4 Å molecular sieves, and L-cysteine ethyl ester (3.87 g, 20.8 mmol, 1 equiv.). The mixture was stirred overnight, filtered and concentrated. The residue was then purified by silica gel chromatography (6:1 hexane:ethyl acetate) afforded 6.36 g of the product (15) in 61% yield.

[α]D=−48.3 (c=1.095, EtOH)

¹H NMR (CDCl3) d 0.84–0.98 (m, 4H), 1.11–1.38 (m, 7H), 1.50–1.90 (m, 10H), 2.80–2.99 (m, 1H), 3.24–3.34 (m, 1H), 3.77–4.29 (m, 4H), 4.46–4.81 (m, 2H), 5.66 (d, 1H, J=7 Hz), 7.27–7.46 (m, 5H).

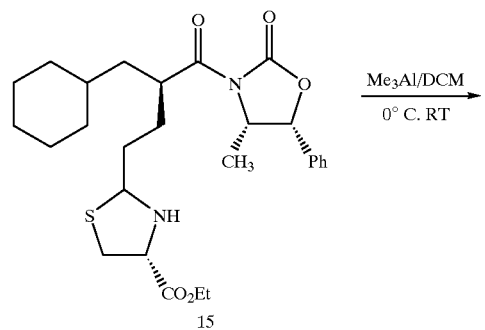

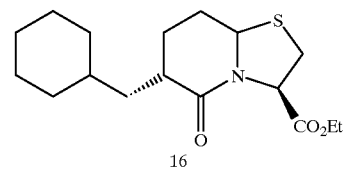

The starting material (15) (1.97 g, 3.9 mmol, 1 equiv.) was dissolved in 20 mL of dry dichloromethane and cooled to 0° C. Trimethylaluminum (5.9 mL, 11.8 mmol, 3 equiv.) was added dropwise and the mixture was left stirring overnight. After complete reaction as evidenced by HPLC, methanol was added until a yellow solid mass was formed. Dichloromethane was added to dissolve the solid and the whole mixture was stirred for 15–30 minutes and then filtered. The residue after concentration in vacuo was run through a quick column (6:1 hexane:ethyl acetate), to remove auxiliary and as many of the polar decomposition products as possible, affording in a 50% yield of a yellow oil (16).

$^1$H NMR (CDCl3) d 0.83–0.98 (m, 2H), 1.09–1.38 (m, 10H), 1.57–2.00 (m, 11H), 2.12–2.18 (m, 1H), 2.49–2.54 (m, 1H), 3.10 (dd, 1H, J=11 and 6 Hz), 3.27 (dd, 1H, J=11.5 and 8.0 Hz), 4.11–4.25 (m, 2H), 4.88 (dd, 1H, J=11.0 and 5.0 Hz), 5.14 (dd, 1H, J=10 and 6 Hz).

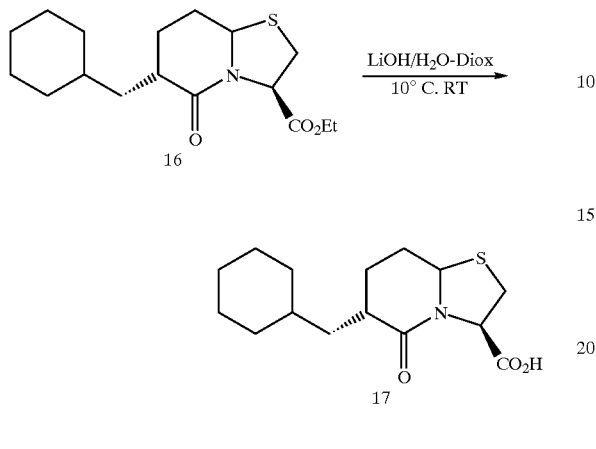

The starting material (16) (0.95 g, 2.9 mmol, 1 equiv.) was dissolved in 10 mL of dioxane. The solution was cooled to 10 C, and to it was added LiOH.H$_2$O (0.123 g, 2.9 mmol, 1 eq.) dissolved in 10 mL of water. The bath was removed and the mixture was stirred at room temperature for 1 hour. TLC showed complete reaction and the solvent was evaporated under vacuum. The remaining aqueous layer was washed with ether (2X), acidified with 10% citric acid, and extracted with dichloromethane (3X). The combined extracts were dried over sodium sulphate and concentrated to give a white solid which was recrystallized from ether. Concentration of the filtrate and purification by silica gel column chromatography (2:1 hexane:ethyl acetate) resulted in more product (17) with a m.p. of 198.2–199° C.

$^1$H NMR (DMSO-d6) d 0.78–0.93 (m, 2H), 1.11–1.27 (m, 5H), 1.34–1.36 (m, 1H), 1.51–1.56 (m, 1H), 1.60–1.75 (m, 1H), 1.82–1.87 (m, 1H), 2.15–2.18 (m, 1H), 2.37–2.41 (m, 1H), 3.03 (dd, 1H, J=11.5 and 5.5 Hz), 3.35–3.38 (m, 2H), 4.83 (dd, 1H, J=9 and 4 Hz), 4.95 (dd, 1H, J=8 and 5.5 Hz).

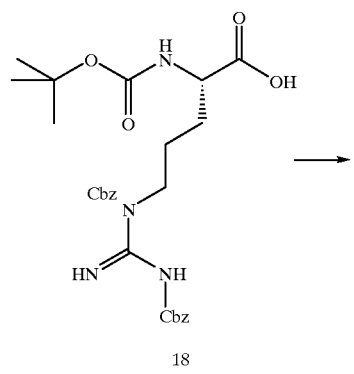

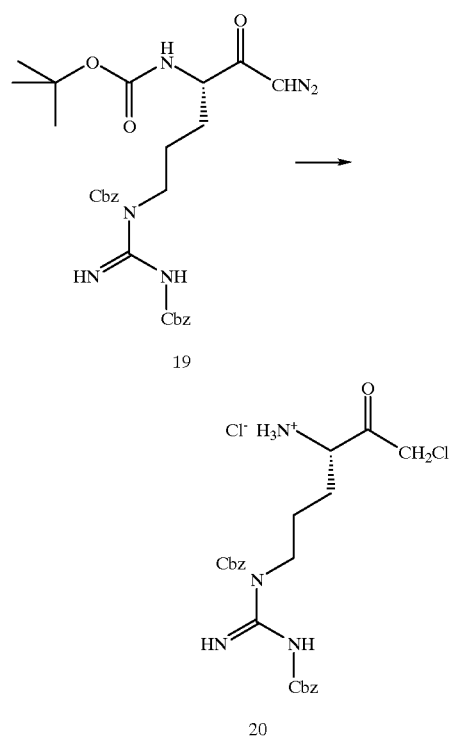

BOC-DiCbz Arg (18) (7.6 g, 14.0 mmol) was dissolved in anhydrous THF (40 mL) and cooled to 0° C. Triethylamine (2.2 mL) was added followed by 14.5 mmol of a 1M toluene solution of isopropyl chloroformate via a syringe. The reaction was allowed to stir at 0° C. for 30 minutes then quickly filtered. The white solid was discarded. To the filtrate was bubbled freshly prepared diazomethane until the color of the solution turned yellow. The reaction mixture was allowed to stand overnight in a well ventilated fumehood which facilitated the discharge of excess diazomethane.

Dry ether was added to precipitate the diazoketone. The product was filtered and dried under vacuum to give light yellow fluffy solid (4.6 g, 58%).

Diazoketone (19) (1 g, 1.77 mmol) was dissolved in THF (20 mL) and to this solution was added 1M HCl in ether (20 mL) at 0° C. The reaction was allowed to stir at ambient temperature overnight during which time a white precipitate was formed. Further precipitation was achieved by adding ether. Filtration and drying the solid afforded the product (20) (1.02 g, 100%).

$^1$H NMR (DMSO-d6) d 1.65–1.77 (m, 3H), 2.06–2.50 (m, 1H), 3.86–3.90 (m, 2H), 4.29 (m, 1H), 4.76 (m, 1H, J=18 Hz), 4.95 (d, 1H, J=18 Hz), 7.35 (s, 2H), 7.36 (s, 2H, 7.35–7.41 (m, 10H), 8.71 (br s, 3H), 10.1 (br s, 2H).

$^{13}$C NMR (DMSO-d6) d 23.7, 26.4, 47.2, 47.9, 56.2, 68.0, 69.3, 128.6, 128.7, 128.8, 128.9, 135.2, 135.9, 153.4, 157.4, 198.9.

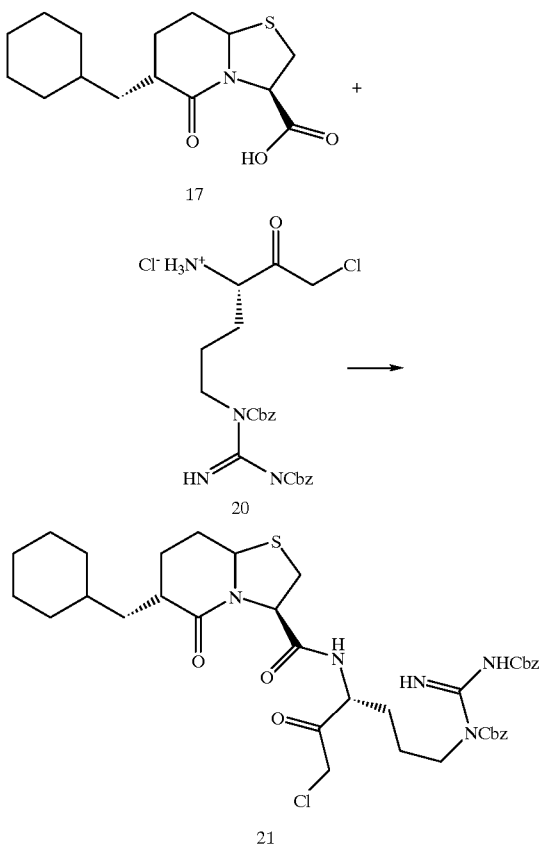

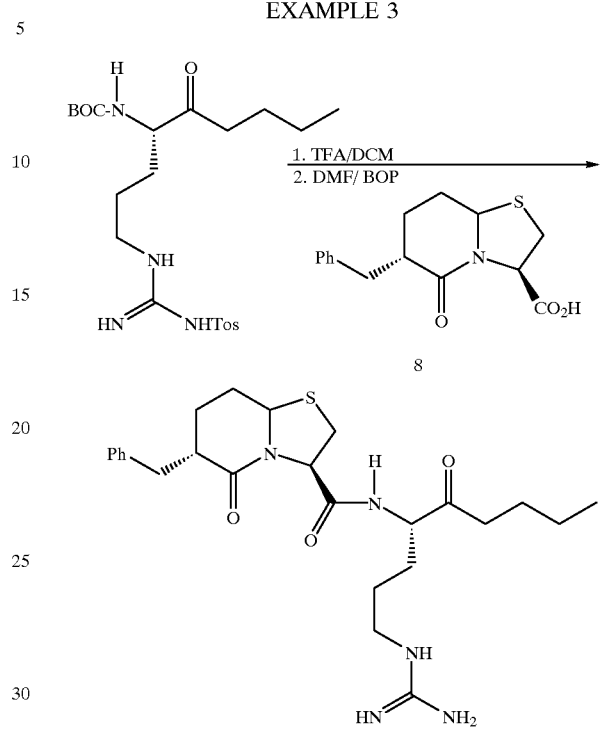

2H), 5.09–5.24 (m, 4H), 7.30–7.39 (m, 10H), 7.95 (d, 1H, J=8 Hz), 9.4 (br s, 1H), 9.56 (br s, 1H).

EXAMPLE 3

To mimetic (17) (0.422 g, 1.42 mmol) in THF (50 mL) at 0° C. and in presence of N-methyl morpholine (0.19 mL), was slowly added 1M toluene solution of isopropylchloroformate (1.71 mL). The reaction was allowed to stir at 0° C. for 30 minutes then treated with aminochloromethylketone (20) in small portions. Once the addition was complete the reaction was further stirred for 15 minutes followed by addition of N-methyl morpholine (0.19 mL). The reaction was stirred at ambient temperature for 3 hours, then extracted with ethyl acetate followed by washing with brine and 10% aqueous citric acid. Removal of organic solvent gave a white foam (21) (1.03 g, 96%) which was used further without purification.

$^1$H NMR (CDCl3) d 0.07–0.97 (m, 1H), 1.15–1.41 (m, 7H), 1.62–1.91 (m, 10H), 2.10–2.16 (m, 1H), 2.43–2.48 (m, 1H), 2.74–2.80 (m, 1H), 3.01–3.07 (m, 1H), 3.87–3.94 (m, 1H), 4.11–4.19 (m, 2H), 4.60–4.66 (m, 1H), 4.74–4.86 (m, (N-t-BOC-N-tosyl)butyrylketoarginine (240 mg, 0.515 mmol), was deprotected using 30% TFA in dichloromethane. The deprotected arginine derivative, was coupled with the mimetic (8) (100 mg, 0.343 mmol) in DMF under basic conditions (Et$_3$N, pH=8–9), using BOP reagent (228 mg, 0.52 mmol) as the dehydrating agent. The reaction was typically complete within 2–4 hours. Extraction with ethyl acetate followed by successive washing with brine and 10% aqueous citric acid yielded the crude product. The crude product was purified by column chromatography affording 180 mg (76%) of pure product. This product was then treated with HF to remove the tosyl group. Purification of the isolated deprotected product by HPLC afforded BCH-2737.

EXAMPLE 4

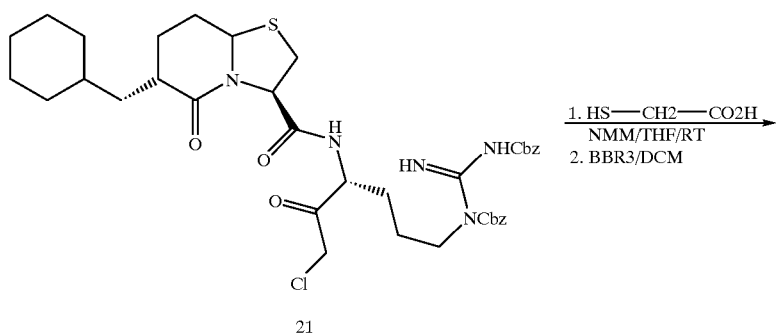

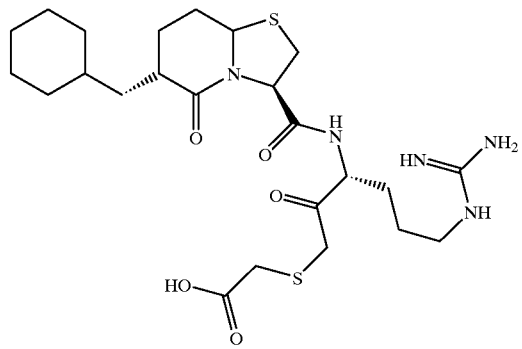

-continued

Chloromethylketone (21) (0.188 g, 0.245 mmol) was dissolved in THF (10 mL) treated with NMM (0.036 mL) followed by mercapto acetic acid (0.02 mL, 0.299 mmol). The reaction was stirred at ambient temperature overnight. Extraction of the reaction mixture with ethyl acetate followed by successive washing with brine and 10% aqueous citric acid and evaporation of organic solvent gave the crude product which was purified by column chromatography to give foamy solid as the product (0.125 g, 62%).

This protected precursor (0.125 g, 0.154 mmol) was dissolved in DCM (5 mL) and cooled to −78° C. A 1M DCM solution of $BBR_3$ (1.54 mL, 1.54 mmol) was slowly added. The reaction was stirred at ambient temperature for 5 hours, then cooled to −78° C. again and treated with anhydrous methanol (2 mL). the reaction was brought to room temperature and stirred for 2 addition hours. The solvents were removed under reduced pressure and the residue was partitioned between ether and water. The water layer was collected, lyophilized and the final product (23) obtained as a powder after HPLC purification and lyophilization.

The products of the reactions described above can be isolated in the free form or in the form of salts. In addition, the products can be obtained as pharmaceutically acceptable acid addition salts by reacting one of the free bases with an acid. In a similar manner, the product can be obtained as pharmaceutically acceptable salts by reacting one of the free carboxylic acids with a base. Likewise, treatment of the salts with a base or acid results in a regeneration of the free amide.

EXAMPLE 5

A general method of synthesizing compound of formula II or III:

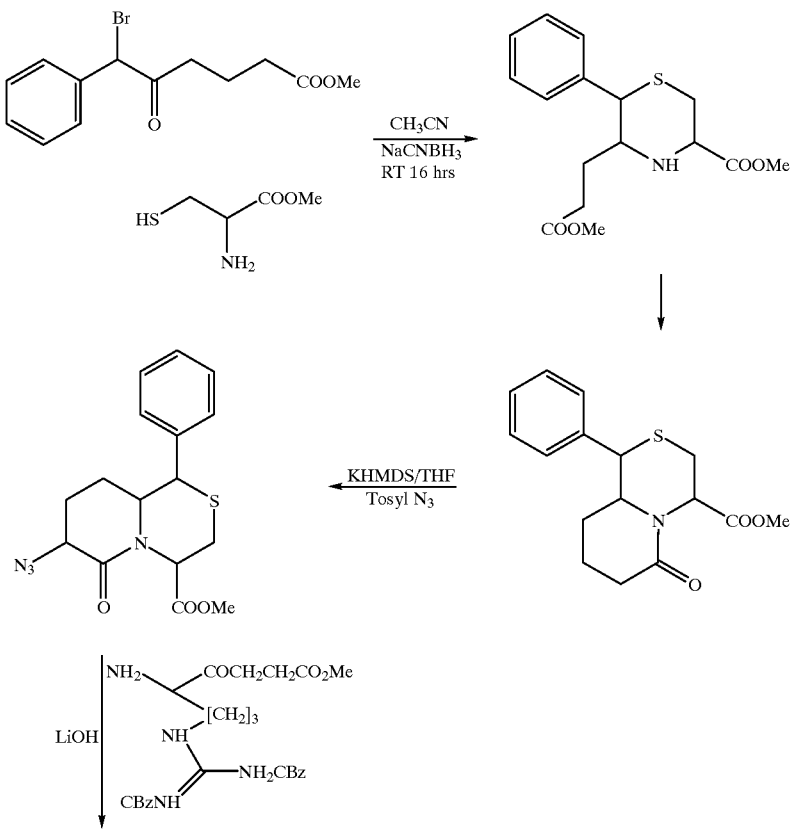

-continued

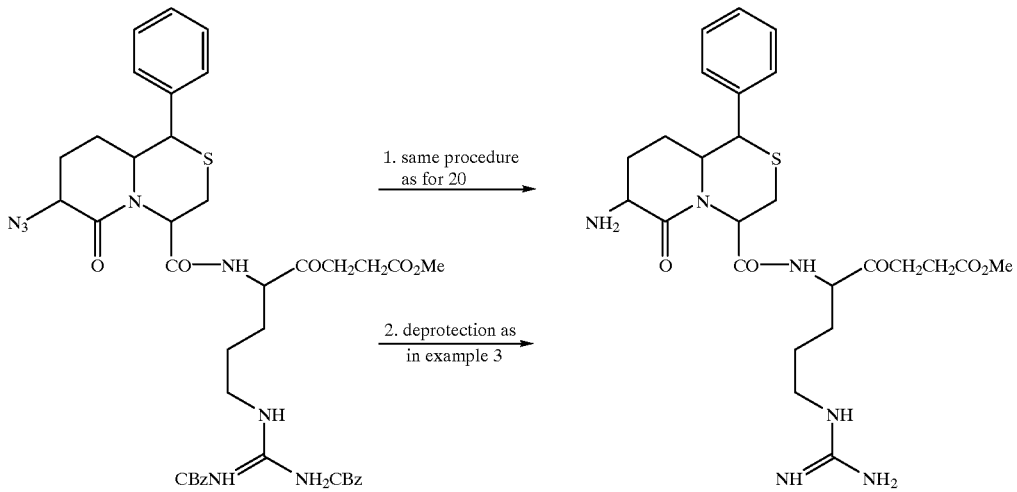

EXAMPLE 6

Synthesis of:

(16)

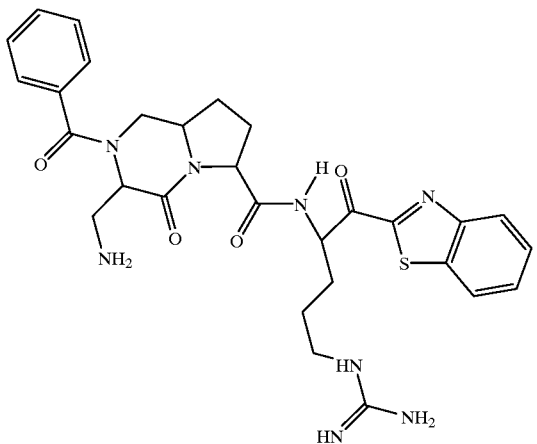

Step 1

Synthesis of 2-Benzyloxycarbonylamino-4-hydroxybutyric acid tert-butyl ester

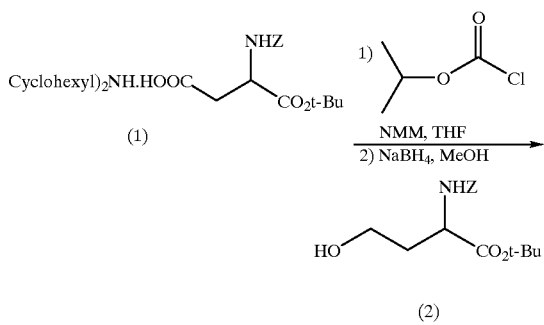

To a solution of the protected aspartic acid (1) (Bachem, 2.50 g, 4.95 mmols) in 50 mL of dry tetrahydrofuran (THF), at −10° C., under $N_2$, was added N-methylmorpholine (109 µL, 0.2 eq) and isopropyl chloroformate (1.0 M/toluene: 384 µL, 1.1 eq). The solution was stirred at −10° C. for 60 min. In another flask, $NaBH_4$ (375 mg, 2 eq) was suspended in a dry 5:1 mixture of THF/MeOH (50 mL), at −78° C., under $N_2$. This suspension was stirred at −78° C. for 30 min. The mixed anhydride solution was then added to the $NaBH_4$ suspension dropwise via canula, and the final solution was stirred at −78° C. for 3 hr. Acetic acid (2.8 mL, 10 eq) was then added and the solution was warmed to r.t. (30 min). The solvents were evaporated, the residue taken up in EtOAc and washed with sat.aq. $NaHCO_3$ (2×) and brine. The organic layer was dried over $MgSO_4$, the solids were filtered and the solvent evaporated to give 1.53 g (4.95 mmols, 100%) of the alcohol (2) as a clear oil.

$^1$H NMR (CDCl$_3$, 400 MHz): δ 7.40–7.31 (m, 5H, ArH), 5.63 (d, 1H, J=7.3, NH), 5.13 (AB system, 2H, J=12.2, CH$_2$Ph), 4.43 (m, 1H, H-2), 3.69 (m, 2H, H-4), 2.17 (m, 1H, H-3), 1.63 (m, 1H, H-3), 1.48 (s, 9H, t-Bu).

Step 2

2-Benzyloxycarbonylamino-4-iodobutyric acid tert-butyl ester

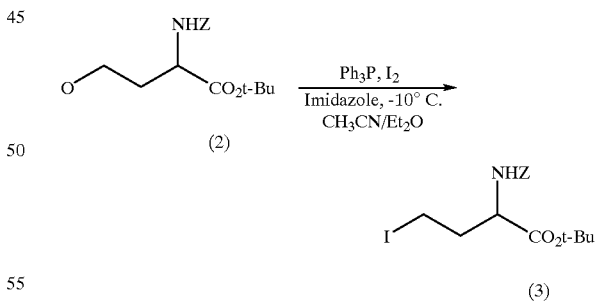

To a solution of the alcohol (2) (1.53 g, 4.95 mmols) in a 1:1 mixture of CH$_3$CN/Et$_2$O (50 mL), at −10° C., under $N_2$, were added successively imidazole (607 mg, 1.8 eq) and Ph$_3$P (2.21 g, 1.7 eq). Iodine (2.14 g, 1.7 eq) was then added in small portions over a period of 15 min. After the addition was completed, a white precipitate formed and the solution was brown. It was stirred at −10° C. for 45 min. It was then poured in Et$_2$O and the organic phase was washed with sat.aq. Na$_2$SO$_3$, sat.aq. CuSO$_4$, H$_2$O and dried over MgSO$_4$. The solids were filtered and the solvent evaporated to give a yellow oil that was purified by flash chromatography (silica gel, 5% to 20% EtOAc/Hex). The iodide (3) was obtained in 83% yield (1.71 g) as a clear oil.

$^1$H NMR (CDCl$_3$, 400 MHz): δ 7.41–7.31 (m, 5H, ArH), 5.35 (bd, 1H, J=7.3, NH), 5.13 (s, 2H, CH$_2$Ph), 4.30 (m, 1H, H-2), 3.22–3.12 (m, 2H, H-4), 2.42 (m, 1H, H-3), 2.20 (m, 1H, H-3), 1.48 (s, 9H, t-Bu).

Step 3

Synthesis of 2-Benzyloxycarbonylamino-4-hexenoic acid tert-butyl ester

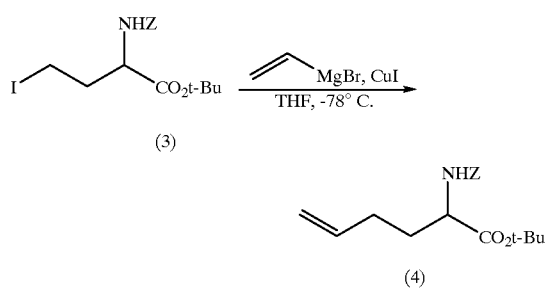

To a suspension of CuI (2.27 g, 5 eq) in dry THF (20 mL), at −78° C., under N$_2$, was added slowly a 1.0 M solution in THF of vinyl magnesium bromide (23.4 mL, 9.8 eq). The solution was then warmed up to −10° C. for 30 min (it turned then black) and cooled back to −78° C. A solution of the iodide (3) (1.00 g, 2.39 mmols) in dry THF (3.5 mL) was then added slowly to the cuprate solution. The reaction mixture was stirred at −78° C. for 2.5 hr. Sat. aq. NH$_4$Cl (50 mL) was added and the mixture was brought back to room temp. with vigorous stirring. It was then poured in Et$_2$O and stirred for 5 min. The dark suspension was filtered through a cintered funnel and the phases were separated. The aqueous phase was extracted with Et$_2$O (2×)and the combined organic extracts were dried over MgSO$_4$. The solids were filtered, the solvents evaporated and the crude oil purified by flash chromatography (silica gel, 5% AcOEt/Hex) to give 0.51 g (67%) of the pure alkene (4).

$^1$H NMR (CDCl$_3$, 400 MHz): δ 7.37–7.31 (m, 5H, ArH), 5.80 (m, 1H, H-5), 5.33 (d, 1H, J=7.8, NH), 5.12 (s, 2H, CH$_2$Ph), 5.05 (d, 1H, J=17.2, H-6), 5.01 (d, 1H, J=10.4, H-6), 4.30 (q, 1H, J=7.4, H-2), 2.16–2.08 (m, 2H, H-4), 1.92 (m, 1H, H-3), 1.74 (m, 1H, H-3), 1.48 (s, 9H, t-Bu).

Step 4

Synthesis of 1-Benzyloxycarbonyl-5-hydroxymethyl-2-pyrrolidinecarboxylic acid tert-butyl ester

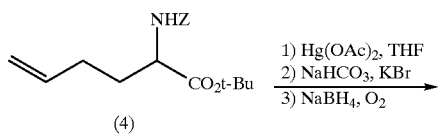

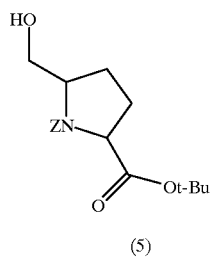

To a solution of the alkene (4) (50 mg, 0.157 mmol) in dry THF (3.1 mL), at r.t., under N$_2$, was added mercuric acetate (75 mg, 1.5 eq). The solution was stirred at r.t. for 18 hr after which it was cooled down to 0° C. Sat.aq. NaHCO$_3$ (2 mL) was then added and the mixture was stirred at 0° C. for 30 min. KBr (0.11 g, 6 eq) was added and the mixture was stirred at r.t. for 2 hr. It was then poured in H$_2$O/Et$_2$O and the phases were separated. The aqueous phase was extracted with Et$_2$O (2×) and the combined organic extracts were dried over MgSO$_4$. The solids were filtered and the solvents evaporated. Oxygen (O$_2$) was bubbled into a suspension of NaBH$_4$ (3.3 mg, 0.55 eq) in dry DMF (0.4 mL) for 1 hr, and to this was added dropwise (syringe pump, 3 mL/hr) a solution of the organomercurial bromide in DMF (3.1 mL) with continuous introduction of O$_2$. The bubbling was continued for 1 hr and Et$_2$O (5 mL) was added. The grey suspension was filtered through Celite and the filtrate was evaporated. The residue was chromatographed (silica gel, 6:4 Hex/EtOAc) to give the pyrrolidinol (5) (30 mg, 57%) as a clear oil.

$^1$H NMR (CDCl$_3$, 400 MHz): δ 7.37–7.28 (m, 5H, ArH), 5.22–5.09 (m, 2H, CH$_2$Ph), 4.30 (dd, 1H, J=1.4, 8.3, H-2), 4.24 (m, 1H, H-5), 3.70–3.57 (m, 3H, CH$_2$—OH), 2.25 (m, 1H), 2.13 (m, 1H), 1.92 (m, 1H), 1.70 (m, 1H), 1.34 (s, 9H, t-Bu).

Step 5

Synthesis of 1-Benzyloxycarbonyl-5-carboxy-2-pyrrolidinecarboxylic acid tert-butyl ester

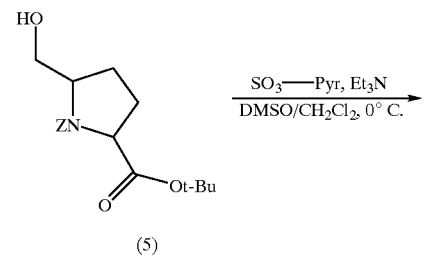

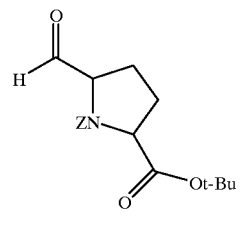

To a solution of the alcohol (5) (50 mg, 0.149 mmol) and Et$_3$N (62 µL, 3 eq) in dry CH$_2$Cl$_2$ (0.8 mL) is added slowly, under N$_2$, at 0° C., a solution of SO$_3$-Pyridine complex (71 mg, 3 eq) in dry DMSO. The solution was stirred at 0° C. for 30 min and 10% citric acid (2 mL) is added. The pH is brought to 4 with 1M NaOH and the aqueous phase is extracted with $Et_2O$ (3×). The combined organic extracts were dried over $MgSO_4$. The solids were filtered and the solvents evaporated to give a crude oil which was purified by flash chromatography (silica gel, 7:3 Hex/EtOAc). The pure aldehyde (6) was obtained as a clear oil (45 mg, 90%).

$^1$H NMR ($CDCl_3$, 400 MHz): δ 9.68+9.56 (ds, 1H, CHO), 7.36–7.29 (m, 5H, ArH), 5.23–5.11 (m, 2H, $CH_2Ph$), 4.57–4.39 (m, 2H, H-2, H-5), 2.30–1.97 (m, 4H, H-3, H-4), 1.47+1.36 (2s, 9H, t-Bu).

Step 6

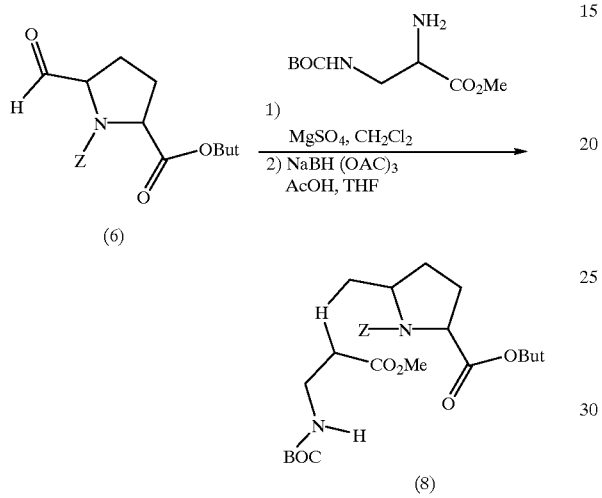

The pyrrolidine-aldehyde (6) is coupled with the protected diamino-propionic acid (7) by first forming the imine (8) ($MgSO_4$, $CH_2Cl_2$). Isolation of the imine (8) is done by filtration of the $MgSO_4$ and evaporation of the solvent. The crude imine is then treated with $NaBH(OAc)_3$ and actic acid (AcOH) in THF for 15 hours to obtain the amine (8) after extrative work-up.

Step 7

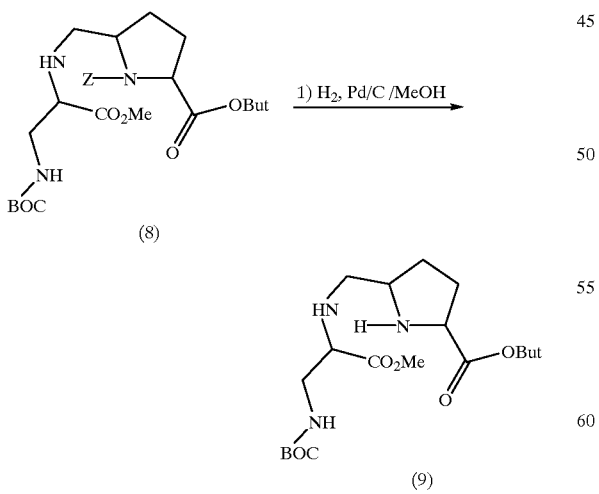

The CB7 (7) protecting group of the amine (8) is removed by hydrogenation with palladium on charcoal 10% as a catalyst in methanol (MeOH). The catalyst is filtered and the MeOH evaporated to give the crude diamine (9) that can be used without any purification.

Step 8

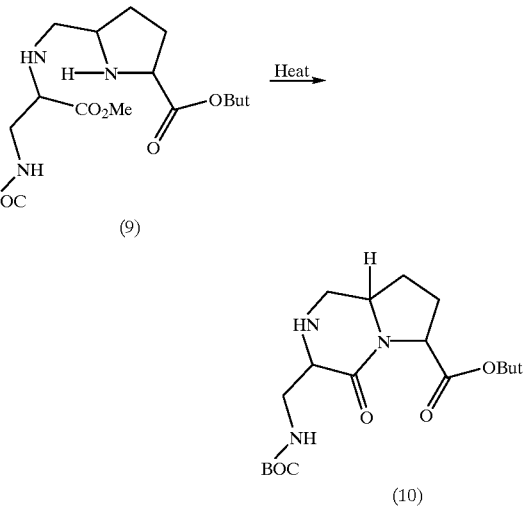

The cyclisation is done by heating the crude oil (9) from step 7, neat slightly above the boiling point of methanol. The bicyclic lactam (10) is purified by flash chromatography.

Step 9

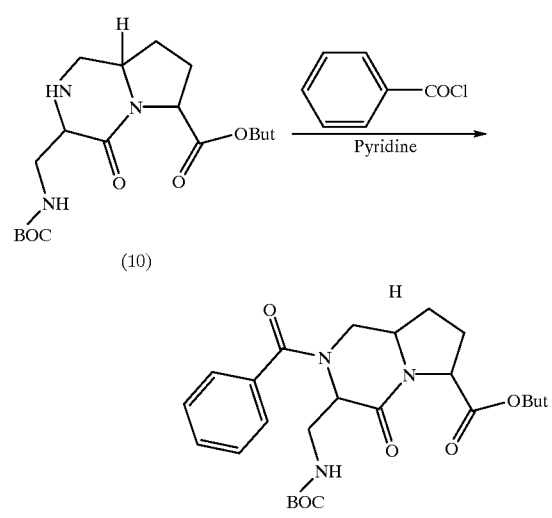

The secondary amine of the bicyclic lactam (10) is protected as an amide using benzoyl chloride in pyridine. Evaporation of the pyridine and extractive work-up give the bicyclic lactam-amide (11).

Step 10

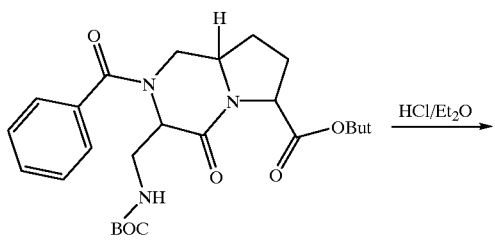

(11)

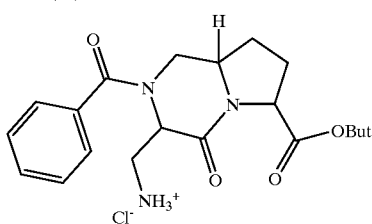

(12)

The BOC and t-butyl ester protecting groups of bicyclic lactam amide (11) are removed under acidic conditions (HCl in ethyl ether (Et$_2$O)). the amine salt (12) precipitates out of solution and is collected by filtration.

Step 11

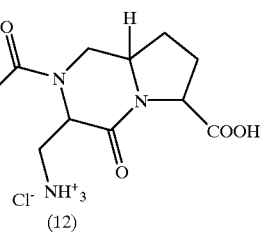

(12)

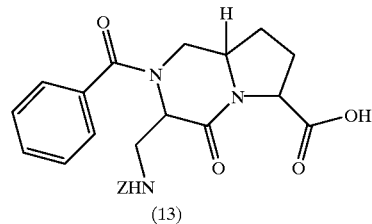

(13)

The primary amine of compound (12) is protected with a CBZ group by reacting it with benzyl chloroformate in cetonitrile (CH$_3$CN) with K$_2$CO$_3$ as a base. Extrative work-up gives fully protected carboxylic acid (13) which can be use for step 12 without further purification.

Step 12

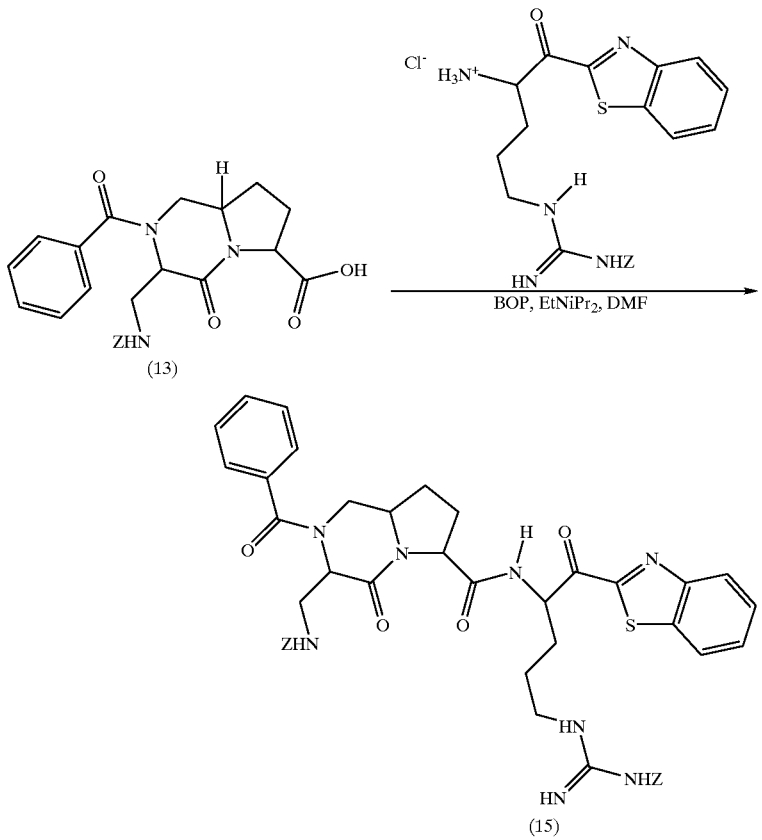

The carboxylic acid (13) is coupled with benzothiazole ketoarginine (14) in DMF using BOP as the coupling agent in the presence of diisorpopylethylamine (EtNiPr$_2$). Extrac tion with ethyl acetate (EtOAC) gives compound (15) as a solid which is purified by chromatography.
Step 13
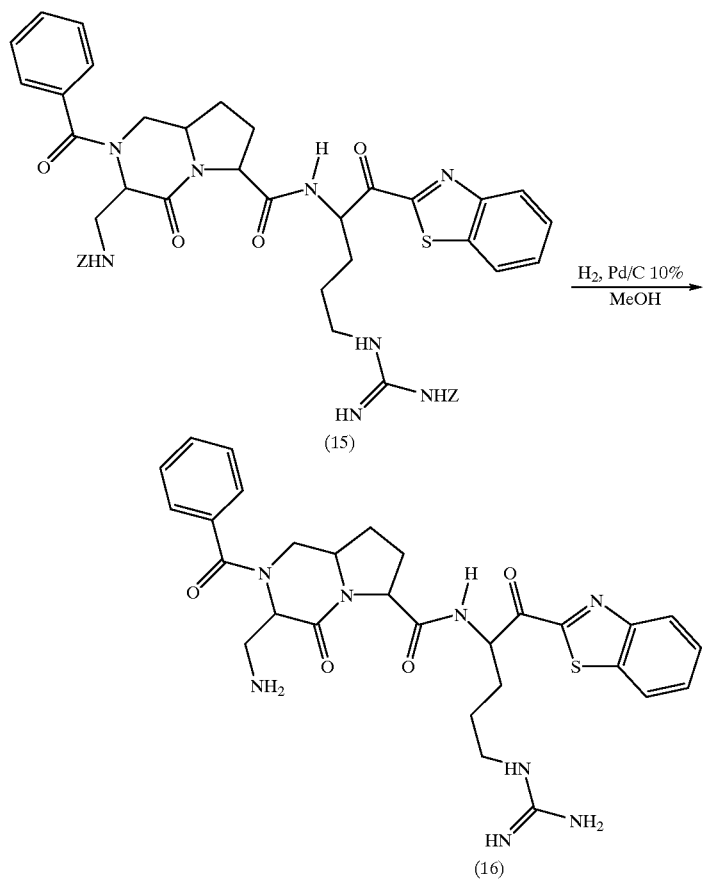
The two CBZ(Z) protecting groups of compound (15) are removed by catalytic hydrogenation with Pd/C 10% as a catalyst. The catalyst is filtered and the solvent is evaporated to give the amino-guanidine (16).
EXAMPLE 7
Synthesis of Compound (10)
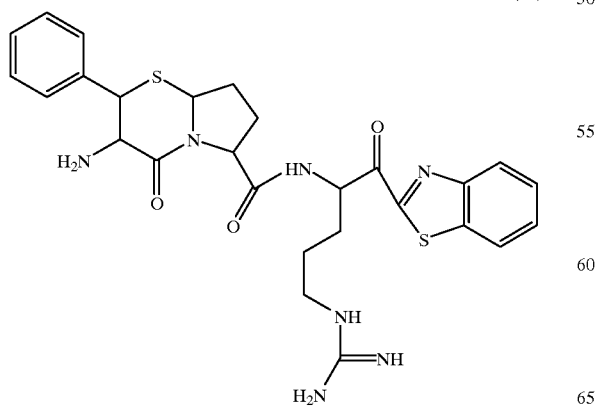

Step 1

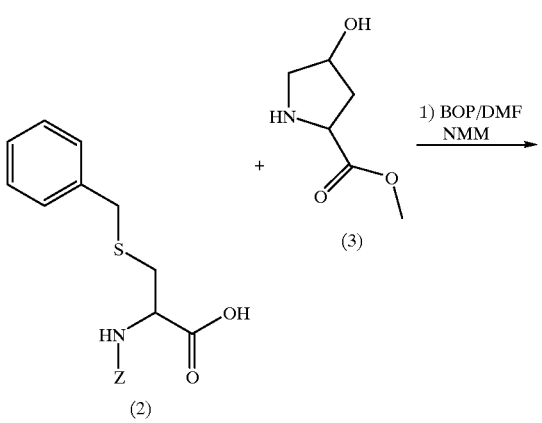

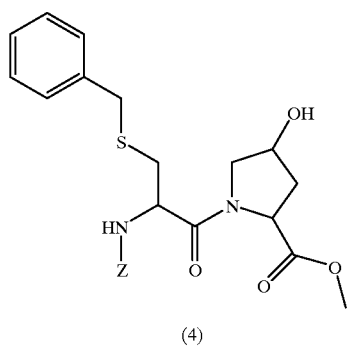

4-methylmorpholine (NMM) was added to a solution of the carboxylic acid (2) (1.7 g, 4.9 mmol, 1.0 eq). 4-hydroxyproline (3) (5.39 mmol, 1.1 eq), and BOP reagent (2.17 g, 4.9 mmol, 1.0 eq) in anhhydrous DMF (10 mL) at room temperature. The reaction mixture was stirred at room temperature over night, quenched with brine (50 mL) and ethyl acetate (100 mL). The organic layer washed with aqueous citric acid (10% 2×50 mL), sodium bicarbonate (10%, 2×50 mL) and brine (50 mL). The resulting organic layer was dried over anhydrous magnesium sulfate, filtered and the solvent evaporated. The crude residue was purified by flash chromatography (5:4:1, ethyl acetate hexane-methanol). 1.1 g of pure product (4) was recovered 48% yield.

Step 2

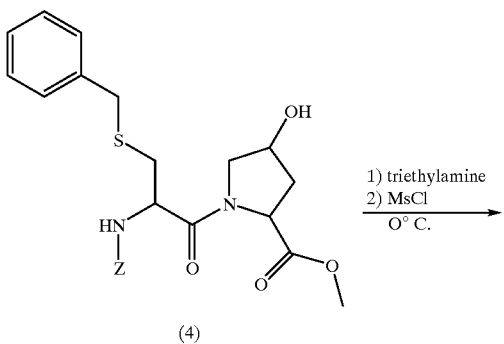

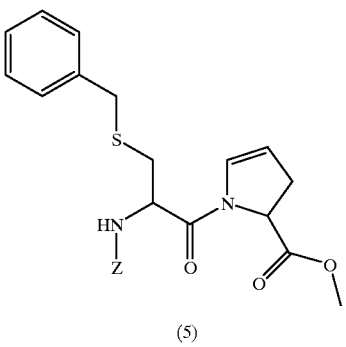

To a solution of 4-hydroxyproline derivative (4)(115 mg, 240 umol, 1.0 eq) in dichloromethane (10 mL, anhydrous) at 0° C. is added triethylamine (72 g, 720 umol, 3.0 eq) and methanesulfonyl chloride (28 mg, 240 umol, 1.0 eq) and the reaction mixture is stirred at room temperature. The mixture is then quenched with an aqueous solution of ammonium chloride and extracted with ethyl acetate. The organic layer is washed with 10% citric acid and brine, dried, filtered and the solvent is evaporated to dryness yielding compound (5).

Step 3

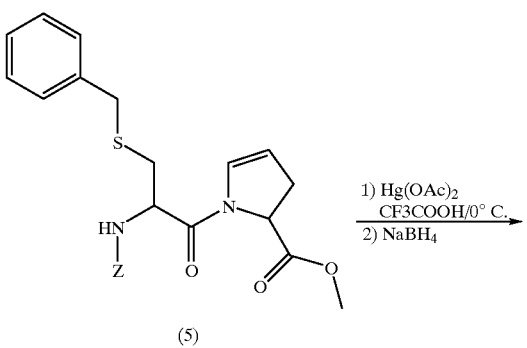

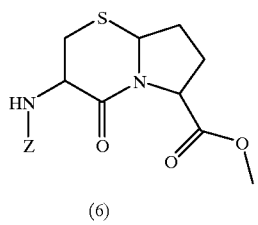

The enamine (5) (1.0 eq) is treated with mercuric acetate (1.1 eq) in THF. The solvent is evaporated to dryness and the residue dissolved in methanol. The resulting organo-mercurial is reductively cleaved with sodium borohydrine (1.3 eq). The resulting crude lactum thioether is purified by flash chromatography on silica gel affording compound (6).

Step 4

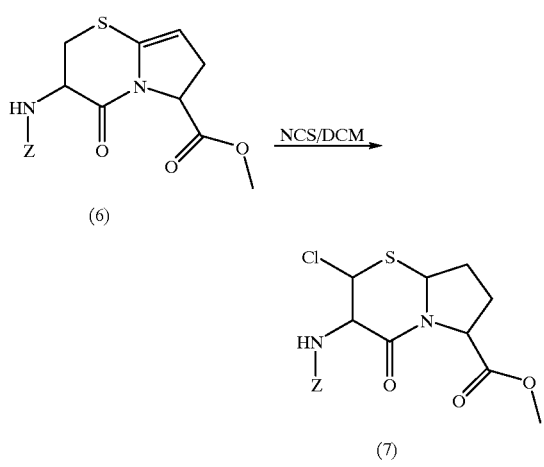

To a solution of the lactam thioether (6) (1.0 eq) in dry dichloromethane N-chlorosuccinimide (1.0 eq) is added at 0° C. The reaction mixture is warmed to room temperature. When the reaction shows no more starting material the solid is filtered and the solvent evaporated to dryness. The crude material (7) is use without any further purification for step 5.

Step 5

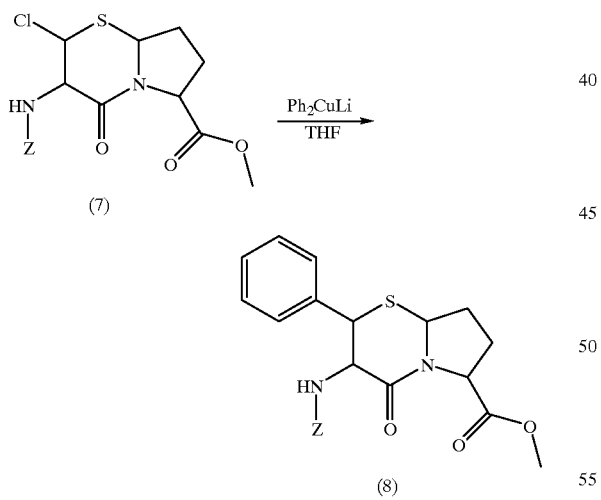

To a solution of the alpha-chlorothioether (7) (1.0 eq) in THF (anhydrous) a solution of phenylcuprate (1.0 eq) (prepared according to litterature procedure) is added at low temperature. When the reaction mixture shows no starting chlorothioether, brine and ethyl acetate is added. The organic layer is dried, filtered and evaporated to dryness to afford the desired product (8).

Step 6

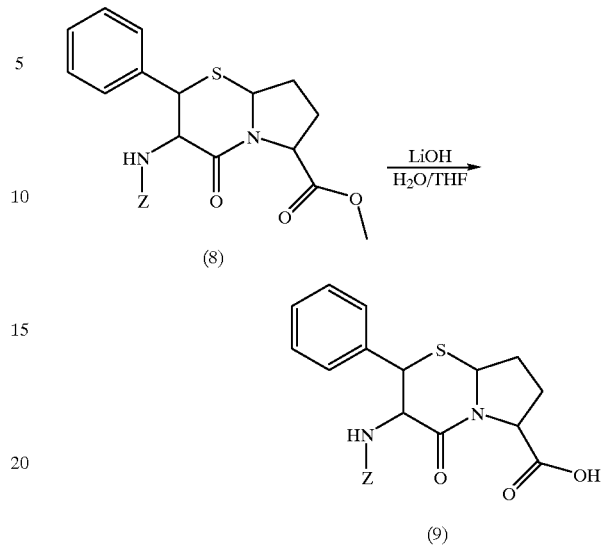

The isolated bicyclic lactam (8) is hydrolysed with one equivalent of lithium hydroxide in a 1:1 mixture of THF and water. The mixture is stirred at room temperature for 1 hour. The crude mixture is extracted with ether and the resulting solution is poured into 10% citric acic aqueous solution and extracted with dichloromethane to yield the corresponding carboxylic acid (9).

Step 6

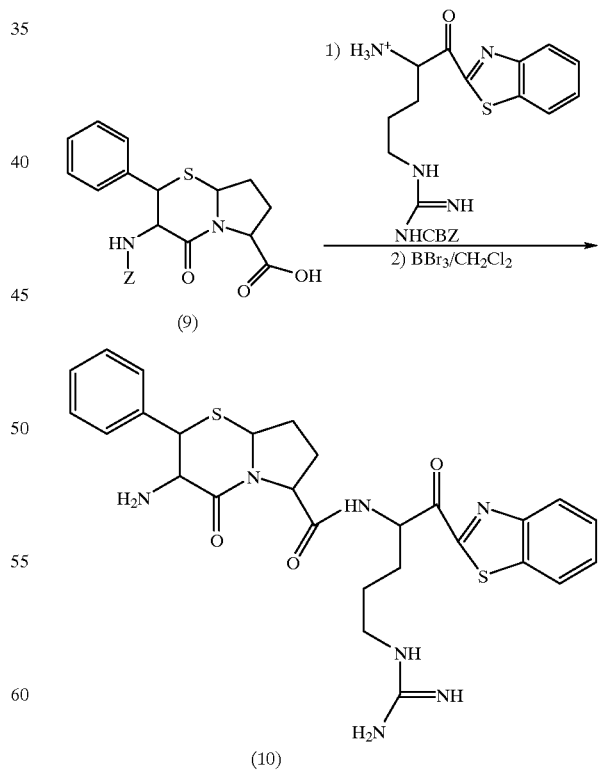

The crude carboxylic acid (9) is coupled with benzythiazole keto arginine in DMF using BOP as the coupling reagent in the presence of diisopropylethylamine. Extraction with EtOAc gives a solid that is purified on silica gel to give the protected amide. The CBZ protecting group is removed with BBr₃ in dichloromethane at room temperature finally gives the bicyclic benzothiazole keto arginine inhibitors (10). The following compounds are produced accordingly with the exception that the appropriate substitution of products were made in order to obtain the final compounds.

Compound #11

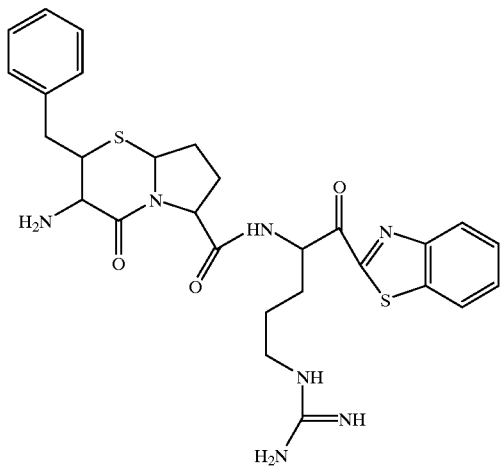

Compound #12

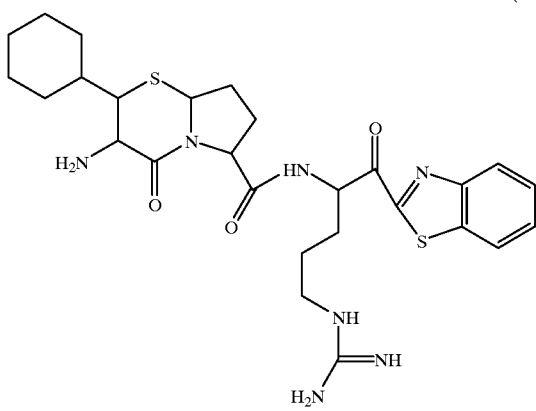

EXAMPLE 8

Step 1

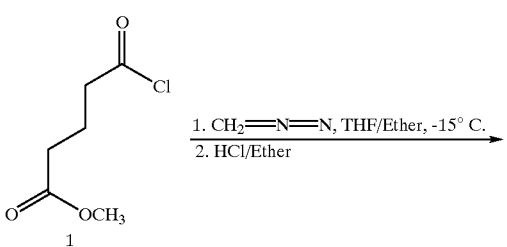

-continued

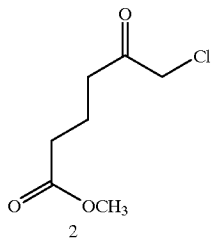

Commercially available glutaric acid monomethyl ester chloride (1)(20 ml, 0.144 mol) was disolved in 40 ml of dry tetrahydrofuran (THF) and cooled to −15° C. Excess diazomethane freshly prepared in 300 ml of Ether was introduced via cannula at 31 15° C. to the solution. The mixture was left to warm up to room temperature overnight. Excess diazomethane was evacuated from the flask with a current of argon. To bring the reaction to completion, 75 ml of 1 N HCl in Ether was added at 0° C. and left to warm up to room temperature for 5 hours. The volume of the solvent was reduced and then washed with 2×5% NaHCO₃ dried over Na₂CO₃ and evaporated to give crude chloromethylketone (20.46 g. 79%) wich was used in the next step without further purification.

¹H NMR (CDCL₃, 400 MHz) d 1.16–1.2 (t, 1H), 1.83–1.9 (m,2H), 2.27–2.35 (m,2H), 2.6–2.64(t,1H) 3.6(s,3H), 4.04 (s,2H)

Step 2

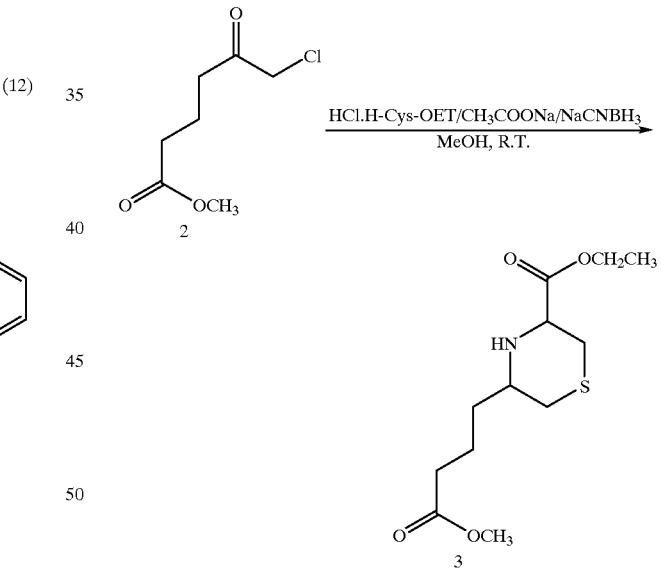

Crude chloromethylketone (2)(10.04 g, 56.15 mmol) was disolved in 300 ml of dry MeOH. Sodium acetate (2 eq, 9.21 g, 112.3 mmol) was added followed by L-Cysteine ethyl ester hydrochloride salt (1.3 eq, 13.55 g, 72.98 mmol) and sodium cyanoborohydride (1.4 eq, 4.9 g, 78.59 mmol). The heterogeneous mixture was left to stir at room temperature for 2 h 30 min. 200 ml of methanol (MeOH) was then added to dissolve all the solid and the pH was brought to 2 with 1N HCl. The mixture was then basified with saturated NaHCO₃ until pH=8. MeOH was evaporated and the remaining aqueous solvent was washed with ethyl acetate and dichloromethane. Solvents were combined, dried over Na₂SO₄ and evaporated. The crude residue was purified by silica gel flash column chromatography using a gradient of eluents ethyl acetate/hexane in the following ratios: (3:7, 5:5, 6:4, 7:3) giving cyclic compound (3).

$^1$H NMR (CDCl$_3$, 400 MHz) of compound (3) d 1.21–1.27 (t, 3H), J=7.06 Hz), 1.41–1.48 (m, 2H), 1.65–1.73 (m,2H), 2.28–2.39 (m,4H), 2.57–2.63 (t, 1H, J=10.9), 2.72–2.76 (dd, 1H, J=10.7 Hz), 2.8–2.86 (m, 1H), 3.6–3.64 (d, 4H, J=2.55 Hz), 3.63 (s, 3H), 4.13–4.2 (m, 2H)

$^{13}$C NMR (CDCl$_3$, 400 MHz) 13.078, 19.888, 28.326, 31.133, 32.741 35.277, 50.462, 56.394, 59.149, 60.188, 69.713, 170.182, 172.52

Step 4

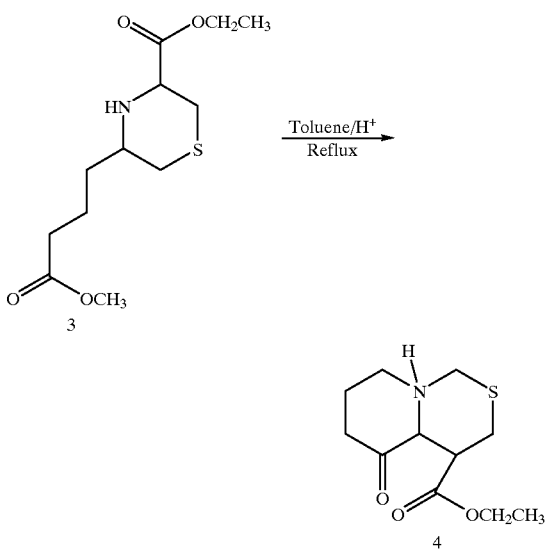

Cyclic compound (3) (913 mg, 3.32 mmol) was disolved in 50 ml of dry Toluene. (1S)-(+)-10-Camphorsulfonic acid (92 mg, 0.39 mmol) was added and the mixture was left to reflux for 4 days. When all starting material was shown to be consumed (by TLC), the mixture was worked up by evaporation of solvent, dissolving residue in ethyl acetate and washing with 2×5% NaHCO$_3$. The Ethyl acetate layer was dried over Na$_2$SO$_4$ and evaporated. The crude residue was purified by silica gel flash column chromatography using 60% ETOAC/40% Hexane followed by 70% ETOAC/30% Hexane giving 62.5% of Bicyclic compound (4).

$^1$N NMR (CDCl$_3$, 400 MHz) of compound (4) d 1.27–1.31 (t, 3H, J=7 Hz), 1.5–1.6 (m, 1H), 1.72–1.87 (m, 2H), 2.02–2.1 (m, 1H), 2.33–2.46 (m,2H), 2.52–2.59 (m, 2H), 2.83–2.88 (dd, 1H,J=14, 4 Hz), 3.14–3.18 (d, 1H), 3.78–3.85 (m, 1H), 4.2–4.27 (q, 2H, J=3.9 Hz), 5.9–5.92(t, 1H, J=3.4 Hz).

Step 5

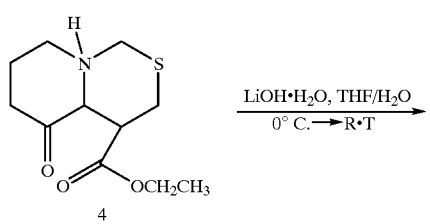

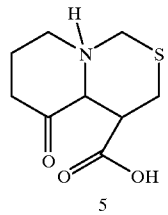

Bicyclic (4) (3.66 mg, 1.5 mmol) was dissolved in 25 ml of THF and 5 ml H$_2$O Lithium hydroxide monohydrate (1.1 eq, 7.05 mg, 1.68 mmol) was added in 2.3 ml of H$_2$O, at 0° C. and the mixture was left to stirr at 0° C. for 1 hr and at room temperature for 3 hrs. THF was then evaporated and the remaining aqueous mixture was acidified by addition of Citric acid until pH=2. Extraction of aqueous mixture with 2×CH$_2$CL$_2$ and 2×ETOAC drying of combined organic layers with Na$_2$SO$_4$ and evaporation gave a crude residue wich was purified by silica gel flash column chromatography using 70% ETOAC/30% Hexane followed by 4.7% HOAC/Ethyl acetate giving the pure acid (5) in 54% yield. 16% of starting material(4) was recovered.

$^1$H NMR (MeOD, 400 MHz) of compound (5) d 1.57–1.69, (m,1H), 1.70–1.80 (m, 1H), 1.81–1.89 (m, 1H), 2.05–2.12 (m, 1H), 2.35–2.5 (m, 2H), 2.51–2.66 (m, 2H), 2.86–2.91 (dd, 1H, J=13.8, 4 Hz), 3.12–3.17 (d, 1H), 3.3–3.32 (m, 1H), 3.78–3.84 (m, 1H), 5.76–5.78 (t, 1H), J=3.53 Hz).

$^{13}$C NMR (MeOD, 400 MHz) d 17.052, 27.07, 28.928, 31.382, 32.096, 51.016, 55.138, 170,088, 171.24

Step 6

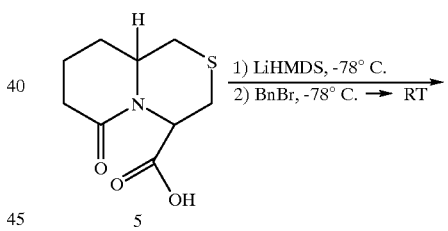

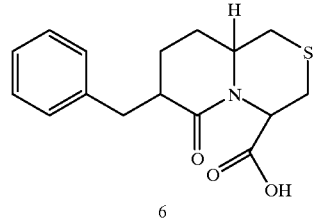

To a solution of lithium bis (trimethylsilyl) amide (5 ml of 1M THF solution, 5 mmol) in THF (10 ml) is added at −78° C. a solution of the carboxylic acid (5)(500 mg, 2.32 mmol) the resulting solution is stirred at −78° C. for 1 hour. Benzyl bromide (0.26 ml, 2.22 mmol) is then added and the mixture is allowed to reach room temperature and stirred for 15 hours. The mixture is then poured into 10% HCl (50 ml) and extracted wiht diclhoromethane (4×60 ml). The combined organic phases are dried over MgSO$_4$ and the solvent remove by evaporation to yield to the crude alkylated amide (6).

Step 7

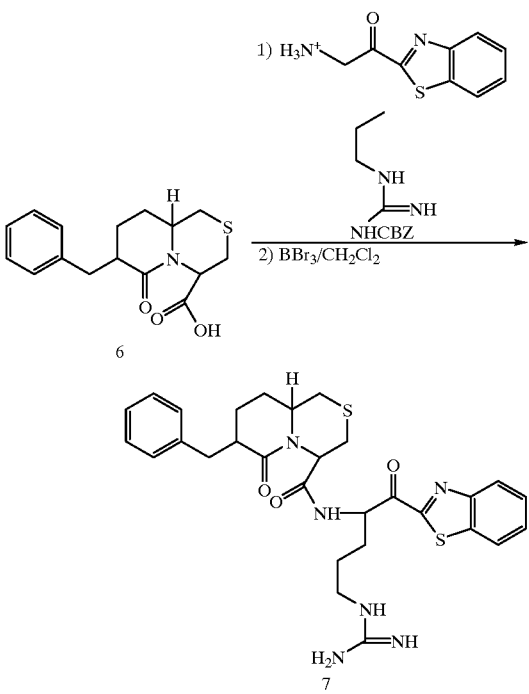

The crude aklylated amide (6) is coupled with benzythiazole keto arginine in DMF using BOP as the coupling reagent in the presence of diisopropylethylamine. Extraction with EtOAc gives a solid that is purified on silica gel to give the protected amide. The CBZ protecting group is removed with BBr$_3$ in dichloromethane at room temperature finally gives the bicyclic benzothiazole keto arginine inhibitors (7).

The following compound is produced accordingly with the exeption that the appropriate substitution of products were made in order to obtain the final compounds.

Compound #8

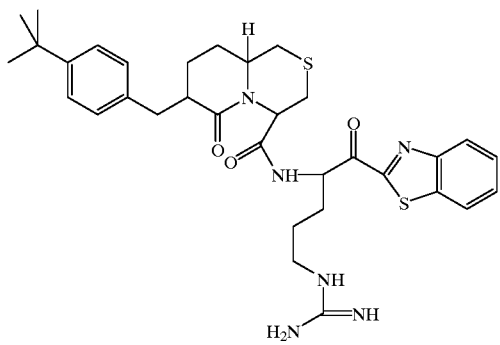

EXAMPLE 9

Determination of K$_1$ Values for Heterocyclics

The affinity of inhabitors for thrombin was measured according to the procedures described in (DiMaio et al, J. Bio. Chem, 1990, 265:21698) Inhibition of amidolytic activity of human thrombin was measured fluorometrically using Tos-Gly-Pro-Arg-AMC as a fluorogenic substrate in 50 mM Tris-HCl buffer (pH 7.52 at 37° C.) containing 0.1 M NaCl and 0.1% poly(ethylene glycol) 8000 at room temperature, and (Szewczuk et al., Biochemistry, 1992 31:9132).

The hydrolysis of the substrate by thrombin was monitored on a Varian-Cary 2000™ spectrophotometer in the fluorescence mode ($\lambda$eX=383, nm, $\lambda$eX=455 nm) or on a Hitachi F2000™ fluorecence spectometer ($\lambda_{ex}$=383, nm, $\lambda_{em}$=455 nm) and the fluorescent intensity was calibrated using AMC. The reaction reached a steady-state within 3 minutes after mixing thrombin with the substrate and an inhibitor. The steady-state velocity was then measured for a few minutes. The compounds of this invention were also pre-incubated with thrombin for 20 minutes at room temperature before adding the substrate. The steady-state was achieved within 3 min and measured for a few min. The kinetic data (the steady-state velocity at various concentrations of the substrate and the inhibitors) of the competitive inhibition was analyzed using the methods described by Segal (1975). A non-linear regressive program, RNLIN in the IMSL library (IMSL, 1978), LMDER in MINPACK library (More et al. 1980) or Microsoft™ Excel™, was used to estimate the kinetic parameters (K$_m$V$_{max}$ and K$_i$).

dTT assay

The fibrin clotting assay was performed in 50 mM Tris-HCl buffer (pH 7.52 at 37° C.) containing 0.1 M NaCl and 0.1% poly(ethylene glycol) 8000 with 9.0×10—10 M (0.1 NIH unit/mL) and 0.03% (w/v) of the final concentration of human thrombin and bovine fibrinogen, respectively, as reported elsewhere (Szewczuk et al., supra). The clotting time was plotted against the inhibitor concentrations and the IC$_{50}$ was estimated as the inhibitor concentration required to double the clotting time relative to the control. Results are summarized in Tables 1 or 2 below.

Fibrin Clot Assay

The fibrin clot assay was performed essentially as described by Krtenansky et al, FEBS, 1987, 211:10. A serial dilution of the inhibitor was prepared in 50 mM tri HCl buffer (pH 7.8 at 23° C.) containing 0.1 M NaCl and 0.1% (w/v) polyethylene glycol 8000. Human plasma (60 $\mu$L, collected in 3.8% sodium citrate, blood/anticoagulate 9:1) was added to microtiter wells (microtiter plate, Falcon) containing 100 $\mu$L of various inhibitor dilutions. The solution was mixed after which 50 $\mu$L of human thrombin (1 nM final conc.) was added and mixed for 15 seconds. The turbidity of the clot was immediately monitored by microplate autoreader (Dynateck MR 5000) at 405 nm and recorded every 3 min. The maximal turbidity in the absence of inhibitors was reached within 60 min. IC$_{50}$ values were calculated at 30 minutes as the inhibitor concentration that gave half the optical density of the control.

Platelet Aggregation and Secretion

Rat blood was collected into ACD (6/1 v/v) by cardiac puncture. Suspensions of washed platelets were prepared as described by Ardlie et al, (Br. J. Haematol. 1970, 19:7 and Proc. Soc. Exp. Biol. Med. 1971, 136:1021). The final suspending medium was a modified Tyrode solution (NaCl 138 mM, KCl 2.9 mm, HEPES 20 mM, NaH$_2$PO$_4$ 0.42 mM, NaHCO$_3$ 12 mM, CaCl$_2$, 1 mM, MgCl$_2$ 2 mM 0.1% glucose, 0.35% albumin, apyrase 1 $\mu$L/mL pH 7.4). Platelet counts were adjusted to 5000,000/ $\mu$L.

To permit measurement of the extent of release of the contents of the dense granules, the platelets were labelled in the first washing solution with $^{14}$C-serotonin (5-HT) (1 $\mu$Ci/10 mL of washing fluid) and release of $^{14}$C-serotonin was determined as described in Holmsen et al, (Enzymology, 1989, 169:206). Inipramine (5 $\mu$M final conc.) was added to present the reuptake of released serotonin.

Platelet aggregation was recorded at 37° C. in an aggregometer (BioData PAP-4) at a stirring speed of 1,100 rpm by measuring the variations of light transmission. Percentage of aggregation was determined 3 min after the addition of the stimulating agent (human thrombin 0.1IU/mL final conc.) Inhibitors were preincubated 1 minute at 37° C. before addition of stimulating agent. $IC_{50}$ values represent the concentration that was necessary to inhibit platelet aggregation or secretion to 50% of the control.

Arterial Thrombosis Model $FeCl_3$ Induced Carotid Arterial Injury Model

The $FeCl_3$ induced injury to the carotid artery in rats was induced according to the method described by Kurz, K. D., Main, R. W. Sandusky, G. E., Thrombosis Research 60; 269–280, 1990 and Schumacher, W. A. et al. J. Pharmacology and Experimental Therapeutics 267; 1237–1242, 1993. Mael, Sprague-Dawley rats (375–410 g) were anesthetized with urethane (1500 mg/kg ip). Animals were laid on a 37° C. heating pad. The carotid artery was exposed through a midline cervical incision. Careful blunt dissection was used to isolate the vessel from the carotid sheath. Using forceps, the artery was lifted to provide sufficient clearance to insert two small pieces of polyethylene tubing (PE-205*) underneath it. A temperature probe (Physitemp*MT23/3) was placed between one of the pieces of tubing and the artery. Injury was induced by topical application on the carotid artery above the temperature probe of a small disc (3 mm dia.) of Whatman* No. 1 filter paper previously dipped in a 35% solution of $FeCl_3$ from degradation by light. The vessel temperature was monitored for 60 minutes after application of $FeCl_3$ as an indication of blood flow. Vessel temperature changes were recorded on a thermister (Cole-Palmer* Model 08533-41).

The time between the $FeCl_3$ application and the time at which the vessel temperature decreased abruptly (>2.4° C.) was recorded as the time to occlusion of the vessel. Inhibitor compounds were given as an iv bolus (mg/kg) followed immediately by an iv infusion (μg/kg/min. via femoral vein). The dose of inhibitor needed to double the time to occlusion in comparison to control animals in which injury was induced in the absence of inhibitor was determined.

TABLE 1

| cmpd | Antiplatelet activity μM | | | dTT $IC_{50}$ μM | Plasma fibrin clot assay $IC_{50}$ μM |
|---|---|---|---|---|---|
| | $Ki$ $\mu M^a$ | Aggregation * | 5-HT Secretion | | |
| 0005 | 4 | ND | ND | 47 | >450 |
| 0010 | 4.6 | 21 | 19 | 89.5 | >450 |
| 0015 | 16 | >100 | >100 | 162 | >450 |
| 0020 | 2.2 | 18 | 14.2 | 22 | >450 |
| 0025 | 53 | >100 | >100 | >625 | >450 |
| 0030 | 8.6 | >100 | >100 | 67 | 320 |
| 0035 | 34 | >100 | >100 | 319 | >450 |
| 0040 | 19 | >100 | >100 | 207.5 | >450 |
| 0045 | 74 | ND | ND | 415 | >450 |
| 0050 | 62 | ND | ND | | >450 |
| 0065 | 32.7 | 47.5 | 52 | 42 | 200 |
| 0070 | 4.4 | 22 | 2.1 | 25 | 78 |
| 0080 | 0.048 | 0.4 | 0.38 | 0.375 | ND |
| 0090 | 0.031 | ND | ND | 0.33 | ND |
| 0095 | 26 | ND | ND | | |
| 0100 | 19 | ND | ND | 165 | ND |

*suspension of washed platelets from rats
[a]Inhibitory dissociation constant for human α-thrombin

TABLE 2

| Compound | Ki (nM) | dTT (nM) | Route ivb + inf | M.O.T (min)+/−sem |
|---|---|---|---|---|
| 0220 | 18 | | | |
| 0225 | 550 | | 0.75–50 | 23+/−7 |
| | 235 | | | |
| 0245 | 5 | | 0.5–30 | 27+/−3 |
| | 8 | | 0.75–50 | 22.6+/−2.6 |
| 0250 | 40 | 350 | 0.25–20 | 23+/−8 |
| | | | 0.75–50 | 22+/−3 |
| 0295a | 1500 | | 0.75–50 | 20+/−1 |
| 0295b | | 5000 | | |
| | | 520 | 0.75–50 | 19+/−2.7 |
| 0240 | 18 | | 0.75–50 | 17+/−2.6 |
| 0210 | 8 | | 0.75–50 | 20.13+/−3.4 |
| 0255 | 500 | | | |
| 0260 | 16 | | 0.75–50 | 14.83+/−0.2 |
| 0305a | 220 | | | |
| 0305b | 12000 | | | |
| 0265a | 4 | | 0.75–50 | 21.5+/−10 |
| 0265b | 18 | | 0.75–50 | 14.83+/−2.3 |
| 0285 | 10 | | 0.75–50 | 11.33+/−1.34 |
| | 150 | | | |
| 0315a + b | 45 | | | |
| 0315b | 10 | | 0.75–50 | 30.33+/−8.4 |
| 0335 | 25 | 138 | 0.75–50 | 45.8+/−14.2 |
| | | | 0.5–30 | 41.5+/−7.27 |
| | | | 0.25–20 | 27.5+/−11,3 |
| 0340 | 0.6 | | 0.25–20 | 36+/−9,6 |
| | | | 0.75–50 | 42.25+/−11,9 |
| 0345 | 2 | | 0.75–50 | 50+/−5.86 |
| 0915 | 1600 | | 0.75–50 | 15+/−1,3 |
| 0935 | 120 | | | |
| 0925a + b | 10 | | 0.75–50 | 19.6+/−0.2 |
| 0925b | 30 | | | |
| 0925a | 7 | | 0.75–50 | 20.3+/−3.5 |
| 0940a | 16 | | 0.75–50 | 15.2+/−0.82 |
| 0940b | 160 | | | |
| 0950a | 150 | | | |
| 0950b | 1000 | | | | a = early eluting on RP HPLC single isomer
b = late eluting on RP HPLC single isomer
a + b = mixture

We claim:

1. A compound of formula (VIII):

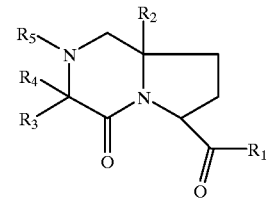

(VIII)

wherein $R_1$ is selected from the group consisting of formula VIa to VId:

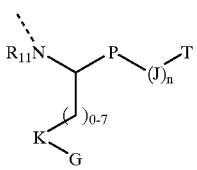

VIa

-continued

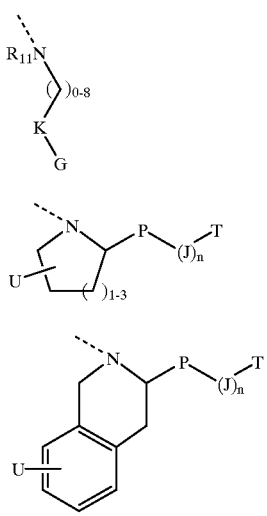

wherein:

R₁₁ is hydrogen or $C_{1-6}$ alkyl;

K is a bond or a —NH—;

G is $C_{1-4}$ alkoxy; cyano; —NH₂; —CH₂—NH₂; —C(NH)—NH₂; —NH—C(NH)—NH₂; —C(NH)—C(NH)—NH₂; a $C_6$ cycloalkyl or aryl substituted with cyano, —NH₂, —CH₂, —NH₂, —C(NH)—NH₂, —NH—C(NH)—NH₂ or —CH₂—NH—C(NH)—NH₂; or a 5 or 6 member, saturated or unsaturated heterocycle optionally substituted with cyano, —NH₂; —CH₂—NH₂; —C(NH)—NH₂; —NH—C(NH)—NH₂; or —CH₂—NH—C—(nh)—NH₂;

U is cyano, —NH₂; —C(NH)—NH₂ or —NH—C—(NH)—NH₂;

P is a bond, —C(O)—or a bivalent group;

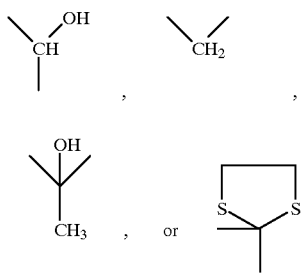

J is $C_{1-6}$ alkylene optionally substituted with OH, NH₂ or $C_{1-6}$ alkyl and optionally interrupted by a heteroatom selected from O, S, and N;

n is 0 or 1; and

T is selected from the group consisting of H, OH, amino, a peptide chain, $C_{1-16}$ alkyl, $C_{1-16}$ alkoxy, $C_{6-20}$ aralkyl, and a moiety selected from the group consisting of:

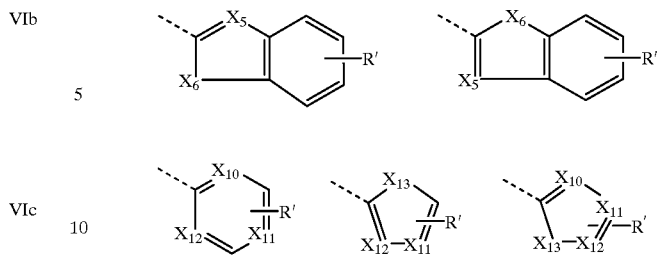

wherein $X_5$, $X_{10}$, $X_{11}$ and $X_{12}$ are each independently selected from the group consisting of N, and C—X₇ where $X_7$ is hydrogen, $C_{1-4}$ alkyl, or $C_{5-8}$ aryl;

$X_6$ and $X_{13}$ are each independently selected from the group consisting of C, O, N, S, N—X₇, and CH—X₇;

R' is hydrogen, $C_{1-16}$ alkyl optionally carboxyl substituted, carboxyl, —$C_{0-16}$ alkyl—CO₂—$C_{1-16}$ alkyl, $C_{6-20}$ aralkyl, $C_{3-7}$ cycloalkyl, aryl, an aromatic, and a 5 to 10 element mono- or bi- cyclic saturated or unsaturated heterocycle group with 1 to 4 heteroatoms selected from the group consisting of N, O and S, optionally mono- or di-substituted with OH, SH, amino, halogen, CF₃, oxo, and $C_{1-6}$ alkyl;

R₂ is H or C1–6 alkyl;

R₃ is selected from H, NR₆R₇ and $C_{1-6}$ alkyl; and

R₄ and R₅ are independently selected from H; NR₆R₇; $C_{6-16}$ aryl or $C_{3-7}$ cycloalkyl optionally substituted with $C_{1-6}$ alkyl; $C_{1-16}$ alkyl optionally interrupted by one or more heteroatom or carbonyl group and optionally substituted with OH, SH, NR₆R₇ or a $C_{6-16}$ aryl, heterocycle or $C_{3-7}$ cycloalkyl group optionally substituted with halogen, hydroxyl, $C_{1-6}$ alkyl; an amino acid side chain; and a hydrophobic group selected from the group consisting of $C_{1-20}$ alkyl, $C_{2-20}$ alkynyl optionally interrupted by a carbonyl group $C_{6-16}$ aryl, $C_{3-7}$ cycloalkyl, $C_{6-20}$ cycloalkyl substituted $C_{1-20}$ alkyl, wherein the aliphatic portion is optionally interrupted by a carbonyl group and the ring portion is optionally interrupted by a carbonyl group and the ring portion is optionally substituted with $C_{1-6}$ alkyl; and a hydrophobic amino acid side chain.

2. A compound according to claim 1, wherein T is selected from the group consisting of:

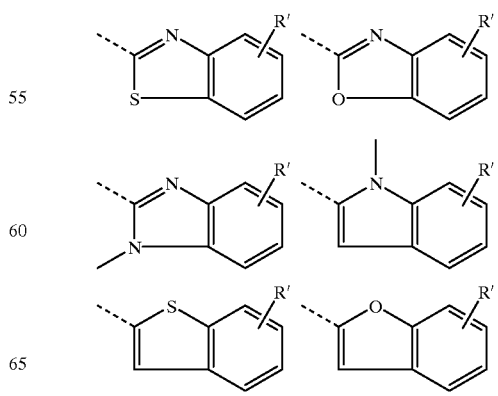

-continued

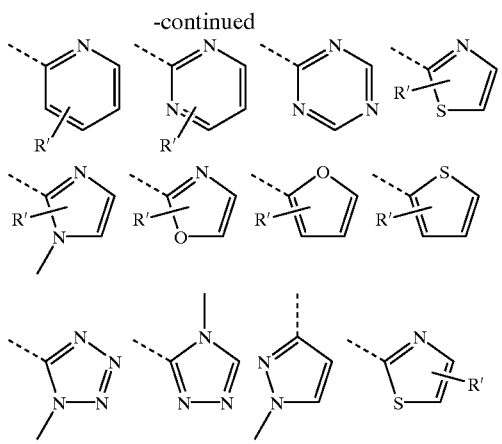

and R' is hydrogen, $C_{1-16}$ alkyl optionally carboxyl substituted, carboxyl, —$C_{0-16}$ alkyl—$CO_2$—$C_{1-16}$ alkyl, $C_{6-20}$ aralkyl, $C_{3-7}$ cycloalkyl, aryl or an aromatic 5 to 10 element mono- or bi- cyclic saturated or unsaturated heterocycle group with 1 to 4 heteroatoms selected from the group consisting of N, O, and S, optionally mono- or di-substituted with OH, SH, amino, halogen, $CF_3$, oxo, and $C_{1-6}$ alkyl.

3. A compound according to claim 2, wherein T is selected from:

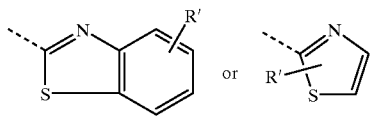

and R' is hydrogen, $C_{1-16}$ alkyl optionally carboxyl substituted, carboxyl, —$C_{0-16}$ alkyl—$CO_2$—$C_{1-16}$ alkyl, $C_{6-20}$ aralkyl, $C_{3-7}$ cycloalkyl, aryl or an aromatic 5 to 10 element mono- or bi- cyclic saturated or unsaturated heterocycle group with 1 to 4 heteroatoms selected from the group consisting of N, O, and S, optionally mono- or di-substituted with OH, SH, amino, halogen, $CF_3$, oxo, and $C_{1-6}$ alkyl.

4. A compound according to claim 1, wherein $R_2$ and $R_3$ are both H.

5. A compound according to claim 1, wherein $R_4$ is H or $C_{1-6}$ alkyl substituted with COOH.

6. A compound according to claim 1, wherein $R_2$, $R_3$ and $R_4$ are H and $R_5$ is $C_{1-16}$ alkyl optionally interrupted by one or more heteroatom or carbonyl group and optionally substituted with OH, SH, $NR_6R_7$ or a $C_{6-16}$ aryl, heterocycle or $C_{3-7}$ cycloalkyl group optionally substituted with halogen, hydroxyl or $C_{1-6}$ alkyl.

7. A compound according to claim 1, wherein:

$R_2$, $R_3$ and $R_4$ are H; and $R_5$ is $C_{1-16}$ alkyl optionally interrupted by one or more heteroatom or carbonyl group and optionally substituted with OH, SH, $NR_6R_7$ or a $C_{6-16}$ aryl, 5 to 10 element mono- or bi- cyclic saturated or unsaturated heterocycle group with 1 to 4 heteroatoms selected from the group consisting of N, O, and S, optionally mono- or di-substituted with OH, SH, amino, halogen, $CF_3$, oxo, and $C_{1-6}$ alkyl.

8. A compound according to claim 1, selected from:

4Oxo-2-(3-phenyl-propionyl)-octahydro-pyrrol[1,2a]pyrazine-6carboxylic acid [4-guanidino-1-(5-methyl-thiazole-2-carbonyl)-butyl]-amide; and 4-Oxo-2(3-phenyl-propionyl)-octahydro-pyrrolo[1,2-a]pyrazine-6-carboxylic acid [4-guanidino-1-(thiazole-2-carbonyl)-butyl]-amide.

* * * * *